(12) United States Patent
Alfaro-Lopez et al.

(10) Patent No.: US 8,642,544 B2
(45) Date of Patent: Feb. 4, 2014

(54) N-TERMINUS CONFORMATIONALLY CONSTRAINED GLP-1 RECEPTOR AGONIST COMPOUNDS

(75) Inventors: Josue Alfaro-Lopez, San Marcos, CA (US); Abhinandini Sharma, San Diego, CA (US); Soumitra S. Ghosh, San Diego, CA (US)

(73) Assignees: Amylin Pharmaceuticals, LLC, San Diego, CA (US); AstraZeneca Pharmaceuticals LP, Wilmington, DE (US)

( * ) Notice: Subject to any disclaimer, the term of this patent is extended or adjusted under 35 U.S.C. 154(b) by 0 days.

(21) Appl. No.: 13/260,702

(22) PCT Filed: Mar. 26, 2010

(86) PCT No.: PCT/US2010/028883
§ 371 (c)(1),
(2), (4) Date: Oct. 27, 2011

(87) PCT Pub. No.: WO2010/120476
PCT Pub. Date: Oct. 21, 2010

(65) Prior Publication Data
US 2012/0046222 A1 Feb. 23, 2012

Related U.S. Application Data

(60) Provisional application No. 61/165,604, filed on Apr. 1, 2009.

(51) Int. Cl.
*A61K 38/26* (2006.01)
*A61K 38/16* (2006.01)
*A61K 38/00* (2006.01)

(52) U.S. Cl.
USPC .......... 514/7.2; 514/11.7; 514/21.3; 530/300; 530/308

(58) Field of Classification Search
None
See application file for complete search history.

(56) References Cited

U.S. PATENT DOCUMENTS 6,620,910 B1 9/2003 Calas et al.
2004/0242853 A1 12/2004 Greig et al.

FOREIGN PATENT DOCUMENTS

WO  WO 2008/023050 A1  2/2006
WO  WO 201001301 A2 *  2/2010

OTHER PUBLICATIONS

Green et al., Curr. Pharm. Design 10:365-3662 (2004): "Structurally modified analogues of glucagon-like peptide (GLP-1) and glucose-dependent insulinotropic polypeptide (GIP) as future antidiebatic agents".
International Search report of PCT/US 10/28883 mailed Oct. 7, 2010.
Supplementary European Search Report dated Nov. 11, 2012.

* cited by examiner

*Primary Examiner* — Christine J Saoud
*Assistant Examiner* — Jegatheesan Seharaseyon
(74) *Attorney, Agent, or Firm* — Womble Carlyle Sandridge & Rice, LLP; Mark J. Pino; Alireza Behrooz

(57) ABSTRACT

The disclosure provides N-terminus conformationally constrained compounds, which may comprise peptide mimetics and/or amino acid substitutions, which may be used in peptides, such as GLP-1 receptor agonist compounds, to induce a β-turn secondary structure at the N-terminus. The N-terminus conformationally constrained compounds may be used for research purposes; to produce GLP-1 receptor agonist compounds having improved GLP-1 receptor binding activity, enzymatic stability, or in vivo glucose lowering activity; and to develop GLP-1 receptor agonist compounds which have fewer amino acid residues. The disclosure also provides GLP-1 receptor agonist compounds, such as exendins, exendin analogs, GLP-1 (7-37), GLP-1 (7-37) analogs, comprising the N-terminus conformationally constrained compounds. The compounds are useful for treating various diseases, such as diabetes and obesity. The disclosure also provides methods for chemically synthesizing the N-terminus conformationally constrained compounds.

3 Claims, 23 Drawing Sheets

Figure 1A    HGEGTFTSDLSKQMEEEAVRLFIEWLKNGGPSSGAPPPS-NH$_2$

Figure 1B    H-dAla-PGTFTSDLSKQMEEEAVRLFIEWLKNGGPSSGAPPPS-NH$_2$

Figure 1C    H-dAla-PGTFTSDLSKQLEEEAVRLFIEFLKN-NH$_2$

Figure 2A HGEGTFTSDLSKQLEEEAVRLFIEWLKQGGPSKEIIS

Figure 2N

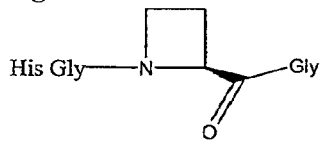

Figure 2O

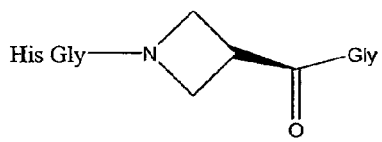

Figure 2P

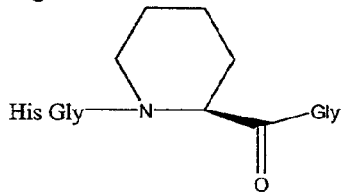

Figure 2Q

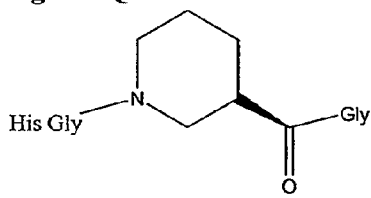

Figure 2R

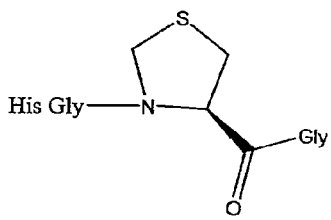

Figure 2S

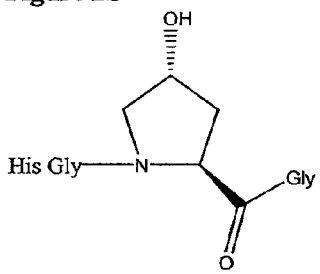

Figure 2T

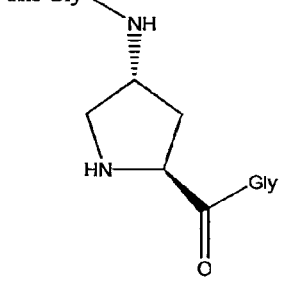

Figure 2U

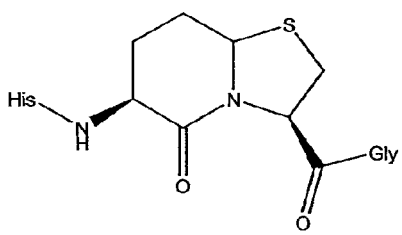

Figure 3A      H-dAla-PGTFTSDLSKQMEEEAVRLFIEWLKNGGPSSGAPPPS-NH$_2$

Figure 3B      HAPGT FTSDL SKQME EEAVR LFIEW LKNGG PSSGA PPPS-NH$_2$

Figure 3C      HGPAT FTSDL SKQME EEAVR LFIEW LKNGG PSSGA PPPS-NH$_2$

Figure 3D      HAPAT FTSDL SKQME EEAVR LFIEW LKNGG PSSGA PPPS-NH$_2$

Figure 3E      HGP-dAla-T FTSDL SKQME EEAVR LFIEW LKNGG PSSGA PPPS-NH$_2$

Figure 3F      HVPGT FTSDL SKQME EEAVR LFIEW LKNGG PSSGA PPPS-NH$_2$

Figure 3G      H-NMeAla-PGT FTSDL SKQME EEAVR LFIEW LKNGG PSSGA PPPS-NH$_2$

* p<0.05 v. vehicle control; ANOVA, Dunnett's test.

Figure 5A    HGEGT FTSDL SKQLE EEAVR LFIEF LKN
Figure 5B                   Figure 5C                 Figure 5D
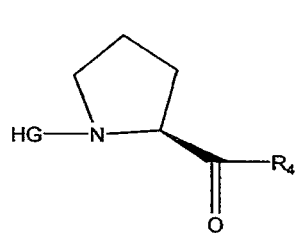 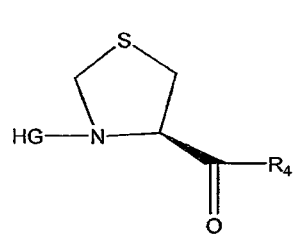 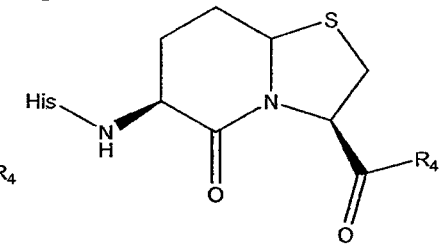
Figure 5E                   Figure 5F                 Figure 5G
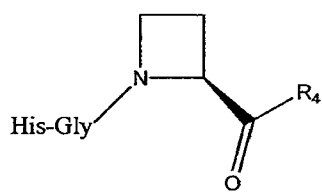 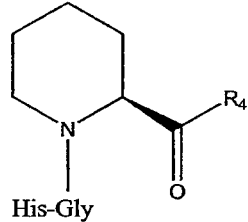 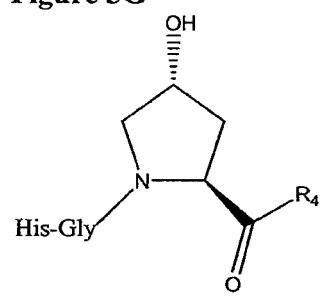
Figure 6A
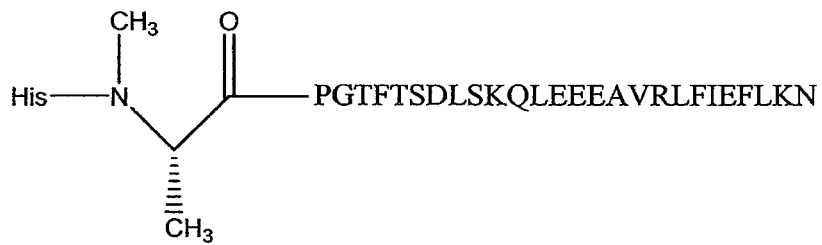
Figure 6B
Figure 6C    HVPGT FTSDL SKQLE EEAVR LFIEF LKN
Figure 6D    HAPGT FTSDL SKQLE EEAVR LFIEF LKN
Figure 6E    H-dAla-P-dAla-T FTSDL SKQLE EEAVR LFIEF LKN Points represent mean ± sd.

\* $p<0.05$ vs. vehicle control; ANOVA, Dunnett's test.

Points represent mean ± sd.

Figure 14G
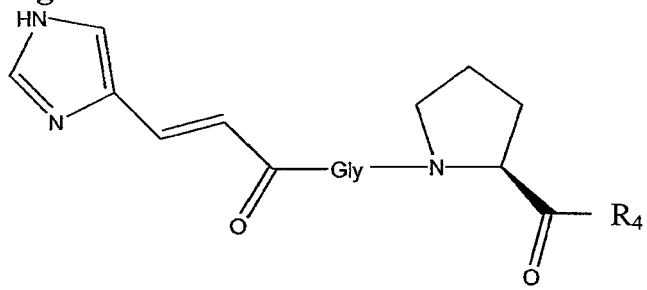
Figure 14H
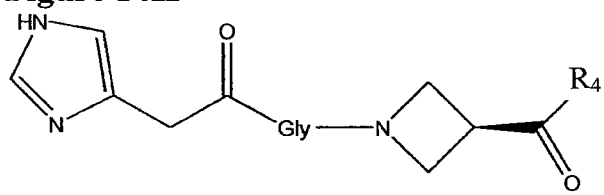
Figure 14I                    Figure 14J
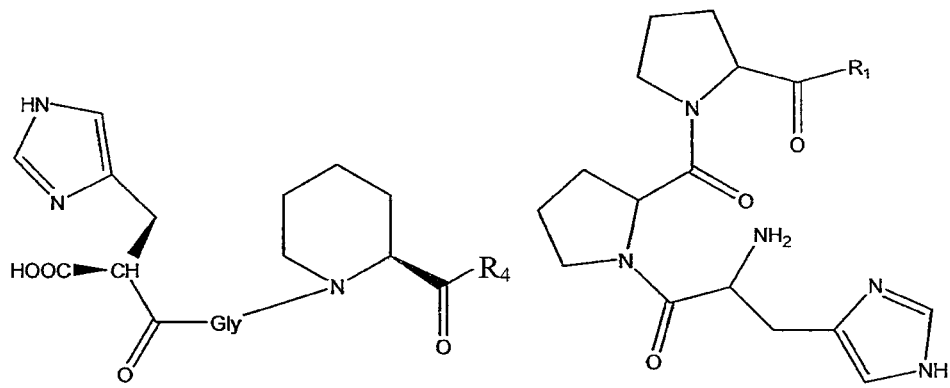
Figure 14K
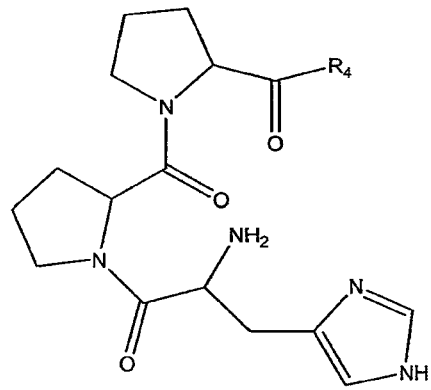

Figure 14L
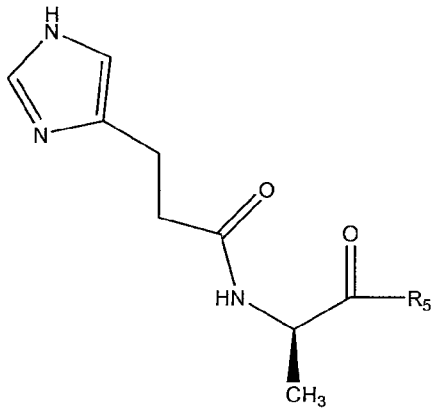
Figure 14M
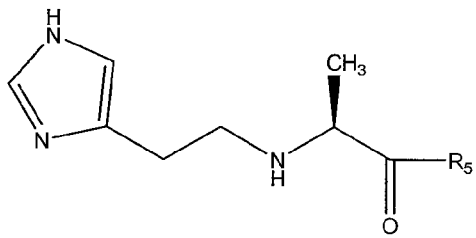
Figure 14N
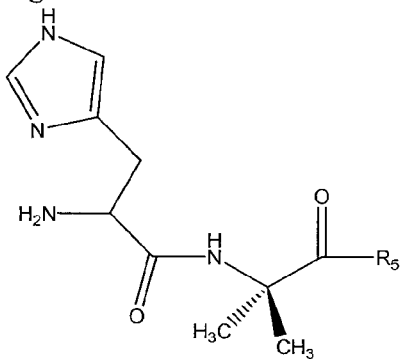
Figure 14O
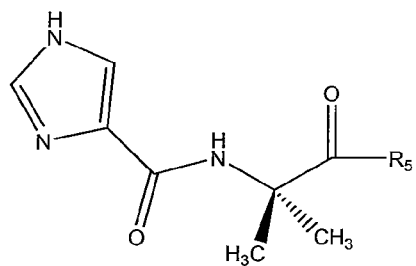
Figure 14P
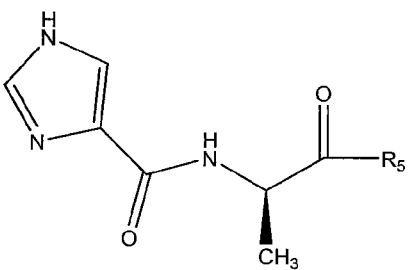
Figure 14Q
[βAla²]-exendin-4-NH₂
Figure 14R
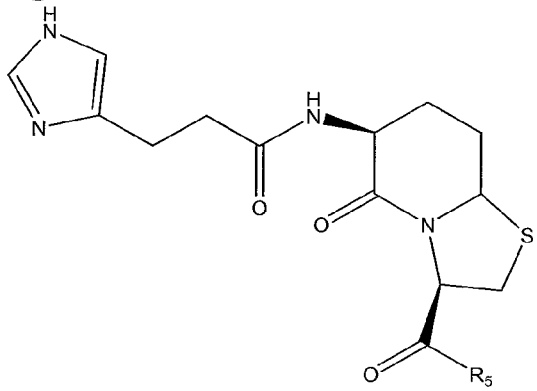

SEQUENCE LISTING

```
<160> NUMBER OF SEQ ID NOS: 122

<210> SEQ ID NO 1
<211> LENGTH: 28
<212> TYPE: PRT
<213> ORGANISM: Artificial Sequence
<220> FEATURE:
<223> OTHER INFORMATION: Formula (B); Description of Artificial
      Sequence: Synthetic polypeptide
<220> FEATURE:
<221> NAME/KEY: MISC_FEATURE
<222> LOCATION: (1)..(1)
<223> OTHER INFORMATION: A compound of Formula (1); see specification as
      filed for detailed description
<220> FEATURE:
<221> NAME/KEY: MISC_FEATURE
<222> LOCATION: (2)..(2)
<223> OTHER INFORMATION: see specification as filed for detailed
      description of substitutions and preferred embodiments
<220> FEATURE:
<221> NAME/KEY: MISC_FEATURE
<222> LOCATION: (3)..(3)
<223> OTHER INFORMATION: see specification as filed for detailed
      description of substitutions and preferred embodiments
<220> FEATURE:
<221> NAME/KEY: MISC_FEATURE
<222> LOCATION: (4)..(4)
<223> OTHER INFORMATION: Gly, D-Ala or Aib
<220> FEATURE:
<221> NAME/KEY: MISC_FEATURE
<222> LOCATION: (14)..(14)
<223> OTHER INFORMATION: Leu or Met
<220> FEATURE:
<221> NAME/KEY: MISC_FEATURE
<222> LOCATION: (25)..(25)
<223> OTHER INFORMATION: Phe or Trp
<220> FEATURE:
<221> NAME/KEY: MISC_FEATURE
<222> LOCATION: (28)..(28)
<223> OTHER INFORMATION: C termin is OH or NH2

<400> SEQUENCE: 1

Xaa Xaa Xaa Xaa Thr Phe Thr Ser Asp Leu Ser Lys Gln Xaa Glu Glu
1               5                   10                  15

Glu Ala Val Arg Leu Phe Ile Glu Xaa Leu Lys Asn
            20                  25

<210> SEQ ID NO 2
<211> LENGTH: 28
<212> TYPE: PRT
<213> ORGANISM: Artificial Sequence
<220> FEATURE:
<223> OTHER INFORMATION: Formula (C); Description of Artificial
      Sequence: Synthetic polypeptide
<220> FEATURE:
<221> NAME/KEY: MISC_FEATURE
<222> LOCATION: (1)..(1)
```

```
<223> OTHER INFORMATION: Compound of Formula (1); see specification as
      filed for detailed description and preferred embodiments
<220> FEATURE:
<221> NAME/KEY: MISC_FEATURE
<222> LOCATION: (2)..(2)
<223> OTHER INFORMATION: see specification as filed for detailed
      description of substitutions and preferred embodiments
<220> FEATURE:
<221> NAME/KEY: MISC_FEATURE
<222> LOCATION: (3)..(3)
<223> OTHER INFORMATION: see specification as filed for detailed
      description of substitutions and preferred embodiments
<220> FEATURE:
<221> NAME/KEY: MISC_FEATURE
<222> LOCATION: (4)..(4)
<223> OTHER INFORMATION: Gly; dAla; or Aib
<220> FEATURE:
<221> NAME/KEY: MISC_FEATURE
<222> LOCATION: (14)..(14)
<223> OTHER INFORMATION: Leu or Met
<220> FEATURE:
<221> NAME/KEY: MISC_FEATURE
<222> LOCATION: (25)..(25)
<223> OTHER INFORMATION: Phe or Trp
<220> FEATURE:
<221> NAME/KEY: MISC_FEATURE
<222> LOCATION: (28)..(28)
<223> OTHER INFORMATION: R10; see specification as filed for detailed
      description of substitutions and preferred embodiments
<220> FEATURE:
<221> NAME/KEY: MISC_FEATURE
<222> LOCATION: (28)..(28)
<223> OTHER INFORMATION: C term. is OH or NH2

<400> SEQUENCE: 2

Xaa Xaa Xaa Xaa Thr Phe Thr Ser Asp Leu Ser Lys Gln Xaa Glu Glu
1               5                   10                  15

Glu Ala Val Arg Leu Phe Ile Glu Xaa Leu Lys Xaa
            20                  25

<210> SEQ ID NO 3
<211> LENGTH: 39
<212> TYPE: PRT
<213> ORGANISM: Artificial Sequence
<220> FEATURE:
<223> OTHER INFORMATION: Formula (D); Description of Artificial
      Sequence: Synthetic polypeptide
<220> FEATURE:
<221> NAME/KEY: MISC_FEATURE
<223> OTHER INFORMATION: C term is OH or NH2
<220> FEATURE:
<221> NAME/KEY: MISC_FEATURE
<222> LOCATION: (1)..(1)
<223> OTHER INFORMATION: A compound of Formula (1); see specification as
      filed for detailed description and preferred embodiments
<220> FEATURE:
<221> NAME/KEY: MISC_FEATURE
<222> LOCATION: (2)..(2)
<223> OTHER INFORMATION: see specification as filed for detailed
      description of substitutions and preferred embodiments
<220> FEATURE:
<221> NAME/KEY: MISC_FEATURE
<222> LOCATION: (3)..(3)
<223> OTHER INFORMATION: see specification as filed for detailed
      description of substitutions and preferred embodiments
<220> FEATURE:
<221> NAME/KEY: MISC_FEATURE
<222> LOCATION: (4)..(4)
<223> OTHER INFORMATION: Gly; dALA; or Aib
<220> FEATURE:
<221> NAME/KEY: MISC_FEATURE
<222> LOCATION: (14)..(14)
<223> OTHER INFORMATION: Leu or Met
<220> FEATURE:
<221> NAME/KEY: MISC_FEATURE
<222> LOCATION: (25)..(25)
<223> OTHER INFORMATION: Phe or Trp
```

```
<220> FEATURE:
<221> NAME/KEY: MISC_FEATURE
<222> LOCATION: (28)..(28)
<223> OTHER INFORMATION: C term is OH or NH2

<400> SEQUENCE: 3

Xaa Xaa Xaa Xaa Thr Phe Thr Ser Asp Leu Ser Lys Gln Xaa Glu Glu
1               5                   10                  15

Glu Ala Val Arg Leu Phe Ile Glu Xaa Leu Lys Asn Gly Gly Pro Ser
            20                  25                  30

Ser Gly Ala Pro Pro Ser
        35

<210> SEQ ID NO 4
<211> LENGTH: 31
<212> TYPE: PRT
<213> ORGANISM: Artificial Sequence
<220> FEATURE:
<223> OTHER INFORMATION: Formula (E); Description of Artificial
      Sequence: Synthetic polypeptide
<220> FEATURE:
<221> NAME/KEY: MISC_FEATURE
<222> LOCATION: (1)..(1)
<223> OTHER INFORMATION: A compound of Formula (1); see specification as
      filed for detailed description and preferred embodiments
<220> FEATURE:
<221> NAME/KEY: MISC_FEATURE
<222> LOCATION: (2)..(2)
<223> OTHER INFORMATION: see specification as filed for detailed
      description of substitutions and preferred embodiments
<220> FEATURE:
<221> NAME/KEY: MISC_FEATURE
<222> LOCATION: (3)..(3)
<223> OTHER INFORMATION: see specification as filed for detailed
      description of substitutions and preferred embodiments
<220> FEATURE:
<221> NAME/KEY: MISC_FEATURE
<222> LOCATION: (4)..(4)
<223> OTHER INFORMATION: Gly; dAla; or Aib
<220> FEATURE:
<221> NAME/KEY: MISC_FEATURE
<222> LOCATION: (14)..(14)
<223> OTHER INFORMATION: Leu or Met
<220> FEATURE:
<221> NAME/KEY: MISC_FEATURE
<222> LOCATION: (25)..(25)
<223> OTHER INFORMATION: Phe or Trp
<220> FEATURE:
<221> NAME/KEY: MISC_FEATURE
<222> LOCATION: (28)..(28)
<223> OTHER INFORMATION: Lys or Arg
<220> FEATURE:
<221> NAME/KEY: MISC_FEATURE
<222> LOCATION: (31)..(31)
<223> OTHER INFORMATION: Gly or absent
<220> FEATURE:
<221> NAME/KEY: MISC_FEATURE
<222> LOCATION: (31)..(31)
<223> OTHER INFORMATION: C term. is OH or NH2

<400> SEQUENCE: 4

Xaa Xaa Xaa Xaa Thr Phe Thr Ser Asp Val Ser Ser Tyr Xaa Glu Gly
1               5                   10                  15

Gln Ala Ala Lys Glu Phe Ile Ala Xaa Leu Val Xaa Gly Arg Xaa
            20                  25                  30

<210> SEQ ID NO 5
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 5

Gly Thr Phe Thr Ser Asp Leu Ser Lys Gln Leu Glu Glu Glu Ala Val
1               5                   10                  15

Arg Leu Phe Ile Glu Trp Leu Lys Gln Gly Gly Pro Ser Lys Glu Ile
            20                  25                  30

Ile Ser

<210> SEQ ID NO 6
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Thr Phe Thr Ser Asp Leu Ser Lys Gln Leu Glu Glu Glu Ala Val
1               5                   10                  15

Arg Leu Phe Ile Glu Phe Leu Lys Asn
            20                  25

<210> SEQ ID NO 7
<211> LENGTH: 27
<212> TYPE: PRT
<213> ORGANISM: Artificial Sequence
<220> FEATURE:
<223> OTHER INFORMATION: R4; Description of Artificial Sequence:
      Synthetic polypeptide; see specification as filed for detailed
      description of substitutions and preferred embodiments
<220> FEATURE:
<221> NAME/KEY: MISC_FEATURE
<222> LOCATION: (1)..(1)
<223> OTHER INFORMATION: Gly, D-Ala or Aib
<220> FEATURE:
<221> NAME/KEY: MISC_FEATURE
<222> LOCATION: (2)..(2)
<223> OTHER INFORMATION: Glu or Pro
<220> FEATURE:
<221> NAME/KEY: MISC_FEATURE
<222> LOCATION: (27)..(27)
<223> OTHER INFORMATION: C term. is NH2

<400> SEQUENCE: 7

Xaa Xaa Gly Thr Phe Thr Ser Asp Leu Ser Lys Gln Leu Glu Glu Glu
1               5                   10                  15

Ala Val Arg Leu Phe Ile Glu Phe Leu Lys Asn
            20                  25

<210> SEQ ID NO 8
<211> LENGTH: 38
<212> TYPE: PRT
<213> ORGANISM: Artificial Sequence
<220> FEATURE:
<223> OTHER INFORMATION: R4; Description of Artificial Sequence:
      Synthetic polypeptide; see specification as filed for detailed
      description of substitutions and preferred embodiments
<220> FEATURE:
<221> NAME/KEY: MISC_FEATURE
<222> LOCATION: (1)..(1)
<223> OTHER INFORMATION: Gly, D-Ala, Aib; or not Gly when Xaa2 is Glu.
      see specification as filed for detailed description of
      substitutions and preferred embodiments.
<220> FEATURE:
<221> NAME/KEY: MISC_FEATURE
<222> LOCATION: (2)..(2)
<223> OTHER INFORMATION: Glu, Pro; or not Glu when Xaa1 is Gly; see
      specification as filed for detailed description of substitutions
      and preferred embodiments
<220> FEATURE:
```

```
<221> NAME/KEY: MISC_FEATURE
<222> LOCATION: (38)..(38)
<223> OTHER INFORMATION: C term. is NH2

<400> SEQUENCE: 8

Xaa Xaa Gly Thr Phe Thr Ser Asp Leu Ser Lys Gln Leu Glu Glu
1               5                   10                  15

Ala Val Arg Leu Phe Ile Glu Trp Leu Lys Asn Gly Gly Pro Ser Ser
            20                  25                  30

Gly Ala Pro Pro Pro Ser
        35

<210> SEQ ID NO 9
<211> LENGTH: 36
<212> TYPE: PRT
<213> ORGANISM: Artificial Sequence
<220> FEATURE:
<223> OTHER INFORMATION: R4; Description of Artificial Sequence:
      Synthetic polypeptide; see specification as filed for detailed
      description of substitutions and preferred embodiments
<220> FEATURE:
<221> NAME/KEY: MISC_FEATURE
<222> LOCATION: (1)..(1)
<223> OTHER INFORMATION: Gly, D-Ala or Aib
<220> FEATURE:
<221> NAME/KEY: MISC_FEATURE
<222> LOCATION: (2)..(2)
<223> OTHER INFORMATION: Glu or Pro

<400> SEQUENCE: 9

Xaa Xaa Gly Thr Phe Thr Ser Asp Leu Ser Lys Gln Leu Glu Glu
1               5                   10                  15

Ala Val Arg Leu Phe Ile Glu Trp Leu Lys Gln Gly Gly Pro Ser Lys
            20                  25                  30

Glu Ile Ile Ser
        35

<210> SEQ ID NO 10
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Glu Gly Thr Phe Thr Ser Asp Leu Ser Lys Gln Leu Glu Glu
1               5                   10                  15

Ala Val Arg Leu Phe Ile Glu Trp Leu Lys Asn Gly Gly Pro Ser Ser
            20                  25                  30

Gly Ala Pro Pro Pro Ser
        35

<210> SEQ ID NO 11
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gly Thr Phe Thr Ser Asp Leu Ser Lys Gln Leu Glu Glu Glu Ala Val
1               5                   10                  15

Arg Leu Phe Ile Glu Trp Leu Lys Asn Gly Gly Pro Ser Ser Gly Ala
            20                  25                  30
```

```
Pro Pro Pro Ser
        35

<210> SEQ ID NO 12
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Pro Gly Thr Phe Thr Ser Asp Leu Ser Lys Gln Leu Glu Glu Glu Ala
1               5                   10                  15

Val Arg Leu Phe Ile Glu Trp Leu Lys Asn Gly Gly Pro Ser Ser Gly
            20                  25                  30

Ala Pro Pro Pro Ser
        35

<210> SEQ ID NO 13
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Phe Thr Ser Asp Leu Ser Lys Gln Leu Glu Glu Glu Ala Val Arg Leu
1               5                   10                  15

Phe Ile Glu Trp Leu Lys Gln Gly Gly Pro Ser Lys Glu Ile Ile Ser
            20                  25                  30

<210> SEQ ID NO 14
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Phe Thr Ser Asp Leu Ser Lys Gln Leu Glu Glu Glu Ala Val Arg Leu
1               5                   10                  15

Phe Ile Glu Trp Leu Lys Asn Gly Gly Pro Ser Ser Gly Ala Pro Pro
            20                  25                  30

Pro Ser

<210> SEQ ID NO 15
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Thr Ser Asp Val Ser Ser Tyr Leu Glu Gly Gln Ala Ala Lys Glu
1               5                   10                  15

Phe Ile Ala Trp Leu Val Lys Gly Arg Gly
            20                  25

<210> SEQ ID NO 16
<211> LENGTH: 39
```

```
<212> TYPE: PRT
<213> ORGANISM: Heloderma horridum

<400> SEQUENCE: 16

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Glu Gly Thr
1

<210> SEQ ID NO 18
<211> LENGTH: 24
<212> TYPE: PRT
<213> ORGANISM: Artificial Sequence
<220> FEATURE:
<223> OTHER INFORMATION: Z; Description of Artificial Sequence:
      Synthetic peptide; see specification as filed for detailed
      description and preferred embodiments
<220> FEATURE:
<221> NAME/KEY: MISC_FEATURE
<222> LOCATION: (10)..(10)
<223> OTHER INFORMATION: Leu or Met
<220> FEATURE:
<221> NAME/KEY: MISC_FEATURE
<222> LOCATION: (21)..(21)
<223> OTHER INFORMATION: Phe or Trp
<220> FEATURE:
<221> NAME/KEY: MISC_FEATURE
<222> LOCATION: (24)..(24)
<223> OTHER INFORMATION: Z1: C term. is OH or NH2.

<400> SEQUENCE: 18

Thr Phe Thr Ser Asp Leu Ser Lys Gln Xaa Glu Glu Glu Ala Val Arg
1               5                   10                  15

Leu Phe Ile Glu Xaa Leu Lys Asn
            20

<210> SEQ ID NO 19
<211> LENGTH: 35
<212> TYPE: PRT
<213> ORGANISM: Artificial Sequence
<220> FEATURE:
<223> OTHER INFORMATION: Z; Description of Artificial Sequence:
      Synthetic peptide; see specification as filed for detailed
      description and preferred embodiments
<220> FEATURE:
<221> NAME/KEY: MISC_FEATURE
<222> LOCATION: (10)..(10)
<223> OTHER INFORMATION: Leu or Met
<220> FEATURE:
<221> NAME/KEY: MISC_FEATURE
<222> LOCATION: (21)..(21)
<223> OTHER INFORMATION: Phe or Trp
<220> FEATURE:
<221> NAME/KEY: MISC_FEATURE
<222> LOCATION: (35)..(35)
<223> OTHER INFORMATION: Z1; C term is OH or NH2
```

-continued

```
<400> SEQUENCE: 19

Thr Phe Thr Ser Asp Leu Ser Lys Gln Xaa Glu Glu Glu Ala Val Arg
1               5                   10                  15

Leu Phe Ile Glu Xaa Leu Lys Asn Gly Gly Pro Ser Ser Gly Ala Pro
            20                  25                  30

Pro Pro Ser
        35

<210> SEQ ID NO 20
<211> LENGTH: 24
<212> TYPE: PRT
<213> ORGANISM: Artificial Sequence
<220> FEATURE:
<223> OTHER INFORMATION: Z; Description of Artificial Sequence:
      Synthetic peptide; see specification as filed for detailed
      description and preferred embodiments
<220> FEATURE:
<221> NAME/KEY: MOD_RES
<222> LOCATION: (10)..(10)
<223> OTHER INFORMATION: Leu or Met
<220> FEATURE:
<221> NAME/KEY: MOD_RES
<222> LOCATION: (21)..(21)
<223> OTHER INFORMATION: Phe or Trp
<220> FEATURE:
<221> NAME/KEY: MISC_FEATURE
<222> LOCATION: (24)..(24)
<223> OTHER INFORMATION: Z1; C term is OH or NH2

<400> SEQUENCE: 20

Thr Phe Thr Ser Asp Leu Ser Lys Gln Xaa Glu Glu Glu Ala Val Arg
1               5                   10                  15

Leu Phe Ile Glu Xaa Leu Lys Xaa
            20

<210> SEQ ID NO 21
<211> LENGTH: 27
<212> TYPE: PRT
<213> ORGANISM: Artificial Sequence
<220> FEATURE:
<223> OTHER INFORMATION: Z; Description of Artificial Sequence:
      Synthetic peptide; see specification as filed for detailed
      description and preferred embodiments
<220> FEATURE:
<221> NAME/KEY: MISC_FEATURE
<222> LOCATION: (10)..(10)
<223> OTHER INFORMATION: Leu or Met
<220> FEATURE:
<221> NAME/KEY: MISC_FEATURE
<222> LOCATION: (21)..(21)
<223> OTHER INFORMATION: Phe or Trp
<220> FEATURE:
<221> NAME/KEY: MISC_FEATURE
<222> LOCATION: (24)..(24)
<223> OTHER INFORMATION: Lys or Arg
<220> FEATURE:
<221> NAME/KEY: MISC_FEATURE
<222> LOCATION: (27)..(27)
<223> OTHER INFORMATION: Gly or absent
<220> FEATURE:
<221> NAME/KEY: MISC_FEATURE
<222> LOCATION: (27)..(27)
<223> OTHER INFORMATION: Z1; C term is OH or NH2

<400> SEQUENCE: 21

Thr Phe Thr Ser Asp Val Ser Ser Tyr Xaa Glu Gly Gln Ala Ala Lys
1               5                   10                  15

Glu Phe Ile Ala Xaa Leu Val Xaa Gly Arg Xaa
            20                  25
```

-continued

```
<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Gly Gly Pro Ser Lys Glu Ile Ile Ser
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Gly Gly Pro Ser Ser Gly Ala Pro Pro Pro Ser
1               5                   10

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asn Gly Gly Pro
1

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asn Gly Gly Pro Ser
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asn Gly Gly Pro Ser Ser
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27
```

```
Asn Gly Gly Pro Ser Ser Gly
1               5
```

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Asn Gly Gly Pro Ser Ser Gly Ala
1               5
```

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Asn Gly Gly Pro Ser Ser Gly Ala Pro
1               5
```

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Asn Gly Gly Pro Ser Ser Gly Ala Pro Pro
1               5                   10
```

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Asn Gly Gly Pro Ser Ser Gly Ala Pro Pro
1               5                   10
```

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Asn Gly Gly Pro Ser Ser Gly Ala Pro Pro Ser
1               5                   10
```

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic

```
                                  -continued peptide

<400> SEQUENCE: 33

Asn Gly Gly Pro Ser Ser Gly Ala Pro Pro Ser Lys
1               5                   10

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (12)..(17)
<223> OTHER INFORMATION: This region may encompass 2 to 6 "Lys" residues

<400> SEQUENCE: 34

Asn Gly Gly Pro Ser Ser Gly Ala Pro Pro Ser Lys Lys Lys Lys Lys
1               5                   10                  15

Lys

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asn Gly Gly Pro Ser Ser Gly Ala Pro Pro Pro Ser Lys
1               5                   10

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

His Gly Glu Gly
1

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

His Ala Glu Gly
1

<210> SEQ ID NO 38
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
```

-continued

<223> OTHER INFORMATION: Beta-Ala

<400> SEQUENCE: 38

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 39
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gly Glu Gly Thr Phe Thr Ser Asp Leu Ser Lys Gln Met Glu Glu Glu
1               5                   10                  15

Ala Val Arg Leu Phe Ile Glu Trp Leu Lys Asn Gly Gly Pro Ser Ser
            20                  25                  30

Gly Ala Pro Pro Pro Ser
        35

<210> SEQ ID NO 40
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

His Gly Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 41
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

His Gly Pro Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 42
<211> LENGTH: 39
<212> TYPE: PRT
<213> ORGANISM: Artificial Sequence
<220> FEATURE:
<223> OTHER INFORMATION: Description of Artificial Sequence: Synthetic

```
                                    polypeptide

<400> SEQUENCE: 42

His Gly Pro Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Ser
        35

<210> SEQ ID NO 43
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

His Gly Pro Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 44
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

His Gly Pro Gly Thr Phe Thr Ser Asp Leu Ser Lys Gln Leu Glu Glu
1               5                   10                  15

Glu Ala Val Arg Leu Phe Ile Glu Trp Leu Lys Asn
            20                  25

<210> SEQ ID NO 45
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

His Gly Pro Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 46
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

His Gly Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30
```

Ser Gly Ala Pro
        35

<210> SEQ ID NO 47
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

His Gly Pro Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro
        35

<210> SEQ ID NO 48
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

His Gly Pro Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro
        35

<210> SEQ ID NO 49
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

His Gly Pro Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser
        35

<210> SEQ ID NO 50
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

His Ser Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

```
Ser Gly Ala Pro Pro Ser
        35

<210> SEQ ID NO 51
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

His Gly Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly
            20                  25

<210> SEQ ID NO 52
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

His Gly Pro Gly Thr Phe Thr Ser Asp Leu Ser Lys Gln Leu Glu Glu
1               5                   10                  15

Glu Ala Val Arg Leu Phe Ile Glu Phe Leu Lys Asn Gly
            20                  25

<210> SEQ ID NO 53
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

His Gly Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 54
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

His Gly Pro Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly
            20                  25                  30

<210> SEQ ID NO 55
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 55

His Gly Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro
            20                  25                  30

<210> SEQ ID NO 56
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

His Gly Pro Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

His Gly Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

His Gly Pro Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

<210> SEQ ID NO 59
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

His Gly Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser
```

```
<210> SEQ ID NO 60
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

His Gly Pro Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser

<210> SEQ ID NO 61
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

His Gly Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly

<210> SEQ ID NO 62
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

His Gly Pro Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly

<210> SEQ ID NO 63
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

His Gly Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 64
<211> LENGTH: 35
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 64

His Gly Pro Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala
        35

<210> SEQ ID NO 65
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

His Gly Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro
        35

<210> SEQ ID NO 66
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

His Gly Pro Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro
        35

<210> SEQ ID NO 67
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

His Gly Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro
        35

<210> SEQ ID NO 68
<211> LENGTH: 38
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 68

His Gly Pro Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro
        35

<210> SEQ ID NO 69
<211> LENGTH: 39
<212> TYPE: PRT
<213> ORGANISM: Artificial Sequence
<220> FEATURE:
<223> OTHER INFORMATION: Compound 24B; Description of Artificial
      Sequence: Synthetic polypeptide
<220> FEATURE:
<221> NAME/KEY: MISC_FEATURE
<222> LOCATION: (1)..(1)
<223> OTHER INFORMATION: 4-imidazoproprionyl
<220> FEATURE:
<221> NAME/KEY: MOD_RES
<222> LOCATION: (27)..(27)
<223> OTHER INFORMATION: Lys(biotin)
<220> FEATURE:
<221> NAME/KEY: MOD_RES
<222> LOCATION: (39)..(39)
<223> OTHER INFORMATION: Lys[(NH2)(biotin)]

<400> SEQUENCE: 69

Xaa Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys
        35

<210> SEQ ID NO 70
<211> LENGTH: 29
<212> TYPE: PRT
<213> ORGANISM: Artificial Sequence
<220> FEATURE:
<223> OTHER INFORMATION: Compound 24C; Description of Artificial
      Sequence: Synthetic peptide
<220> FEATURE:
<221> NAME/KEY: MISC_FEATURE
<222> LOCATION: (1)..(1)
<223> OTHER INFORMATION: 4-imidazopropionyl
<220> FEATURE:
<221> NAME/KEY: MISC_FEATURE
<222> LOCATION: (29)..(29)
<223> OTHER INFORMATION: Lys[(NH2)(biotin)]

<400> SEQUENCE: 70

Xaa Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Lys
            20                  25

<210> SEQ ID NO 71
<211> LENGTH: 29
<212> TYPE: PRT
<213> ORGANISM: Artificial Sequence
<220> FEATURE:
<223> OTHER INFORMATION: Compound 24D; Description of Artificial
```

```
          Sequence: Synthetic peptide
<220> FEATURE:
<221> NAME/KEY: MISC_FEATURE
<222> LOCATION: (1)..(1)
<223> OTHER INFORMATION: 4-imidazopropionyl
<220> FEATURE:
<221> NAME/KEY: MISC_FEATURE
<222> LOCATION: (29)..(29)
<223> OTHER INFORMATION: Lys[(NH2)(biotin)]

<400> SEQUENCE: 71

Xaa Ala Pro Gly Thr Phe Thr Ser Asp Leu Ser Lys Gln Met Glu Glu
1               5                   10                  15

Glu Ala Val Arg Leu Phe Ile Glu Trp Leu Lys Asn Lys
            20                  25

<210> SEQ ID NO 72
<211> LENGTH: 39
<212> TYPE: PRT
<213> ORGANISM: Artificial Sequence
<220> FEATURE:
<223> OTHER INFORMATION: Compound 10J; Description of Artificial
      Sequence: Synthetic polypeptide
<220> FEATURE:
<221> NAME/KEY: MISC_FEATURE
<222> LOCATION: (1)..(1)
<223> OTHER INFORMATION: 4-imidazopropionyl
<220> FEATURE:
<221> NAME/KEY: MISC_FEATURE
<222> LOCATION: (39)..(39)
<223> OTHER INFORMATION: C term amidation

<400> SEQUENCE: 72

Xaa Gly Pro Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 73
<211> LENGTH: 39
<212> TYPE: PRT
<213> ORGANISM: Artificial Sequence
<220> FEATURE:
<223> OTHER INFORMATION: Compound 10L; Description of Artificial
      Sequence: Synthetic polypeptide
<220> FEATURE:
<221> NAME/KEY: MISC_FEATURE
<222> LOCATION: (1)..(1)
<223> OTHER INFORMATION: 4-imidazopropionyl
<220> FEATURE:
<221> NAME/KEY: MISC_FEATURE
<222> LOCATION: (2)..(2)
<223> OTHER INFORMATION: Aib
<220> FEATURE:
<221> NAME/KEY: MISC_FEATURE
<222> LOCATION: (39)..(39)
<223> OTHER INFORMATION: C term amidation

<400> SEQUENCE: 73

Xaa Xaa Pro Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 74
```

```
<211> LENGTH: 37
<212> TYPE: PRT
<213> ORGANISM: Artificial Sequence
<220> FEATURE:
<223> OTHER INFORMATION: Compound 10M; Description of Artificial
      Sequence: Synthetic polypeptide
<220> FEATURE:
<221> NAME/KEY: MISC_FEATURE
<222> LOCATION: (1)..(1)
<223> OTHER INFORMATION: 4-imidazopropionyl

<400> SEQUENCE: 74

Xaa Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser
        35

<210> SEQ ID NO 75
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

His Gly Pro Gly Thr Phe Thr Ser Asp Leu Ser Lys Gln Leu Glu Glu
1               5                   10                  15

Glu Ala Val Arg Leu Phe Ile Glu Trp Leu Lys Asn Gly
            20                  25

<210> SEQ ID NO 76
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

His Gly Pro Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly
            20                  25                  30

<210> SEQ ID NO 77
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

His Gly Pro Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro
            20                  25                  30

<210> SEQ ID NO 78
<211> LENGTH: 32
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 78

His Gly Pro Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

<210> SEQ ID NO 79
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

His Gly Pro Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser

<210> SEQ ID NO 80
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

His Gly Pro Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly

<210> SEQ ID NO 81
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

His Gly Pro Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 82
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

His Gly Pro Gly Thr Phe Thr Ser Asp Leu Ser Lys Gln Leu Glu Glu

```
                 1               5                  10                 15

Glu Ala Val Arg Leu Phe Ile Glu Trp Leu Lys Asn Gly Gly Pro Ser
                20                  25                 30

Ser Gly Ala Pro Pro
        35

<210> SEQ ID NO 83
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

His Gly Pro Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
                20                  25                 30

Ser Gly Ala Pro Pro Pro
        35

<210> SEQ ID NO 84
<211> LENGTH: 31
<212> TYPE: PRT
<213> ORGANISM: Homo sapiens

<400> SEQUENCE: 84

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
                20                  25                 30

<210> SEQ ID NO 85
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
                20                  25                 30

<210> SEQ ID NO 86
<211> LENGTH: 39
<212> TYPE: PRT
<213> ORGANISM: Heloderma suspectum

<400> SEQUENCE: 86

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                 30

Ser Gly Ala Pro Pro Pro Ser
        35

<210> SEQ ID NO 87
<211> LENGTH: 37
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 87

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser
        35

<210> SEQ ID NO 88
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

His Ala Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 89
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

His Gly Pro Ala Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 90
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

His Ala Pro Ala Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 91
<211> LENGTH: 39
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 91

His Val Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 92
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: NMeAla

<400> SEQUENCE: 92

His Ala Leu Ala Pro Gly Thr Phe Thr Ser Asp Leu Ser Lys Gln Met
1               5                   10                  15

Glu Glu Glu Ala Val Arg Leu Phe Ile Glu Trp Leu Lys Asn Gly Gly
            20                  25                  30

Pro Ser Ser Gly Ala Pro Pro Pro Ser
        35                  40

<210> SEQ ID NO 93
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 94
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Pro Gly Thr Phe Thr Ser Asp Leu Ser Lys Gln Leu Glu Glu Glu Ala
1               5                   10                  15

Val Arg Leu Phe Ile Glu Phe Leu Lys Asn
            20                  25

<210> SEQ ID NO 95
<211> LENGTH: 28
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 95

His Val Pro Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 96
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

His Ala Pro Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 97
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

His Cys Pro Cys Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 98
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

His Cys Pro Cys Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser
        35

<210> SEQ ID NO 99
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn

```
                        20                  25

<210> SEQ ID NO 100
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Thr Phe Thr Ser Asp Leu Ser Lys Gln Leu Glu Glu Glu Ala Val Arg
1               5                   10                  15

Leu Phe Ile Glu Phe Leu Lys Asn
            20

<210> SEQ ID NO 101
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Glu Gly Thr Phe Thr Ser Asp Leu Ser Lys Gln Leu Glu Glu Glu
1               5                   10                  15

Ala Val Arg Leu Phe Ile Glu Trp Leu Lys Asn
            20                  25

<210> SEQ ID NO 102
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Thr Phe Thr Ser Asp Leu Ser Lys Gln Leu Glu Glu Glu Ala Val
1               5                   10                  15

Arg Leu Phe Ile Glu Trp Leu Lys Asn
            20                  25

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Pro Gly Thr Phe Thr Ser Asp Leu
1               5

<210> SEQ ID NO 104
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Thr Ser Asp Leu Ser Lys Gln Leu Glu Glu Glu Ala Val Arg Leu Phe
1               5                   10                  15
```

```
Ile Glu Phe Leu Lys Asn
            20

<210> SEQ ID NO 105
<211> LENGTH: 39
<212> TYPE: PRT
<213> ORGANISM: Artificial Sequence
<220> FEATURE:
<223> OTHER INFORMATION: Compound 23A
<220> FEATURE:
<221> NAME/KEY: MISC_FEATURE
<222> LOCATION: (1)..(1)
<223> OTHER INFORMATION: 4-imidazopropionyl
<220> FEATURE:
<221> NAME/KEY: MISC_FEATURE
<222> LOCATION: (2)..(2)
<223> OTHER INFORMATION: dAla
<220> FEATURE:
<221> NAME/KEY: MISC_FEATURE
<222> LOCATION: (12)..(12)
<223> OTHER INFORMATION: Lys at position 12 is modified with
      -C(=O)-CH2(OCH2CH2)2NH-C(=O)CH2-(OCH2CH2)2NH-C(=O)-(CH2)6-CH3
<220> FEATURE:
<221> NAME/KEY: MISC_FEATURE
<222> LOCATION: (39)..(39)
<223> OTHER INFORMATION: C term amidation

<400> SEQUENCE: 105

Xaa Xaa Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 106
<211> LENGTH: 39
<212> TYPE: PRT
<213> ORGANISM: Artificial Sequence
<220> FEATURE:
<223> OTHER INFORMATION: Compound 23B
<220> FEATURE:
<221> NAME/KEY: MISC_FEATURE
<222> LOCATION: (1)..(1)
<223> OTHER INFORMATION: 4-imidazopropionyl
<220> FEATURE:
<221> NAME/KEY: MISC_FEATURE
<222> LOCATION: (2)..(2)
<223> OTHER INFORMATION: d-Ala
<220> FEATURE:
<221> NAME/KEY: MISC_FEATURE
<222> LOCATION: (12)..(12)
<223> OTHER INFORMATION: Lys at position 12 is modified with
      -C(=O)-CH2(OCH2CH2)2NH-C(=O)CH2-(OCH2CH2)2NH-C(=O)-CH(NH2)-
      (CH2)7-CH3
<220> FEATURE:
<221> NAME/KEY: MISC_FEATURE
<222> LOCATION: (39)..(39)
<223> OTHER INFORMATION: C term amidation

<400> SEQUENCE: 106

Xaa Xaa Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 107
<211> LENGTH: 39
```

```
<212> TYPE: PRT
<213> ORGANISM: Artificial Sequence
<220> FEATURE:
<223> OTHER INFORMATION: Compound 23C
<220> FEATURE:
<221> NAME/KEY: MISC_FEATURE
<222> LOCATION: (1)..(1)
<223> OTHER INFORMATION: 4-imidazopropionyl
<220> FEATURE:
<221> NAME/KEY: MISC_FEATURE
<222> LOCATION: (2)..(2)
<223> OTHER INFORMATION: d-Ala
<220> FEATURE:
<221> NAME/KEY: MISC_FEATURE
<222> LOCATION: (12)..(12)
<223> OTHER INFORMATION: Lys at position 12 is modified with
     -C(=O)-CH2(OCH2CH2)2NH-C(=O)CH2-(OCH2CH2)2NH-C(=O)-CH[NH-
     C(=O)(CH2)6CH3]-(CH2)7-CH3
<220> FEATURE:
<221> NAME/KEY: MISC_FEATURE
<222> LOCATION: (39)..(39)
<223> OTHER INFORMATION: C term amidation

<400> SEQUENCE: 107

Xaa Xaa Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 108
<211> LENGTH: 39
<212> TYPE: PRT
<213> ORGANISM: Artificial Sequence
<220> FEATURE:
<223> OTHER INFORMATION: Compound 23D
<220> FEATURE:
<221> NAME/KEY: MISC_FEATURE
<222> LOCATION: (1)..(1)
<223> OTHER INFORMATION: 4-imidazopropionyl
<220> FEATURE:
<221> NAME/KEY: MISC_FEATURE
<222> LOCATION: (2)..(2)
<223> OTHER INFORMATION: dAla
<220> FEATURE:
<221> NAME/KEY: MISC_FEATURE
<222> LOCATION: (12)..(12)
<223> OTHER INFORMATION: Lys at position 12 is modified with
     -C(=O)-CH2(OCH2CH2)2NH-C(=O)CH2-(OCH2CH2)2NH-C(=O)-CH2CH2-
     CH[C(OH)(=O)]-NH-C(=O)-(CH2)16-[C(OH)(=O)]
<220> FEATURE:
<221> NAME/KEY: MISC_FEATURE
<222> LOCATION: (39)..(39)
<223> OTHER INFORMATION: C term amidation

<400> SEQUENCE: 108

Xaa Xaa Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 109
<211> LENGTH: 39
<212> TYPE: PRT
<213> ORGANISM: Artificial Sequence
<220> FEATURE:
<223> OTHER INFORMATION: Compound 23E
<220> FEATURE:
<221> NAME/KEY: MISC_FEATURE
```

```
<222> LOCATION: (1)..(1)
<223> OTHER INFORMATION: 4-imidazopropionyl
<220> FEATURE:
<221> NAME/KEY: MISC_FEATURE
<222> LOCATION: (2)..(2)
<223> OTHER INFORMATION: dAla
<220> FEATURE:
<221> NAME/KEY: MISC_FEATURE
<222> LOCATION: (27)..(27)
<223> OTHER INFORMATION: Lys at position 27 is modified with
     -C(=O)-CH2(OCH2CH2)2NH-C(=O)CH2-(OCH2CH2)2NH-C(=O)-(CH2)6-CH3
<220> FEATURE:
<221> NAME/KEY: MISC_FEATURE
<222> LOCATION: (39)..(39)
<223> OTHER INFORMATION: C term amidation

<400> SEQUENCE: 109

Xaa Xaa Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 110
<211> LENGTH: 39
<212> TYPE: PRT
<213> ORGANISM: Artificial Sequence
<220> FEATURE:
<223> OTHER INFORMATION: Compound 23F
<220> FEATURE:
<221> NAME/KEY: MISC_FEATURE
<222> LOCATION: (1)..(1)
<223> OTHER INFORMATION: 4-imidazopropionyl
<220> FEATURE:
<221> NAME/KEY: MISC_FEATURE
<222> LOCATION: (2)..(2)
<223> OTHER INFORMATION: d-Ala
<220> FEATURE:
<221> NAME/KEY: MISC_FEATURE
<222> LOCATION: (27)..(27)
<223> OTHER INFORMATION: Lys at position 27 is modified with
     -C(=O)-CH2(OCH2CH2)2NH-C(=O)CH2-(OCH2CH2)2NH-C(=O)-CH(NH2)-
     (CH2)7-CH3
<220> FEATURE:
<221> NAME/KEY: MISC_FEATURE
<222> LOCATION: (39)..(39)
<223> OTHER INFORMATION: C term amidation

<400> SEQUENCE: 110

Xaa Xaa Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 111
<211> LENGTH: 39
<212> TYPE: PRT
<213> ORGANISM: Artificial Sequence
<220> FEATURE:
<223> OTHER INFORMATION: Compound 23G
<220> FEATURE:
<221> NAME/KEY: MISC_FEATURE
<222> LOCATION: (1)..(1)
<223> OTHER INFORMATION: 4-imidazopropionyl
<220> FEATURE:
<221> NAME/KEY: MISC_FEATURE
<222> LOCATION: (2)..(2)
<223> OTHER INFORMATION: d-Ala
<220> FEATURE:
```

```
<221> NAME/KEY: MISC_FEATURE
<222> LOCATION: (27)..(27)
<223> OTHER INFORMATION: Lys at position 27 is modified with
      -C(=O)-CH2(OCH2CH2)2NH-C(=O)CH2-(OCH2CH2)2NH-C(=O)-CH[NH-
      C(=O)(CH2)6CH3]-(CH2)7-CH3
<220> FEATURE:
<221> NAME/KEY: MISC_FEATURE
<222> LOCATION: (39)..(39)
<223> OTHER INFORMATION: C term amidation

<400> SEQUENCE: 111

Xaa Xaa Pro Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
             20                  25                  30

Ser Gly Ala Pro Pro Pro Ser
             35

<210> SEQ ID NO 112
<211> LENGTH: 39
<212> TYPE: PRT
<213> ORGANISM: Artificial Sequence
<220> FEATURE:
<223> OTHER INFORMATION: Compound 23G
<220> FEATURE:
<221> NAME/KEY: MISC_FEATURE
<222> LOCATION: (1)..(1)
<223> OTHER INFORMATION: 4-imidazopropionyl
<220> FEATURE:
<221> NAME/KEY: MISC_FEATURE
<222> LOCATION: (2)..(2)
<223> OTHER INFORMATION: dAla
<220> FEATURE:
<221> NAME/KEY: MISC_FEATURE
<222> LOCATION: (27)..(27)
<223> OTHER INFORMATION: Lys at position 12 is modified with
      -C(=O)-CH2(OCH2CH2)2NH-C(=O)CH2-(OCH2CH2)2NH-C(=O)-CH2CH2-
      CH[C(OH)(=O)]-NH-C(=O)-(CH2)16-[C(OH)(=O)]
<220> FEATURE:
<221> NAME/KEY: MISC_FEATURE
<222> LOCATION: (39)..(39)
<223> OTHER INFORMATION: C term amidation

<400> SEQUENCE: 112

Xaa Xaa Pro Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
             20                  25                  30

Ser Gly Ala Pro Pro Pro Ser
             35

<210> SEQ ID NO 113
<211> LENGTH: 39
<212> TYPE: PRT
<213> ORGANISM: Artificial Sequence
<220> FEATURE:
<223> OTHER INFORMATION: Compound 23I
<220> FEATURE:
<221> NAME/KEY: MISC_FEATURE
<222> LOCATION: (1)..(1)
<223> OTHER INFORMATION: 4-imidazopropionyl
<220> FEATURE:
<221> NAME/KEY: MISC_FEATURE
<222> LOCATION: (2)..(2)
<223> OTHER INFORMATION: dAla
<220> FEATURE:
<221> NAME/KEY: MISC_FEATURE
<222> LOCATION: (39)..(39)
<223> OTHER INFORMATION: S at position 39 is modified with
      -Lys(NHs)-C(=O)-CH2(OCH2CH2)2NH-C(=O)CH2-(OCH2CH2)2NH-C(=O)-
      (CH2)6-CH3
```

-continued

```
<400> SEQUENCE: 113

Xaa Xaa Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 114
<211> LENGTH: 39
<212> TYPE: PRT
<213> ORGANISM: Artificial Sequence
<220> FEATURE:
<223> OTHER INFORMATION: Compound 23J
<220> FEATURE:
<221> NAME/KEY: MISC_FEATURE
<222> LOCATION: (1)..(1)
<223> OTHER INFORMATION: 4-imidazoproprionyl
<220> FEATURE:
<221> NAME/KEY: MISC_FEATURE
<222> LOCATION: (2)..(2)
<223> OTHER INFORMATION: dAla
<220> FEATURE:
<221> NAME/KEY: MISC_FEATURE
<222> LOCATION: (39)..(39)
<223> OTHER INFORMATION: S at position 39 is modified with -Lys(NHs)
<220> FEATURE:
<221> NAME/KEY: MISC_FEATURE
<222> LOCATION: (39)..(39)
<223> OTHER INFORMATION: S at position 39 is modified with
      -Lys(NHs)-C(=O)-CH2(OCH2CH2)2NH-C(=O)CH2-(OCH2CH2)2NH-C(=O)-
      CH(NH2)-(CH2)7-CH3

<400> SEQUENCE: 114

Xaa Xaa Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 115
<211> LENGTH: 39
<212> TYPE: PRT
<213> ORGANISM: Artificial Sequence
<220> FEATURE:
<223> OTHER INFORMATION: Compound 23K
<220> FEATURE:
<221> NAME/KEY: MISC_FEATURE
<222> LOCATION: (1)..(1)
<223> OTHER INFORMATION: 4-imidazoproprionyl
<220> FEATURE:
<221> NAME/KEY: MISC_FEATURE
<222> LOCATION: (2)..(2)
<223> OTHER INFORMATION: dAla
<220> FEATURE:
<221> NAME/KEY: MISC_FEATURE
<222> LOCATION: (39)..(39)
<223> OTHER INFORMATION: S at position 39 is modified with -Lys(NHs)
<220> FEATURE:
<221> NAME/KEY: MISC_FEATURE
<222> LOCATION: (39)..(39)
<223> OTHER INFORMATION: S at position 39 is modified with
      -Lys(NHs)-C(=O)-CH2(OCH2CH2)2NH-C(=O)CH2-(OCH2CH2)2NH-C(=O)-
      CH[NH-C(=O)(CH2)6CH3]-(CH2)7-CH3

<400> SEQUENCE: 115

Xaa Xaa Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
```

-continued

```
                    20                  25                  30

Ser Gly Ala Pro Pro Ser
        35

<210> SEQ ID NO 116
<211> LENGTH: 39
<212> TYPE: PRT
<213> ORGANISM: Artificial Sequence
<220> FEATURE:
<223> OTHER INFORMATION: Compound 23L
<220> FEATURE:
<221> NAME/KEY: MISC_FEATURE
<222> LOCATION: (1)..(1)
<223> OTHER INFORMATION: 4-imidazopropionyl
<220> FEATURE:
<221> NAME/KEY: MISC_FEATURE
<222> LOCATION: (2)..(2)
<223> OTHER INFORMATION: dAla
<220> FEATURE:
<221> NAME/KEY: MISC_FEATURE
<222> LOCATION: (39)..(39)
<223> OTHER INFORMATION: S at position 39 is modified with -Lys(NHs)
<220> FEATURE:
<221> NAME/KEY: MISC_FEATURE
<222> LOCATION: (39)..(39)
<223> OTHER INFORMATION: S at position 39 is modified with
      -Lys(NHs)-C(=O)-CH2(OCH2CH2)2NH-C(=O)CH2-(OCH2CH2)2NH-C(=O)-
      CH2CH2-CH[C(OH)(=O)]-NH-C(=O)-(CH2)16-[C(OH)(=O)]

<400> SEQUENCE: 116

Xaa Xaa Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser
        35

<210> SEQ ID NO 117
<211> LENGTH: 39
<212> TYPE: PRT
<213> ORGANISM: Artificial Sequence
<220> FEATURE:
<223> OTHER INFORMATION: Compound 24A
<220> FEATURE:
<221> NAME/KEY: MISC_FEATURE
<222> LOCATION: (2)..(2)
<223> OTHER INFORMATION: dAla
<220> FEATURE:
<221> NAME/KEY: MISC_FEATURE
<222> LOCATION: (27)..(27)
<223> OTHER INFORMATION: Lys(biotin)
<220> FEATURE:
<221> NAME/KEY: MISC_FEATURE
<222> LOCATION: (39)..(39)
<223> OTHER INFORMATION: Lys[(NH2)(biotin)]

<400> SEQUENCE: 117

His Xaa Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Lys
        35

<210> SEQ ID NO 118
<211> LENGTH: 39
<212> TYPE: PRT
<213> ORGANISM: Artificial Sequence
<220> FEATURE:
<223> OTHER INFORMATION: Compound 24E
```

```
<220> FEATURE:
<221> NAME/KEY: MISC_FEATURE
<222> LOCATION: (2)..(2)
<223> OTHER INFORMATION: dAla
<220> FEATURE:
<221> NAME/KEY: MISC_FEATURE
<222> LOCATION: (39)..(39)
<223> OTHER INFORMATION: Lys(NH2)-(O-CH2-CH2)2-KAKAEAEAKAKAEAEA-biotin.

<400> SEQUENCE: 118

His Xaa Pro Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys
        35

<210> SEQ ID NO 119
<211> LENGTH: 27
<212> TYPE: PRT
<213> ORGANISM: Artificial Sequence
<220> FEATURE:
<223> OTHER INFORMATION: Compound 24F
<220> FEATURE:
<221> NAME/KEY: MISC_FEATURE
<222> LOCATION: (2)..(2)
<223> OTHER INFORMATION: dAla
<220> FEATURE:
<221> NAME/KEY: MISC_FEATURE
<222> LOCATION: (27)..(27)
<223> OTHER INFORMATION: E[-O-CH2-CH2)2-(biotin)]-NGGPSSGAPPPS-NH2

<400> SEQUENCE: 119

His Xaa Pro Gly Thr Phe Thr Ser Asp Leu Ser Lys Gln Met Glu Glu
1               5                   10                  15

Glu Ala Val Arg Leu Phe Ile Glu Trp Leu Glu
            20                  25

<210> SEQ ID NO 120
<211> LENGTH: 13
<212> TYPE: PRT
<213> ORGANISM: Artificial Sequence
<220> FEATURE:
<223> OTHER INFORMATION: Compound 24G
<220> FEATURE:
<221> NAME/KEY: MISC_FEATURE
<222> LOCATION: (2)..(2)
<223> OTHER INFORMATION: dAla
<220> FEATURE:
<221> NAME/KEY: MISC_FEATURE
<222> LOCATION: (13)..(13)
<223> OTHER INFORMATION: K-[-(O-CH2-CH2)2-(biotin)]-
      QMEEEAVRLFIEWLKNGGPSSGAPPPS-NH2

<400> SEQUENCE: 120

His Xaa Pro Gly Thr Phe Thr Ser Asp Leu Ser Glu Lys
1               5                   10

<210> SEQ ID NO 121
<211> LENGTH: 39
<212> TYPE: PRT
<213> ORGANISM: Artificial Sequence
<220> FEATURE:
<223> OTHER INFORMATION: Compound 10K
<220> FEATURE:
<221> NAME/KEY: MISC_FEATURE
<222> LOCATION: (1)..(1)
<223> OTHER INFORMATION: 4-imidazopropionyl
<220> FEATURE:
<221> NAME/KEY: MISC_FEATURE
<222> LOCATION: (2)..(2)
```

```
<223> OTHER INFORMATION: dAla
<220> FEATURE:
<221> NAME/KEY: MISC_FEATURE
<222> LOCATION: (39)..(39)
<223> OTHER INFORMATION: C term amidation

<400> SEQUENCE: 121

Xaa Xaa Pro Gly Thr Phe Thr Ser Asp Leu Ser Lys Gln Leu Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 122
<211> LENGTH: 37
<212> TYPE: PRT
<213> ORGANISM: Artificial Sequence
<220> FEATURE:
<223> OTHER INFORMATION: Compound 10N
<220> FEATURE:
<221> NAME/KEY: MISC_FEATURE
<222> LOCATION: (1)..(1)
<223> OTHER INFORMATION: 4-imidazopropionyl
<220> FEATURE:
<221> NAME/KEY: MISC_FEATURE
<222> LOCATION: (2)..(2)
<223> OTHER INFORMATION: dAla

<400> SEQUENCE: 122

Xaa Xaa Pro Gly Thr Phe Thr Ser Asp Leu Ser Lys Gln Leu Glu Glu
 1               5                  10                  15

Glu Ala Val Arg Leu Phe Ile Glu Trp Leu Lys Gln Gly Gly Pro Ser
            20                  25                  30

Lys Glu Ile Ile Ser
        35
```

N-TERMINUS CONFORMATIONALLY CONSTRAINED GLP-1 RECEPTOR AGONIST COMPOUNDS

RELATED APPLICATIONS

This is a §371 application of PCT/US2010/028883, with an international filing date of Mar. 26, 2010, which claims benefit of priority from U.S. Ser. No. 61/165,604, filed Apr. 1, 2009, both of which are incorporated by reference in their entirety, including all tables, figures and claims.

FIELD

Provided herein are N-terminus conformationally constrained GLP-1 receptor agonist compounds and therapeutic methods for their use.

BACKGROUND

Peptides and proteins play critical roles in the regulation of biological processes. Peptides, for example, play a regulatory role as hormones and inhibitors, and are also involved in immunological recognition. The significant biological role of peptides makes it important to understand their interactions with the receptors to which they bind.

The determination of the receptor-bound conformation of a peptide is invaluable for the rational design of peptide analogs. Marshall et al, *Ann. Rep. Med. Chem.*, 13:227-238 (1978) disclose that peptides are characteristically highly flexible molecules, the structures of which are strongly influenced by the environment in which they reside. Thus, peptides are not generally useful for determining their receptor-bound conformation.

As no approach is available to predict which new ligand-receptor interactions will lead to antagonists and which will lead to agonists of greater or less potency, it is necessary to perform classical structure-function studies in a systematic way to provide information about the specific amino acid residues and functional groups in a peptide that are important to biological activity. Studies of this nature can utilize conformationally constrained peptide mimetics. For example, Hruby, *Trends Pharmacol. Sci.*, 8:336-339 (1987) suggests that conformational constraints can provide information about the different requirements that a receptor has for a ligand to be an agonist or antagonist.

Generally, peptide mimetics can be defined as structures which serve as appropriate substitutes for peptides in interactions with receptors and enzymes. The development of rational approaches for discovering peptide mimetics is a major goal of medicinal chemistry. Such development has been attempted both by empirical screening approaches and by specific synthetic design. Specific design of peptide mimetics has utilized both peptide backbone modifications and chemical mimics of peptide secondary structures. The beta-turn has been implicated as an important site for molecular recognition in many biologically active peptides. Consequently, peptides containing conformationally constrained mimetics of beta-turns are particularly desirable.

There is a need in the art for new GLP-1 receptor agonist compounds that have good stability, resistance to degradation, and good glucagon-like peptide-1 (GLP-1) receptor binding activity and in vivo glucose lowering activity. To solve these needs, the disclosure herein provides, among other things, novel N-terminus conformationally constrained compounds, novel N-terminus conformationally constrained GLP-1 receptor agonist compounds containing modifications, such as peptide mimetics and/or amino acid substitutions, that provide a conformationally constrained N-terminus that results in improved GLP-1 receptor binding and in vivo blood glucose lowering activity.

SUMMARY

It was previously believed that the N-terminus of exendin-4 and exendin analogs was a random coil. It has now been unexpectedly discovered that the N-terminus shows a high beta-turn characteristic in a specific site, and therefore mimics the receptor bound conformation of this region of the peptides. The disclosure herein is based on this discovery.

Provided herein are N-terminus conformationally constrained compounds having the formula: $Xaa_1Xaa_2Xaa_3$-Z and $Xaa_1Xaa_2Xaa_3Xaa_4$-Z, where the substituents are defined herein. These N-terminus conformationally constrained compounds may induce a β-turn conformational constraint at the N-terminus when they are used in GLP-1 receptor agonist compounds. The N-terminus conformationally constrained compounds may be used for therapeutic purposes (e.g., treat diabetes); for research purposes; and to produce GLP-1 receptor agonist compounds having improved GLP-1 receptor binding activity, enzymatic stability, and improved in vivo glucose lowering activity. The disclosure provides pharmaceutical compositions comprising therapeutically effective amounts of the N-terminus conformationally constrained compounds. The disclosure also provides methods for synthesizing the N-terminus conformationally constrained compounds.

Provided herein are GLP-1 receptor agonist compounds, such as exendins, exendin analogs, GLP-1(7-37), and GLP-1(7-37) analogs, comprising an N-terminus conformationally constrained compound having the formula $Xaa_1Xaa_2Xaa_3$- or $Xaa_1Xaa_2Xaa_3Xaa_4$-, where the substituents are defined herein. In one embodiment, the GLP-1 receptor agonist compounds comprise $Xaa_1Xaa_2Xaa_3Xaa_4$, where the substituents are defined herein, at positions 1-4 at the N-terminus. In one embodiment, the GLP-1 receptor agonist compounds comprise $Xaa_1Xaa_2Xaa_3$, where the substituents are defined herein, at positions 1-3 at the N-terminus. The disclosure provides pharmaceutical compositions comprising therapeutically effective amounts of these N-terminus conformationally-constrained GLP-1 receptor agonist compounds.

Provided herein are exendins and exendin analogs having the formula:

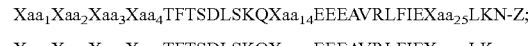
$Xaa_1Xaa_2Xaa_3Xaa_4TFTSDLSKQXaa_{14}EEEAVRLFIEXaa_{25}LKN$-Z;

$Xaa_1Xaa_2Xaa_3Xaa_4TFTSDLSKQXaa_{14}EEEAVRLFIEXaa_{25}LK$-$R_{10}$-Z;

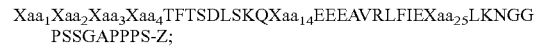
$Xaa_1Xaa_2Xaa_3Xaa_4TFTSDLSKQXaa_{14}EEEAVRLFIEXaa_{25}LKNGG$ PSSGAPPPS-Z;

where $Xaa_{14}$, $Xaa_{25}$, $R_{10}$, and Z are defined herein; and at least one of $Xaa_1$, $Xaa_2$, $Xaa_3$, and $Xaa_4$ are modifications, such as peptide mimetics and/or amino acid substitutions, that induce a conformational constraint at the N-terminus. The disclosure provides pharmaceutical compositions comprising therapeutically effective amounts of these exendin analogs.

Provided herein are GLP-1(7-37) and GLP-1(7-37) analogs having the formula:

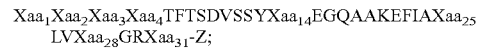
$Xaa_1Xaa_2Xaa_3Xaa_4TFTSDVSSYXaa_{14}EGQAAKEFIAXaa_{25}$ $LVXaa_{28}GRXaa_{31}$-Z;

where $Xaa_{14}$, $Xaa_{25}$, $Xaa_{28}$, $Xaa_{31}$, and Z are as defined herein; and at least one of $Xaa_1$, $Xaa_2$, $Xaa_3$, and $Xaa_4$ are modifications, such as peptide mimetics and/or amino acid substitutions, that induce a conformational constraint at the N-terminus. The disclosure provides pharmaceutical compositions comprising therapeutically effective amounts of these GLP-1(7-37) analogs.

Provided herein are GLP-1 receptor agonist compounds, such as exendins, exendin analogs, GLP-1(7-37), and GLP-1(7-37) analogs wherein position 1 comprises an imidazole ring (e.g., His) and position 3 is proline; where the GLP-1 receptor agonist compounds bind in a RIN cell membrane receptor binding assay with an affinity of less than 1 nM (or less than 0.1 nM).

The disclosure provides methods for treating diabetes; treating insulin resistance; treating postprandial hyperglycemia; lowering blood glucose levels; lowering HbA1c levels; stimulating insulin release; reducing gastric motility; delaying gastric emptying; reducing food intake; reducing appetite; reducing weight; treating overweight; and treating obesity in patients in need by administering therapeutically effective amounts of the N-terminus conformationally constrained compounds and/or the N-terminus conformationally constrained GLP-1 receptor agonist compounds described herein.

BRIEF DESCRIPTION OF THE FIGURES

FIG. 1: FIG. 1A is exendin-4 amide; FIG. 1B is dAla$^2$,Pro$^3$-exendin-4 amide, and FIG. 1C is dAla$^2$,Pro$^3$,Leu$^{14}$,Phe$^{25}$-exendin-4 (1-28) amide.

FIG. 2: FIG. 2A is an exendin analog, described, e.g., in WO 2007/139941. FIGS. 2L-2U show N-terminus conformationally constrained compounds. FIGS. 2B-J provide examples of exendin analogs containing the N-terminus conformationally constrained compounds shown in FIGS. 2L-2U.

FIGS. 3A-G are dAla$^2$,Pro$^3$-exendin-4 (FIG. 3A), Ala$^2$,Pro$^3$-exendin-4 (FIG. 3B), Pro$^3$,Ala$^4$-exendin-4 (FIG. 3C), Ala$^2$,Pro$^3$,Ala$^4$-exendin-4 (FIG. 3D), Pro$^3$,dAla$^4$-exendin-4 (FIG. 3E), Val$^2$,Pro$^3$-exendin-4 (FIG. 3F), and NMeAla$^2$,Pro$^3$-exendin-4 (FIG. 3G). The compound in FIGS. 1B and 3A are the same.

FIG. 5: FIG. 5A is Leu$^{14}$,Phe$^{25}$-exendin-4(1-28), described in WO 2007/139941. Leu$^{14}$,Phe$^{25}$-exendin-4(1-28) refers to amino acid residues 1-28 in exendin-4 (i.e., exendin-4(1-28), where the amino acid residue at position 14 in exendin-4 is replaced with Leu (i.e., Leu$^{14}$), and the amino acid residue at position 25 is replaced with Phe (i.e., Phe$^{25}$). FIGS. 5B-G show the exendin analog of FIG. 5A having a modification at Glu$^3$ or Gly$^2$Glu$^3$ at the N-terminus. R$_4$ is GTFTSDLSKQLEEEAVRLFIEFLKN-NH$_2$.

FIGS. 6A-E show the exendin analog of FIG. 5A having a modification at Gly$^2$Glu$^3$ or Gly$^2$Glu$^3$Gly$^4$ at the N-terminus. The C-terminal amino acid in each compound shown in FIGS. 6A-E is amidated.

FIG. 8.

FIG. 9.

FIG. 16.

FIG. 17.

FIG. 18.

FIG. 19.

FIG. 20.

FIG. 21.

DETAILED DESCRIPTION

Figure 1D:
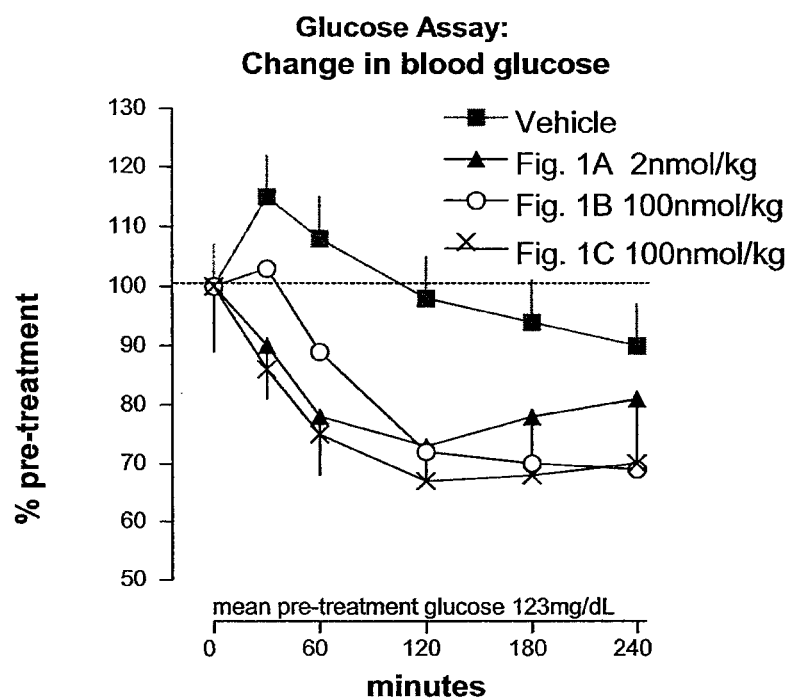
FIG. 1D is a graph showing the change in blood glucose in mice administered the compounds shown in FIGS. 1A-C based on the in vivo blood glucose assay described in Example 17. The compounds were injected IP at t=0 immediately following a baseline sample in 2-hour fasted NIH/Swiss mice. Blood glucose samples were taken at t=30, 60, 120, 180, and 240 minutes with a ONETOUCH® ULTRA® (LifeScan, Inc., Milpitas, Calif.).
Figure 2B:
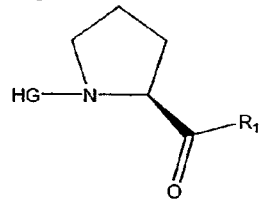
FIGS. 2B-J show the exendin analog of FIG. 2A having a modification at Glu$^3$. R$_1$ is GTFTSDL-SKQLEEEAVRLFIEWLKQGGPSKEIIS-NH$_2$.
Figure 2C:
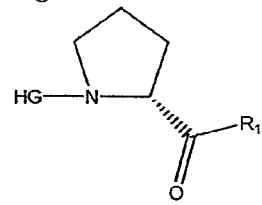
Figure 2D:
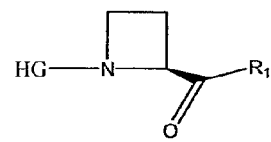
Figure 2E:
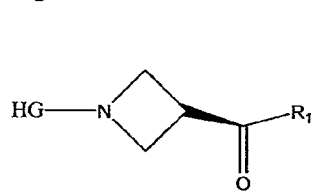
Figure 2F:
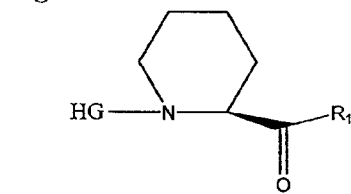
Figure 2G:
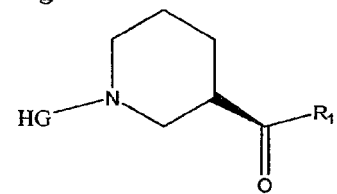
Figure 2H:
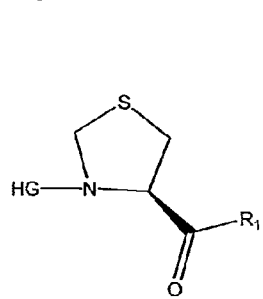
Figure 2I:
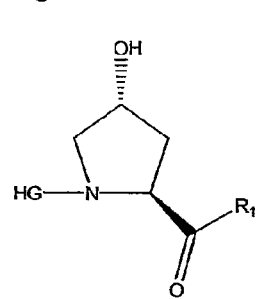
Figure 2J:
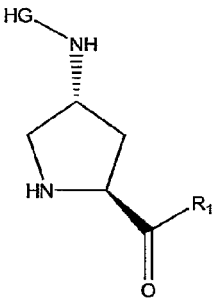
Figure 2K:
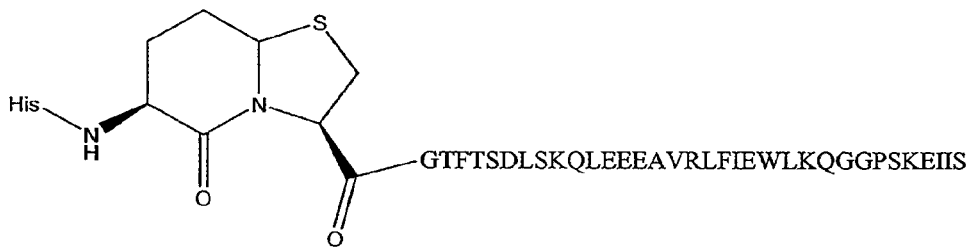
FIG. 2K shows the exendin analog of FIG. 2A having modifications at Gly$^2$Glu$^3$.
Figure 2L:
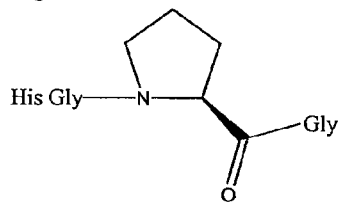
Figure 2M:
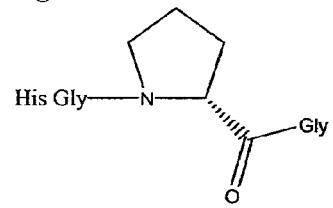
Figure 4:
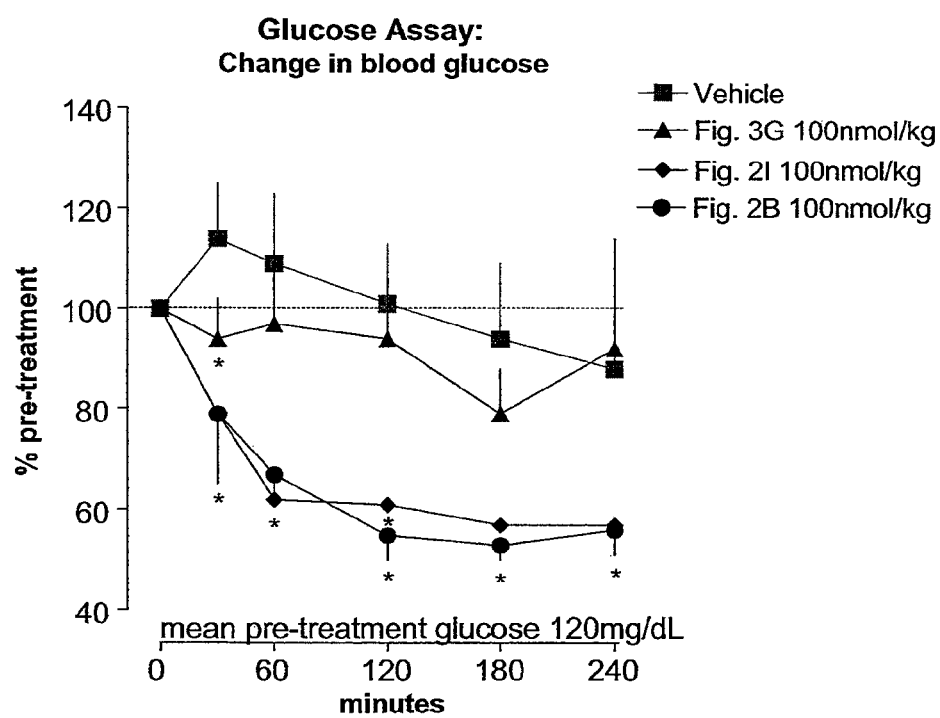
FIG. 4 is a graph showing the change in blood glucose in mice administered the compounds shown in FIGS. 3G, 2I, and 2B based on the in vivo blood glucose assay described in Example 17. The compounds were injected IP at t=0 immediately following a baseline sample in 2-hour fasted NIH/Swiss mice. Blood glucose samples were taken at t=30, 60, 120, 180, and 240 minutes with a ONETOUCH® ULTRA® (LifeScan, Inc., Milpitas, Calif.).
Figure 7:
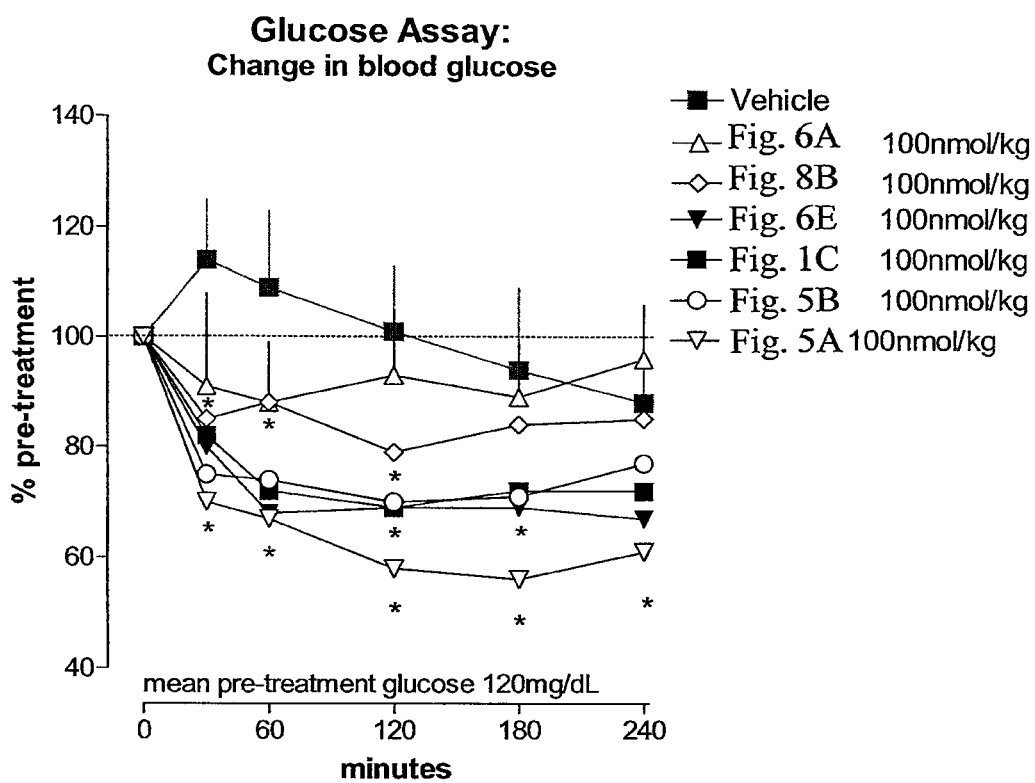
FIG. 7 is a graph showing the change in blood glucose in mice administered the compounds shown in FIGS. 6A, 8B, 6E, 1C, 5B, and 5A based on the in vivo blood glucose assay described in Example 17. The compounds were injected IP at t=0 immediately following a baseline sample in 2-hour fasted NIH/Swiss mice. Blood glucose samples were taken at t=30, 60, 120, 180, and 240 minutes with a ONETOUCH® ULTRA® (LifeScan, Inc., Milpitas, Calif.).
Figure 8A:
FIGS. 8A-D show the exendin analog in FIG. 5A having modifications at Gly$^2$Glu$^3$Gly$^4$ at the N-terminus, where the C-terminal amino acid is amidated.
Figure 8B:
Figure 8C:
Figure 8D:
Figure 8E:
FIGS. 8E-H show the exendin analog in FIG. 2A having modifications at Gly$^2$Glu$^3$Gly$^4$ at the N-terminus.
Figure 8F:
Figure 8G:
Figure 8H:
Figure 9A:
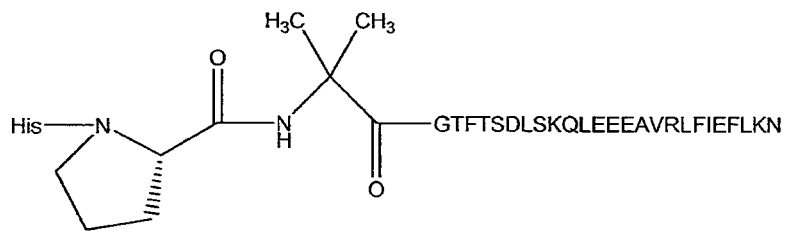
FIGS. 9A-H show the exendin analog in FIG. 5A having a modification at Gly$^2$Glu$^3$ or Gly$^2$Glu$^3$Gly$^4$ at the N-terminus. Each compound in FIGS. 9A-H is amidated at the C-terminal amino acid.
Figure 9B:
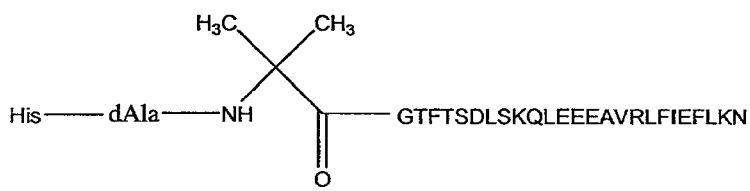
Figure 9C:
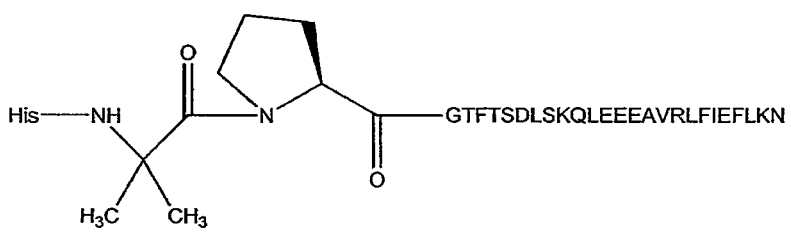
Figure 9D:
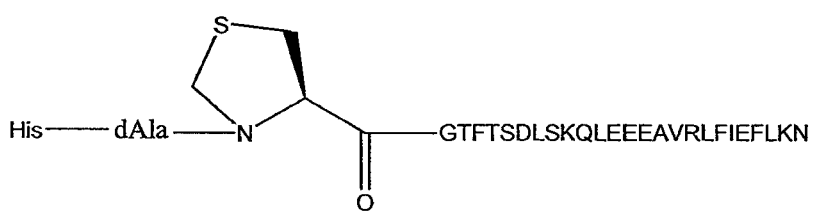
Figure 9E:
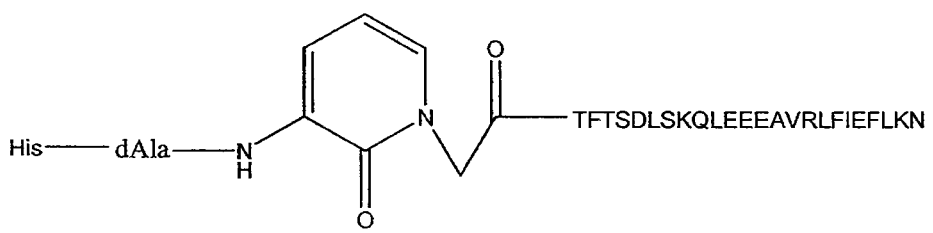
Figure 9F:
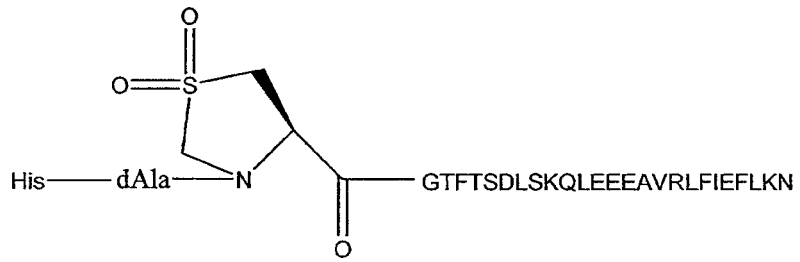
Figure 9G:
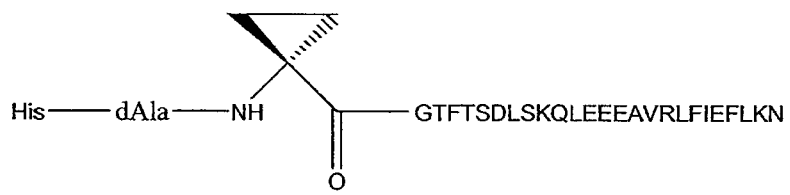
Figure 9H:
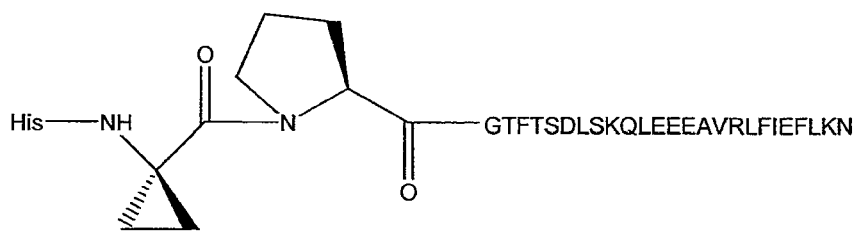
Figure 9I:
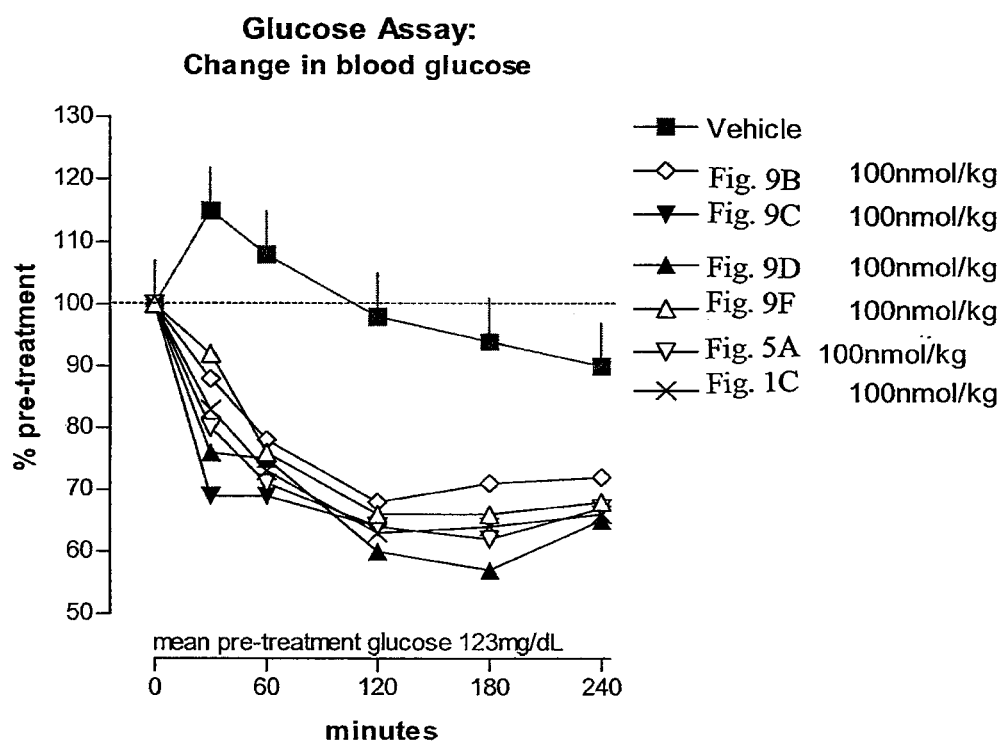
FIG. 9I is a graph showing the change in blood glucose in mice administered the compounds shown in FIGS. 9B, 9C, 9D, 9F, 5A, and 1C based on the in vivo blood glucose assay described in Example 17. The compounds were injected IP at t=0 immediately following a baseline sample in 2-hour fasted NIH/Swiss mice. Blood glucose samples were taken at t=30, 60, 120, 180, and 240 minutes with a ONETOUCH® ULTRA® (LifeScan, Inc., Milpitas, Calif.).
Figure 10A:
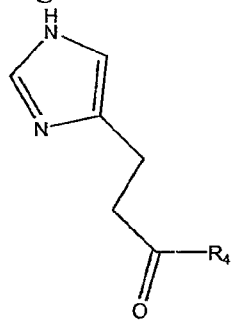
FIGS. 10A-I show the exendin analog in FIG. 5A having a modification at His$^1$ at the N-terminus. R$_4$ is Xaa$_2$Xaa$_3$GTFTSDLSKQLEEEAVRLFIEFLKN-NH$_2$, where Xaa$_2$ is Gly, dAla, or Aib; and Xaa$_3$ is Glu or Pro. Alternatively, R$_4$ is Xaa$_2$Xaa$_3$GTFTSDLSKQLEEEA VRLFIEWLKNGGPSS-GAPPPS-NH$_2$, where Xaa$_2$ is Gly, dAla, or Aib; and Xaa$_3$ is Glu or Pro; provided that Xaa$_3$ is not Glu when Xaa$_2$ is Gly, or Xaa$_2$ is not Gly when Xaa$_3$ is Glu. Alternatively, R$_4$ is Xaa$_2$Xaa$_3$GTFTSDLSKQLEEEAVRLFIEWLKQGGPSKE IIS-OH, where Xaa$_2$ is Gly, dAla, or Aib; and Xaa$_3$ is Glu or Pro.
Figure 10B:
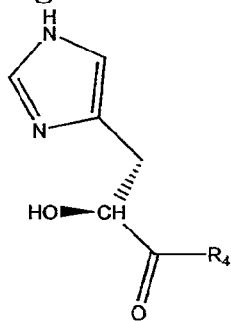
Figure 10C:
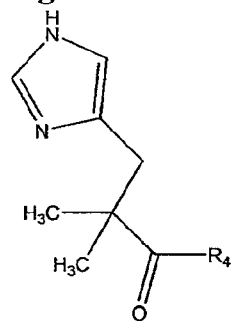
Figure 10D:
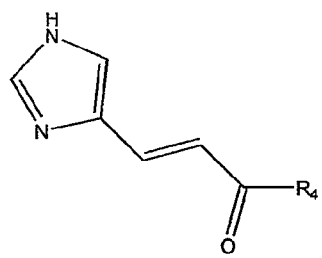
Figure 10E:
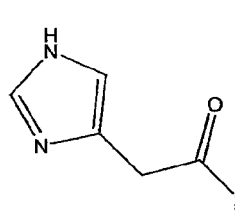
Figure 10F:
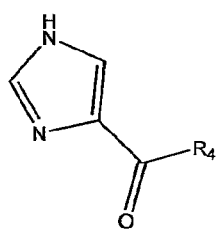
Figure 10G:
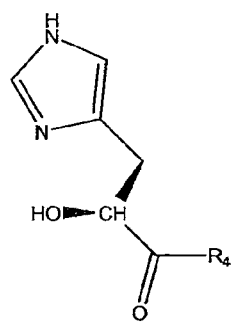
Figure 10H:
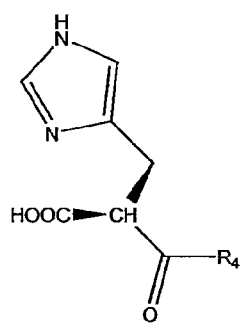
Figure 10I:
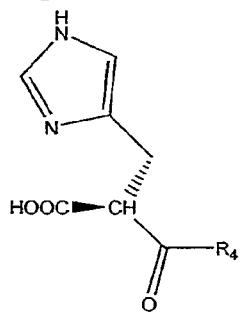
Figure 11A:
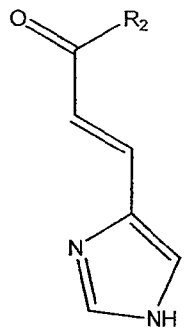
FIGS. 11A-B show exendin-4 of FIG. 1A having a modification at His$^1$ at the N-terminus. R$_2$ is GEGTFTSDL-SKQLEEEAVRLFIEWLKNGGPSSGAPPPS-NH$_2$.
Figure 11B:
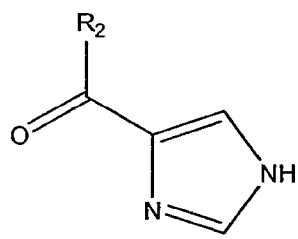
Figure 12:
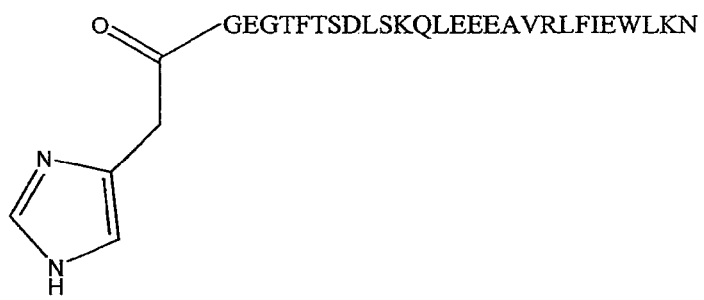
FIG. 12 shows the compound of FIG. 10E with an amino acid substitution of Trp$^{25}$. The compound in FIG. 12 is amidated at the C-terminal amino acid residue.
Figure 13:
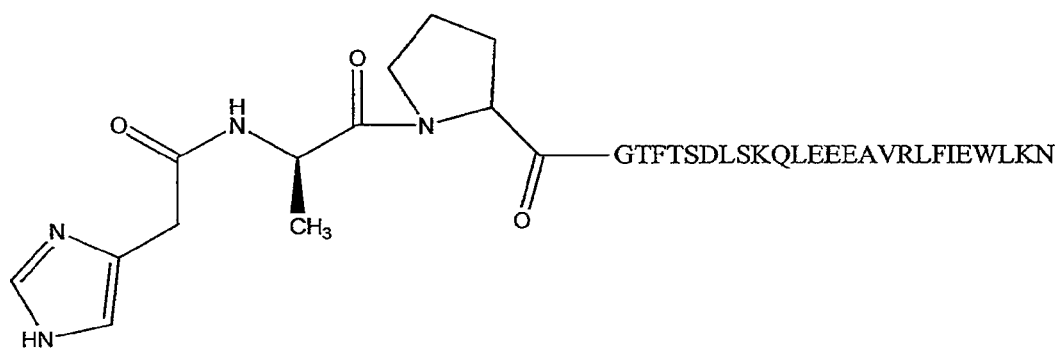
FIG. 13 shows an exendin analog having a modification at His$^1$Gly$^2$Glu$^3$. The compound in FIG. 13 is amidated at the C-terminal amino acid residue.
Figure 14A:
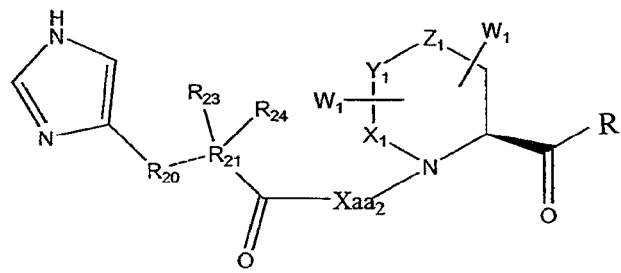
FIG. 14A is a generic structure (where Xaa$_2$ is, e.g., Gly, dAla, or Aib; and the other substituents are defined herein) of an exendin analog of FIG. 1A, 2A, or 5A having modifications at His$^1$Gly$^2$Glu$^3$ at the N-terminus, where R is a peptide, such as any one of the following: GTFTSDL-SKQLEEEAVRLFIEFLKN-NH$_2$; GTFTSDL-SKQLEEEAV-RLFIEWLKQGGPSKEIIS-OH; or GTFTS-DLSKQLEEEAVRLFIEWLKNGGPSSGAPPPS-NH$_2$. Aib is α-methylalanine.
Figure 14B:
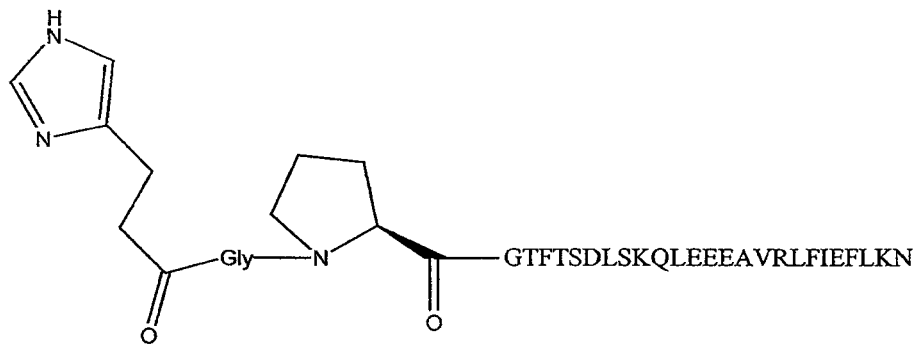
FIGS. 14B-C are examples of compounds from the structure in FIG. 14A that have modifications at His$^1$ and Glu$^3$. The compounds in FIGS. 14B-C are amidated at the C-terminal amino acid residue.
Figure 14C:
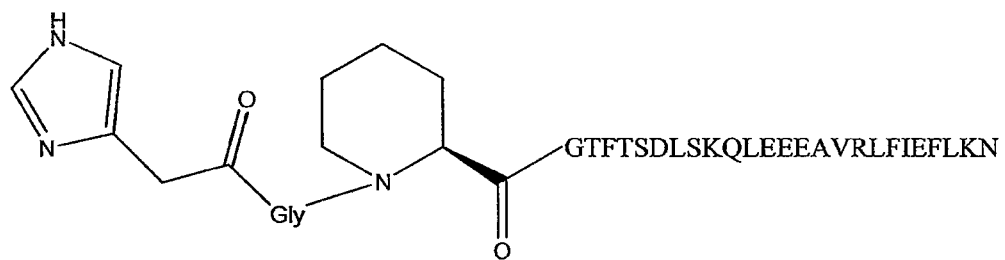
Figure 14D:
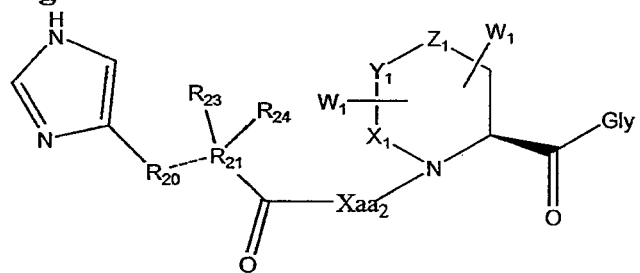
FIG. 14D provides the generic structure (where Xaa$_2$ is Gly, dAla, or Aib; and the other substituents are defined herein) of an N-terminus conformationally constrained compound.
Figure 14E:
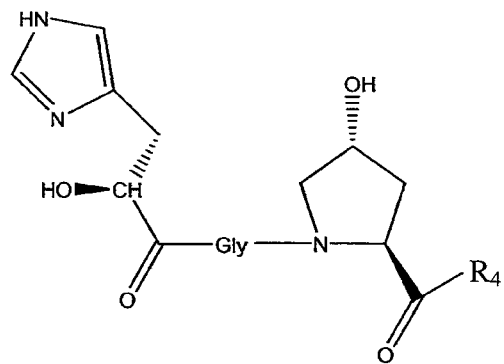
FIGS. 14E-R are exendin analogs comprising an N-terminus conformationally constrained compound. R$_1$ is GTFTSDL-SKQLEEEAVRLF IEWLKQGGPSKEIIS-OH. R$_4$ is GTFTSDLSKQLEEEAVRLFIEFLKN-NH$_2$. R$_5$ is PGT-FTSDLSKQLEEEAVRLFIEWLKNGGPSSGAPPPS-NH$_2$.
Figure 14F:
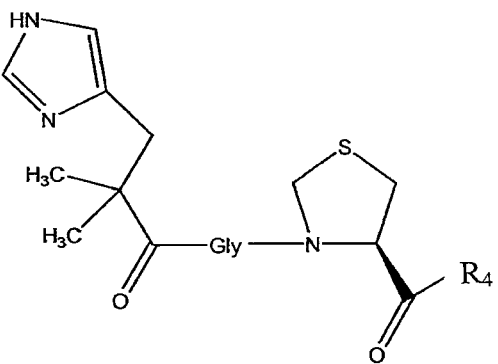
FIG. 14.
Figure 15A:
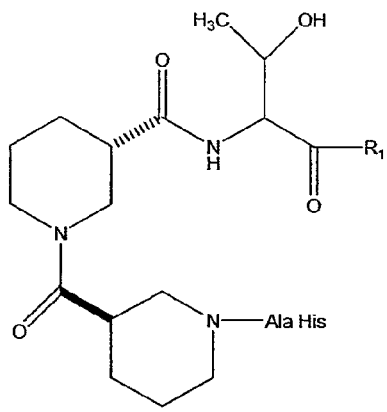
FIGS. 15A-D are exendin analogs that comprise isomers of nipecotic acid as the N-terminus conformationally constrained compound. R$_1$ is FTSDLSKQLEEEAVRLFI EWLKQGGPSKEIIS-NH$_2$.
Figure 15B:
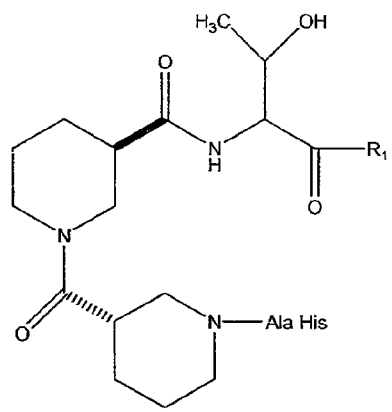
Figure 15C:
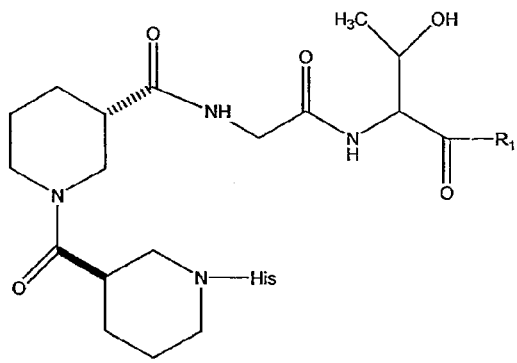
Figure 15D:
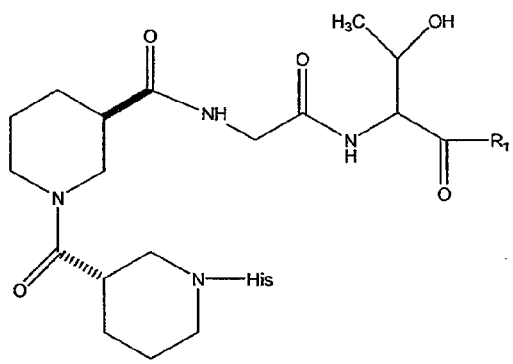

"GLP-1 receptor agonist compounds" refer to compounds that elicit a biological activity of an exendin reference peptide (e.g., exendin-4) or a GLP-1(7-37) reference peptide when evaluated by art-known measures such as receptor binding studies or in vivo blood glucose assays as described, e.g., Examples 16 and 17, and by Hargrove et al, *Regulatory Peptides,* 141:113-119 (2007), the disclosure of which is incorporated by reference herein. GLP-1 receptor agonist compounds include, for example, native exendins, exendin analogs, native GLP-1, GLP-1 analogs, GLP-1(7-37), and GLP-1(7-37) analogs.

The term "exendin" includes naturally occurring (or synthetic versions of naturally occurring) exendin peptides that are found in the salivary secretions of the Gila monster. Exendin-3 (HSDGTFTSDLSKQMEEEAVR-LFIEWLKNGGPSSGAPPPS-NH$_2$) is present in the salivary secretions of *Heloderma horridum* and exendin-4 (FIG. 1A) is present in the salivary secretions of *Heloderma suspectum*. Exendins include the amidated forms, the acid form, the pharmaceutically acceptable salt form, and any other physiologically active form of the molecule. In one embodiment, the term exendin can be used interchangeably with the term "exendin agonist."

"Exendin analog" refers to peptides, peptides containing peptide mimetics, amino acid substitutions, and/or other modifications, peptides containing the N-terminus conformationally constrained compounds described herein, and/or other chemical moieties, or other compounds which elicit a biological activity similar to that of an exendin reference peptide (e.g., exendin-4), when evaluated by art-known measures such as receptor binding assays or in vivo blood glucose assays as described, e.g., Examples 16 and 17, and by Hargrove et al, *Regulatory Peptides,* 141:113-119 (2007), the disclosure of which is incorporated by reference herein. Preferably, the exendin analogs will bind in such receptor binding assays with an affinity of less than 1 μM; an affinity of less than 5 nM; an affinity of less than 1 nM, or an affinity of less than 0.1 nM. In one embodiment, the term "exendin analog" refers to a peptide that has an amino acid sequence with 1, 2, 3, 4, 5, 6, 7, or 8 amino acid substitutions, insertions, deletions, or a combination of two or more thereof, when compared to the amino acid sequence of exendin-4 shown in FIG. 1A. In other embodiment, the term "exendin analog" refers to a peptide that has at least 85%, at least 88%, at least 90%, at least 93%, at least 95%, or at least 98% sequence identity to the amino acid sequence of exendin-4 shown in FIG. 1A. Exendin analogs include the amidated forms, the acid form, the pharmaceutically acceptable salt form, and any other physiologically active form of the molecule. In one embodiment, the term exendin analog can be used interchangeably with the term "exendin agonist analog."

"GLP-1(7-37) analogs" refers to peptides, peptides containing peptide mimetics and/or other modifications, peptides containing the N-terminus conformationally constrained compounds described herein, and/or other chemical moieties, or other compounds which elicit a biological activity similar to that of GLP-1(7-37), when evaluated by art-known measures such as receptor binding assays or in vivo blood glucose assays as described, e.g., Examples 16 and 17, and by Hargrove et al, *Regulatory Peptides,* 141:113-119 (2007), the disclosure of which is incorporated by reference herein. In one embodiment, the term "GLP-1(7-37) analog" refers to a peptide that has an amino acid sequence with 1, 2, 3, 4, 5, 6, 7, or 8 amino acid substitutions, insertions, deletions, or a combination of two or more thereof, when compared to the amino acid sequence of GLP-1(7-37). In one embodiment, the GLP-1(7-37) analog is GLP-1(7-36). GLP-1(7-37) analogs include the amidated forms, the acid form, the pharmaceutically acceptable salt form, and any other physiologically active form of the molecule.

"N-Terminus conformationally constrained GLP-1 receptor agonist compounds" refers to compounds in which one, two, three, or four of the amino acid residues at positions 1-4 at the N-terminus of "GLP-1 receptor agonist compounds" (e.g., exendins, exendin analogs, GLP-1, GLP-1 analogs, GLP-1(7-37), GLP-1(7-37) analogs) have been modified or substituted with amino acids (e.g., natural and/or non-natural amino acids), peptidomimetics, or beta-turn dipetidemimetics. This substitution(s) or modification(s) to the N-terminus of the parent GLP-1 receptor agonist compound changes the flexible random coil structure of this specific region into a more rigid secondary structure with beta-turn characteristics.

The glycine residues at positions 2 and 4 at the N-terminus of exendin-4 may indicate the presence of a β-turn in this region. In order to produce a conformationally constrained N-terminus, exendin analogs having a mimetic or other structural modification that restricted the conformational flexibility of the His[1] side chain were synthesized. Restricting the flexibility of the His[1] side chain was hypothesized to provide structural information about the possible bioactive conformation of GLP-1 receptor agonist compounds and thus enhance GLP-1 receptor binding, in vivo blood glucose lowering activity, and enzymatic stability.

An Ala scan of exendin-4 showed that the Glu[3] residue was important for biological activity. Additionally, Glu[3] or Asp[3] are present in many members of the super-family of glucagon-related peptides, which indicates the importance of an acidic side chain at that residue. It was postulated that the negative charge of Glu[3] or Asp[3] interacted through an ionic bond with the positive charge of the His[1] side chain to position the key imidazole ring of the His[1] side chain in the right space for interaction with the GLP-1 receptor. It was thus proposed that a β-turn would be formed by the sequence Gly[2]Glu[3]Gly[4]Thr[5] in the super-family of glucagon related peptides, such as exendin-4 and exendin analogs.

In order to maintain the negative charge of Glu[3], thought to be essential for biological activity, β-turn peptide mimetics were synthesized to mimic the amino acid residues Glu[3]Gly[4]. In one embodiment, the disclosure provides N-terminus conformationally constrained compounds of Formula (F):

Xaa$_1$Xaa$_2$Xaa$_3$-Z;

wherein:
Xaa$_1$ is a compound of Formula (1), as described herein;
Xaa$_2$ is Gly, Ala, dAla, or Aib;
Xaa$_3$ is:

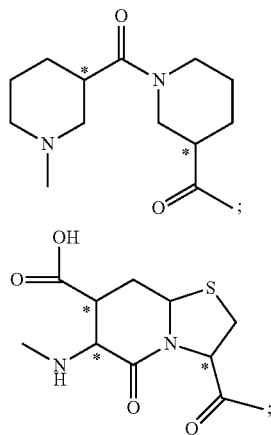

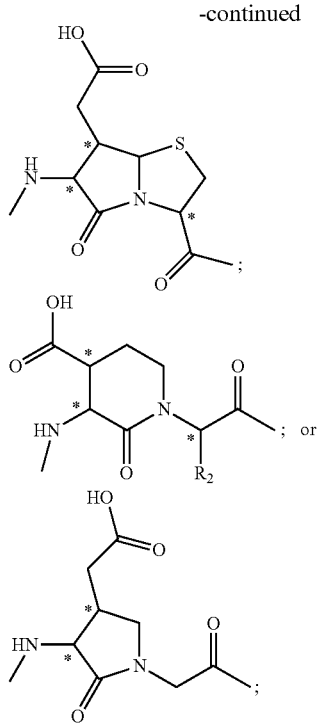

wherein * indicates a chiral carbon atom; and R$_2$ is hydrogen or a C$_{1-4}$ alkyl (e.g., methyl, ethyl); and Z is: (i) OH;
(ii) NH$_2$;
(iii) TFTSDLSKQXaa$_{14}$EEEAVRLFIEXaa$_{25}$LKN-Z$_1$;
(iv) TFTSDLSKQXaa$_{14}$EEEAVRLFIEXaa$_{25}$LKNGGPS SGAPPPS-Z$_1$;
(v) TFTSDLSKQXaa$_{14}$EEEAVRLFIEXaa$_{25}$LK-R$_{10}$-Z$_1$; or
(vi) TFTSDVSSYXaa$_{14}$EGQAAKEFIAXaa$_{25}$LVXaa$_{28}$GRXaa$_{31}$-Z$_1$;

wherein:
Z$_1$ is OH or NH$_2$;
Xaa$_{14}$ is Leu or Met;
Xaa$_{25}$ is Phe or Trp;
Xaa$_{28}$ is Lys or Arg;
Xaa$_{31}$ is Gly or absent; and
R$_{10}$ is QGGPSKEIIS; QGGPSSGAPPPS; NG; NGG; NGGP; NGGPS; NGGPSS; NGGPSSG; NGGPSSGA; NGGPSSGAP; NGGPSSGAPP; NGGPSSGAPPP; NGGPSSGAPPS; NGGPSSGAPPSK; NGGPSSGAPPS(K)$_{2-6}$; NGGPSSGAPPPSK; or NK.

When Z is OH or NH$_2$, the compounds of Formula (F) are N-terminus conformationally constrained compounds. When Z is (iii), (iv), (v) or (vi), the compounds of Formula (F) are N-terminus conformationally constrained GLP-1 receptor agonist compounds.

Exemplary compounds of Formula (F) include the compounds in FIGS. 15A-D and 16A-H, each of which may be optionally amidated at the C-terminal amino acid residue. The reaction schemes for preparing the compounds are shown, e.g., in FIGS. 18-20.

Additional studies were undertaken to restrict the N-terminus conformation of GLP-1 receptor agonist compounds and it was unexpectedly discovered that the β-turn in GLP-1 receptor agonist compounds, such as exendin and exendin analogs, was provided by His[1]Gly[2]Glu[3]Gly[4]. Thus, GLP-1 receptor agonist compounds were produced to constrain or mimic a β-turn defined by residues His¹Gly²Glu³Gly⁴ in exendin-4 and other GLP-1 receptor agonist compounds; or to constrain or mimic a β-turn defined by residues His¹Ala²Glu³Gly⁴ in GLP-1, GLP-1 analogs, GLP-1(7-37), or GLP-1(7-37) analogs.

Provided herein are N-terminus conformationally constrained compounds of Formula (A): $Xaa_1Xaa_2Xaa_3Xaa_4$-Z.

In one embodiment, the disclosure provides the compound of Formula (A):

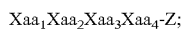

$Xaa_1Xaa_2Xaa_3Xaa_4$-Z;

wherein:
$Xaa_1$ is a compound of Formula (1):

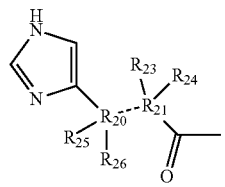

wherein $R_{20}$ and $R_{21}$ are each independently a single bond or a carbon atom; $R_{23}$, $R_{24}$, $R_{25}$ and $R_{26}$ are each independently absent, hydrogen, hydroxyl, $C_{1-4}$ alkyl, carboxyl, or $C_{1-4}$ alkoxy; ------ is a single bond or a double bond; and $R_{21}$ is a chiral or achiral carbon atom;

$Xaa_2$ is Gly, dAla, Aib, Ala, Val, NMeAla, a compound of Formula (3), as described herein; or a compound of Formula (4) and described herein; and $Xaa_2$ is absent when $Xaa_3$ is:

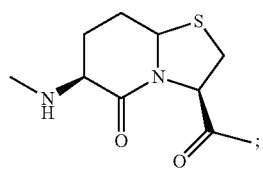

$Xaa_3$ is Pro; a compound of Formula (2), as described herein; a compound of Formula (3), as described herein; a Compound of Formula (4), as described herein;

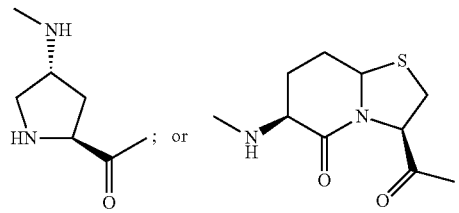

$Xaa_4$ is Gly, dAla, or Aib; and

Z is OH or $NH_2$. In other embodiments, $Xaa_3$ is Pro. In other embodiments, $Xaa_2$ is dAla, Aib, Ala, Val, NMeAla, a compound of Formula (3), or a compound of Formula (4).

In other embodiments, the disclosure provides the compound of Formula (A):

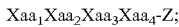

$Xaa_1Xaa_2Xaa_3Xaa_4$-Z;

wherein:
$Xaa_1$ is

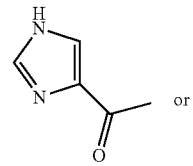

(1j)

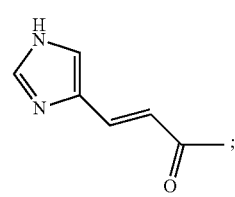

(1m)

$Xaa_2$ is Gly, dAla, Aib, Ala, Val, NMeAla, a compound of Formula (3), as described herein; or a compound of Formula (4), as described herein; and $Xaa_2$ is absent when $Xaa_3$ is:

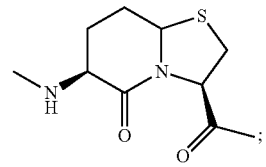

$Xaa_3$ is Glu; Pro; a compound of Formula (2), as described herein; a compound of Formula (3), as described herein; a Compound of Formula (4), as described herein;

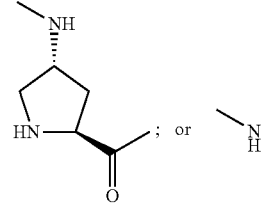

$Xaa_4$ is Gly, dAla, or Aib; and
Z is OH or $NH_2$.

Also provided herein are N-terminus conformationally constrained GLP-1 receptor agonist compounds of Formula (B)-(E):

(B) $Xaa_1Xaa_2Xaa_3Xaa_4TFTSDLSKQXaa_{14}EEEAVRLFIEXaa_{25}LKN-Z$;

(C) $Xaa_1Xaa_2Xaa_3Xaa_4TFTSDLSKQXaa_{14}EEEAVRLFIEXaa_{25}LK-R_{10}-Z$;

(D) $Xaa_1Xaa_2aXaa_3Xaa_4TFTSDLSKQXaa_{14}EEEAVRLFIEXaa_{25}LKNGGPSSGAPPPS-Z$;

(E) $Xaa_1Xaa_2Xaa_3Xaa_4TFTSDVSSYXaa_{14}EGQAAKEFIAXaa_{25}LVXaa_{28}GRXaa_{31}-Z$.

The substituents for the compounds of Formula (A), (B), (C), (D), and (E) are as follows:

Xaa₁ is a compound of Formula (1), as described herein;
Xaa₂ is Gly; dAla; Aib; Ala; Val; NMeAla; a compound of Formula (3), as described herein; or a compound of Formula (4), as described herein; and Xaa₂ is absent when Xaa₃ is:

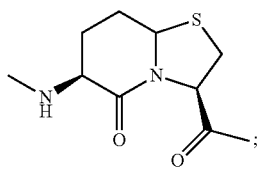

Xaa₃ is Pro; Glu; Asp; a compound of Formula (2), as described herein; a compound of Formula (3), as described herein; a Compound of Formula (4), as described herein;

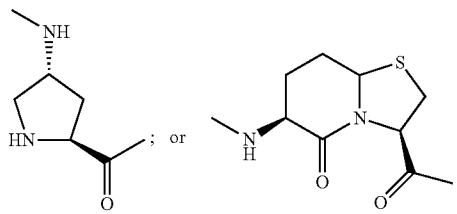

Xaa₄ is Gly, dAla, or Aib;
Xaa₁₄ is Leu or Met;
Xaa₂₅ is Phe or Trp;
Xaa₂₈ is Lys or Arg;
Xaa₃₁ is Gly or absent;
$R_{10}$ is QGGPSKEIIS; QGGPSSGAPPPS; NG; NGG; NGGP; NGGPS; NGGPSS; NGGPSSG; NGGPSSGA; NGGPSSGAP; NGGPSSGAPP; NGGPSSGAPPP; NGGPSSGAPPS; NGGPSSGAPPSK; NGGPSSGAPPS$(K)_{2-5}$; NGGPSSGAPPPSK; or NK; and
Z is OH or $NH_2$.

The compounds of Formula (A)-(E) may optionally be in the form of a pharmaceutically acceptable salt.

The compound of Formula (1) is:

Formula (1)

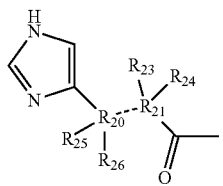

wherein $R_{20}$ and $R_{21}$ are each independently a single bond or a carbon atom; $R_{23}$, $R_{24}$, $R_{25}$ and $R_{26}$ are each independently absent, hydrogen, hydroxyl, $C_{1-4}$ alkyl, carboxyl, amino, or $C_{1-4}$ alkoxy; ------ is a single bond or a double bond; and $R_{21}$ is a chiral or achiral carbon atom.

In one embodiment for the compound of Formula (1), $R_{20}$ and $R_{21}$ are each independently a single bond or a carbon atom; $R_{23}$ and $R_{24}$ are each independently absent, hydrogen, hydroxy, a $C_{1-4}$ alkyl, carboxyl, or a $C_{1-4}$ alkoxy; $R_{25}$ and $R_{26}$ are each independently absent, hydrogen, hydroxy, a $C_{1-4}$ alkyl, carboxyl, amino, or a $C_{1-4}$ alkoxy; ------ is a single bond or a double bond; and $R_2$, is a chiral or achiral carbon atom.

In one embodiment for the compound of Formula (1), $R_{20}$ and $R_{21}$ are each independently a single bond or a carbon atom; $R_{23}$ and $R_{24}$ are each independently absent, hydrogen, hydroxy, methyl, ethyl, or carboxyl; $R_{25}$ and $R_{26}$ are each independently absent or hydrogen; ------ is a single bond or a double bond; and $R_{21}$ is a chiral or achiral carbon atom.

In one embodiment, the compound of Formula (1) is a compound of Formula (1a), (1b), (1c), (1d), (1e), (1f), (1g), (1h), (1j), (1k), (1m), or (1n):

(1a)

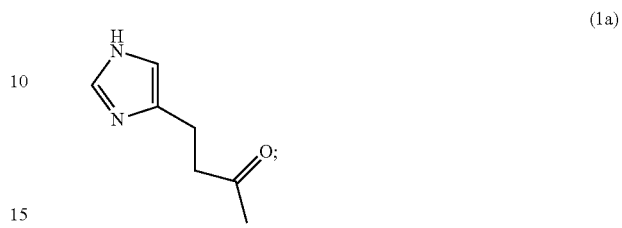

(1b)

(1c)

(1d)

(1e)

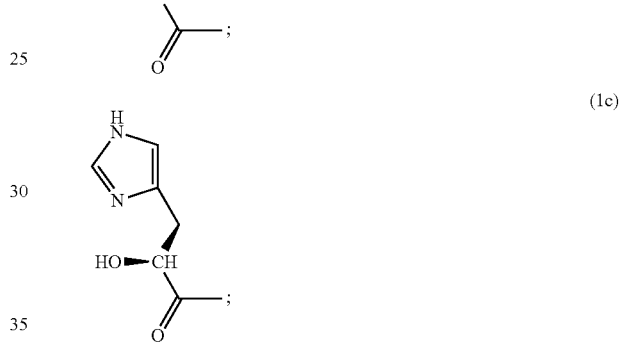

(1f)

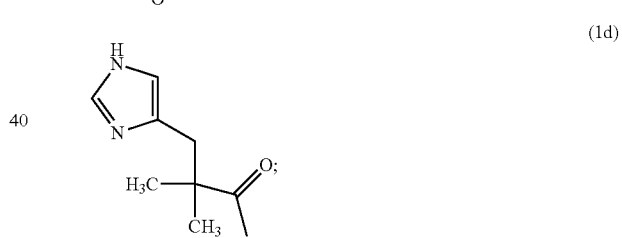

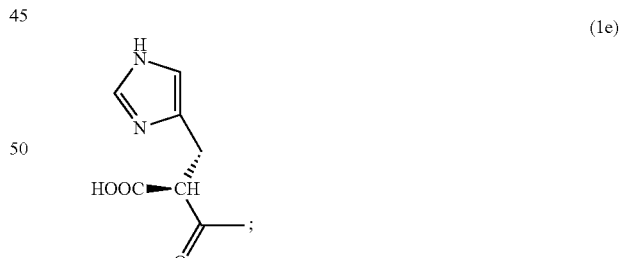

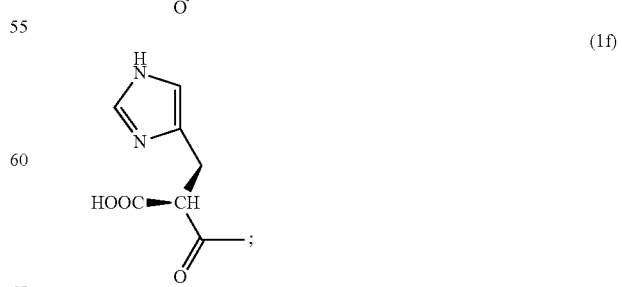

-continued

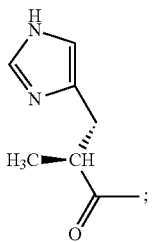
(1g)

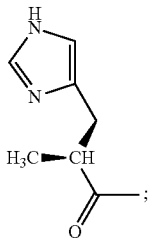
(1h)

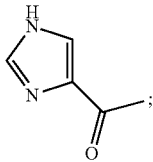
(1j)

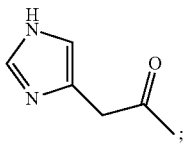
(1k)

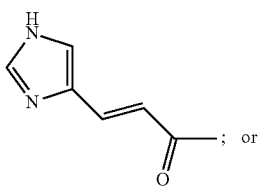
(1m)

; or

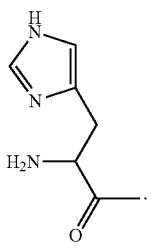
(1n)

In one embodiment, the compound of Formula (1) is a compound of Formula (1a), (1b), (1c), (1d), (1e), (1f), (1g), (1h), (1j), (1k), or (1m).

In one embodiment, the compound of Formula (1) is a compound of Formula (1a), (1b), (1c), (1d), (1e), (1f), (1g), (1h), or (1k).

In one embodiment, the compound of Formula (1) is a compound of Formula (1j) or (1m).

In one embodiment, the compound of Formula (1) is a compound of Formula (1n).

The compounds of Formula (2) and Formula (3) are:

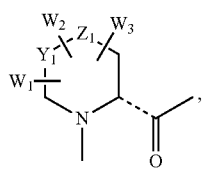
Formula (2)

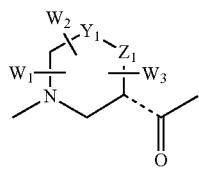
Formula (3)

wherein $Y_1$ and $Z_1$ are each independently a single bond, a carbon, or a sulfur; and $W_1$, $W_2$ and $W_3$ are each independently selected from hydrogen, $C_{1-6}$ alkyl, $C_{1-6}$ alkoxy, hydroxyl, and amino; and when one $Y_1$ or $Z_1$ is sulfur, the sulfur may be bonded to two oxygen atoms to form a sulfonyl group; and ------ is ◄━ or ⋯⋯⋯.

In one embodiment for the Compounds of Formula (2) and (3), $Y_1$ and $Z_1$ are each independently a single bond, a carbon, or a sulfur; and $W_1$, $W_2$ and $W_3$ are each independently selected from hydrogen, $C_{1-4}$ alkyl, $C_{1-4}$ alkoxy, and amino; and when one $Y_1$ or $Z_1$ is sulfur, the sulfur may be bonded to two oxygen atoms to form a sulfonyl group; and ------ is ◄━ or ⋯⋯⋯.

In one embodiment for the Compounds of Formula (2) and (3), $Y_1$ and $Z_1$ are each independently a single bond, a carbon, or a sulfur; and $W_1$, $W_2$ and $W_3$ are each independently selected from hydrogen, $C_{1-4}$ alkyl, and $C_{1-4}$ alkoxy; and when one $Y_1$ or $Z_1$ is sulfur, the sulfur may be bonded to two oxygen atoms to form a sulfonyl group; and ------ is ◄━ or ⋯⋯⋯.

In one embodiment for the Compounds of Formula (2) and (3), ------ is ◄━.

In one embodiment for the Compounds of Formula (2), $Y_1$ and $Z_1$ are each independently a single bond, a carbon, or a sulfur; and $W_1$, $W_2$ and $W_3$ are each independently selected from the group consisting of hydrogen, methyl, ethyl, and propyl; and ------ is ◄━.

In one embodiment for the Compounds of Formula (3), $Y_1$ and $Z_1$ are each independently a single bond or carbon; and $W_1$, $W_2$ and $W_3$ are each independently selected from the group consisting of hydrogen, methyl, ethyl, and propyl; and ------ is ◄━.

In one embodiment, the compound of Formula (2) is a compound of Formula (2Z):

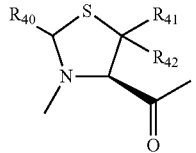
Formula (2Z)

wherein $R_{40}$, $R_{41}$, and $R_{42}$ are each independently selected from the group consisting of hydrogen and $C_{1-4}$ alkyl (preferably methyl or ethyl). Exemplary compounds of Formula (2Z) include compounds of Formula (2d), (2e), (2f), (2g), and (2h) described below.

In one embodiment, the compound of Formula (2) is a compound of Formula (2a), (2b), (2c), (2d), (2e), (2f, (2g), (2h), or (2j):

(2a)
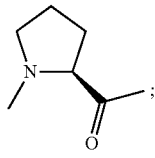

(2b)
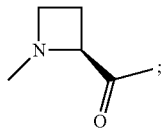

(2c)
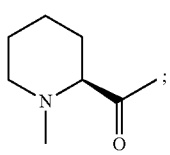

(2d)
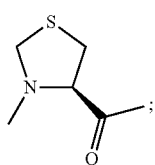

(2e)
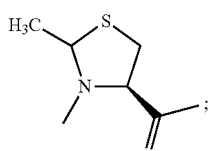

(2f)
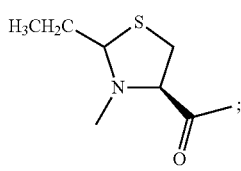

(2g)
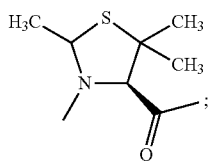

(2h)
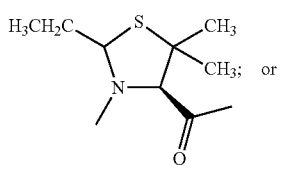

(2j)
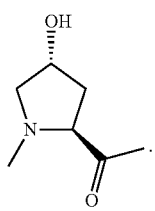

In one embodiment, the compound of Formula (2) is a compound of Formula (2d), (2e), (2f, (2g), or (2h).

In one embodiment, the compound of Formula (3) is a compound of Formula (3a), (3b), or (3c):

(3a)

(3b)
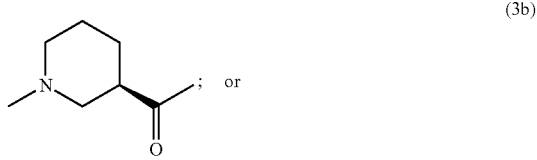

(3c)

The compound of Formula (4) is:

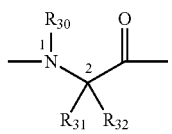

wherein $R_{30}$, $R_{31}$, and $R_{32}$ are each independently hydrogen or a $C_{1-4}$ alkyl; or $R_{30}$ and $R_{31}$, together with the nitrogen[1] and the carbon[2], form a 5-membered or 6-membered heterocyclic ring; or $R_{31}$ and $R_{32}$, together with the carbon[2], form a 3-, 4-, or 5-membered carbocyclic ring.

In one embodiment for the compound of Formula (4), $R_{30}$, $R_{31}$, and $R_{32}$ are each independently hydrogen, methyl, or ethyl; or $R_{30}$ and $R_{31}$, together with the nitrogen[1] and carbon[2], form a 5-membered or 6-membered heterocyclic ring; or $R_{31}$ and $R_{32}$, together with the carbon[2], form a 3-, or 4-membered carbocyclic ring;

In one embodiment, the compound of Formula (4) is a compound of Formula (4a), (4b), (4c), (4d), or (4e):

(4a)

(4b)

-continued

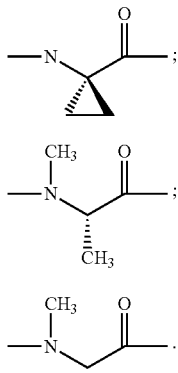

(4c)

(4d)

(4e)

In one embodiment for the Compounds of Formula (A)-(F), Xaa$_2$ is dAla, Aib, Ala, Val, or NMeAla.

In one embodiment for the Compounds of Formula (A)-(F), Xaa$_2$ is a compound of Formula (3).

In one embodiment for the Compounds of Formula (A)-(F), Xaa$_2$ is a compound of Formula (4).

In one embodiment for the Compounds of Formula (A)-(F), Xaa$_2$ is Gly.

In one embodiment for the Compounds of Formula (A)-(F), Xaa$_2$ is dAla.

In one embodiment for the Compounds of Formula (A)-(F), Xaa$_2$ is dAla or Aib.

In one embodiment for the Compounds of Formula (A)-(F), Xaa$_3$ is Pro.

In one embodiment for the Compounds of Formula (A)-(F), Xaa$_3$ is Glu.

In one embodiment for the Compounds of Formula (A)-(F), Xaa$_3$ is a compound of Formula (2), as described herein.

In one embodiment for the Compounds of Formula (A)-(F), Xaa$_3$ is a compound of Formula (3), as described herein.

In one embodiment for the Compounds of Formula (A)-(F), Xaa$_2$ is absent and Xaa$_3$ is

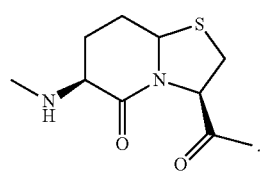

In one embodiment for the Compounds of Formula (A)-(F), Xaa$_4$ is Gly or dAla.

In one embodiment for the Compounds of Formula (A)-(F), Z is NH$_2$.

For the Compounds of Formula (A)-(F): in one embodiment R$_{10}$ is QGGPSKEIIS; in one embodiment R$_{10}$ is NG; in one embodiment R$_{10}$ is NGG; in one embodiment R$_{10}$ is NGGP; in one embodiment R$_{10}$ is NGGPS; in one embodiment R$_{10}$ is NGGPSS; in one embodiment R$_{10}$ is NGGPSSG; in one embodiment R$_{10}$ is NGGPSSGA; in one embodiment R$_{10}$ is NGGPSSGAP; in one embodiment R$_{10}$ is NGGPSSGAPP; in one embodiment R$_{10}$ is NGGPSSGAPPP; in one embodiment R$_{10}$ is NGGPSSGAPPS; in one embodiment R$_{10}$ is NGGPSSGAPPSK; in one embodiment R$_{10}$ is NGGPSSGAPPS(K)$_{2-5}$; in one embodiment R$_{10}$ is NGGPSSGAPPPSK; and in one embodiment R$_{10}$ is NK; and in one embodiment R$_{10}$ is QGGPSSGAPPPS.

For the Compounds of Formula (A)-(F): in one embodiment Xaa$_{14}$ is Met and Xaa$_{25}$ is Trp; in one embodiment Xaa$_{14}$ is Leu and Xaa$_{25}$ is Phe; in one embodiment Xaa$_{14}$ is Met and Xaa$_{25}$ is Phe; and in one embodiment Xaa$_{14}$ is Leu and Xaa$_{25}$ is Trp.

With respect to the compounds of Formula (D), Xaa$_2$, Xaa$_3$, Xaa$_{14}$, and Xaa$_{25}$ cannot simultaneously be Gly, Glu, Met, and Trp, respectively, except when the compound of Formula (1) is a compound of Formula 1(j) or 1(m). Thus, when Xaa$_2$, Xaa$_3$, Xaa$_{14}$, and Xaa$_{25}$ are Gly, Glu, Met, and Trp, respectively, the compound of Formula (D) may be one of the following:

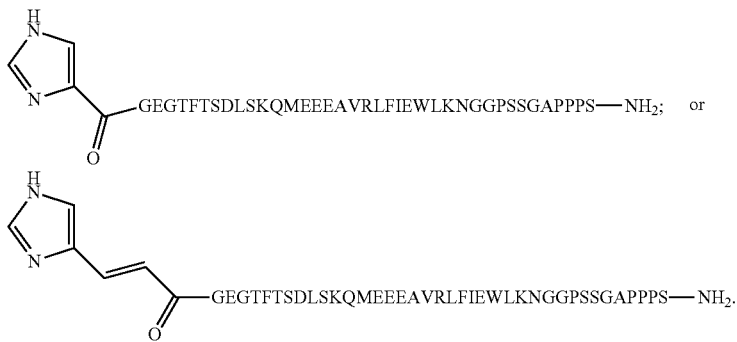

In one embodiment, the N-terminus conformationally constrained GLP-1 receptor agonist compound may be Pro$^3$-exendin-4; Pro$^3$,Leu$^{14}$-exendin-4; Pro$^3$,Leu$^{14}$,Phe$^{25}$-exendin-4; Pro$^3$-exendin-4(1-28); Pro$^3$,Leu$^{14}$-exendin-4(1-28); Pro$^3$,Leu$^{14}$,Phe$^{25}$-exendin-4(1-28); Pro$^3$-exendin-4(1-36); Pro$^3$,Leu$^{14}$-exendin-4(1-36); Pro$^3$,Leu$^{14}$,Phe$^{25}$-exendin-4(1-36); or HGPGTFTSDLSKQLEEEAVR-LFIEWLKQGGPSKEIIS, each of which may optionally be amidated and which may optionally be in the form of a pharmaceutically acceptable salt.

In one embodiment, the N-terminus conformationally constrained GLP-1 receptor agonist compound may be Pro$^3$-exendin-3; Pro$^3$-exendin-4(1-29); Pro$^3$,Leu$^{14}$,Phe$^{25}$-exendin-4(1-29); Pro$^3$-exendin-4(1-30); Pro$^3$,Leu$^{14}$,Phe$^{25}$-exendin-4(1-30); Pro$^3$-exendin-4(1-31); Pro$^3$,Leu$^{14}$,Phe$^{25}$-exendin-4(1-31); Pro$^3$-exendin-4(1-32); Pro$^3$,Leu$^{14}$,Phe$^{25}$-exendin-4(1-32); Pro$^3$-exendin-4(1-33); Pro$^3$,Leu$^{14}$,Phe$^{25}$-exendin-4(1-33); Pro$^3$-exendin-4(1-34); Pro$^3$,Leu$^{14}$,Phe$^{25}$-exendin-4(1-34); Pro$^3$-exendin-4(1-35); Pro$^3$,Leu$^{14}$, Phe$^{25}$- exendin-4(1-35); Pro³-exendin-4(1-37); Pro³,Leu¹⁴,Phe²⁵-exendin-4(1-37); Pro³-exendin-4(1-38); or Pro³,Leu¹⁴,Phe²⁵-exendin-4(1-38), each of which may optionally be amidated and which may optionally be in the form of a pharmaceutically acceptable salt.

Examples of the compounds of Formula (A), (B), (C), (D), and (E) are shown in FIGS. 1B-C, 2A-U, 3A-G, 5B-G, 6A-E, 8A-H, 9A-H, 10A-I, 11A-B, 12, 13, 14A-Q, 15C-D, 16I-L, and 17A-N.

The N-terminus conformationally constrained compounds (e.g., compounds of Formula (A) and (F)) and the N-Terminus conformationally constrained GLP-1 receptor agonist compounds (e.g., compounds of Formula (B)-(F)) described herein (collectively referred to as "the compounds") can optionally be covalently linked to one or more polymers to provide beneficial biological properties to the compounds. Such beneficial properties may include conferring another therapeutic property to the compounds; increasing the in vivo half life of the compounds; decreasing the rate of clearance of the compounds by the kidney; decreasing the immunogenicity of the compounds; decreasing the proteolysis rate of the compounds; or increasing the stability of the compounds. Exemplary polymers that can be covalently linked to the compounds include peptides, polyethylene glycols, albumin, fatty acids, dextran, polyamino acids, alkyl chains, immunoglobulins, signaling moieties, gelatin, polyvinyl pyrrolidone, polyvinyl alcohol, N-(2-hydroxypropyl)-methacrylamide, and the like. In one embodiment, two or more polymers (e.g., peptides, polyethylene glycols, albumin, fatty acids, dextran, polyamino acids, alkyl chains, immunoglobulins, gelatin, polyvinyl pyrrolidone, polyvinyl alcohol, N-(2-hydroxypropyl)-methacrylamide) are covalently attached together and linked to the N-terminus conformation constrained compounds described herein. For example, the two more polymers that are linked together may be polyethylene glycol(s) and fatty acid(s) or a peptide, polyethylene glycol(s), and fatty acids.

In one embodiment, the compounds are linked to another peptide to provide additional therapeutic benefits. Such peptides include amylin, amylin agonist analogs (e.g., amylin analogs that function as amylin agonists), PYY, PYY analogs, GIP, GIP analogs, leptin, metraleptin, leptin analogs, metraleptin analogs, and the like. Hybrid peptides comprising the compounds and another therapeutic peptide are described, for example, in WO 2005/077072 and WO 2007/022123, the disclosures of which are incorporated by reference herein.

In one embodiment, compounds are linked to one, two, or three polyethylene glycols. In one embodiment, the compounds are linked to one polyethylene glycol. The polyethylene glycol can have a molecular weight from about 200 daltons to about 80,000 daltons; from about 5,000 from about 10,000 daltons to about 60,000 daltons; from about 10,000 daltons to about 50,000 daltons; or from about 15,000 daltons to about 40,000 daltons. The polyethylene glycol may be linear or branched.

In one embodiment, compounds are linked to one or two polyethylene glycols, where the polyethylene glycol is further linked to a lipophilic moiety. In one embodiment, the polyethylene glycol may have a molecular weight from about 200 to about 7,000 daltons or from about 500 to about 5,000 daltons. The lipophilic moiety may be an alkyl group (e.g., $C_{1-20}$ alkyl group; $C_{1-10}$ alkyl group; $C_{1-6}$ alkyl group; $C_{1-4}$ alkyl group), a fatty acid (e.g., $C_{4-28}$ fatty acid; $C_{4-20}$ fatty acid; $C_{4-10}$ fatty acid), cholesteryl, adamantyl, and the like. The alkyl group may be linear or branched, preferably linear. In one embodiment, the fatty acid is an acetylated fatty acid or an esterified fatty acid. The -(polyethylene glycol)-(lipophilic moiety) may be linked to the compound at a C-terminal amino acid residue, an N-terminal amino acid residue, an internal amino acid residue (e.g., an internal Lys amino acid residue), or a combination thereof (e.g., the compound is linked at the N-terminal and C-terminal amino acid residues via a lysine residue). Examplary peptides linked to such groups are shown in Example 20.

In one embodiment, the compounds are linked to a polyamino acid. Exemplary polyamino acids include polylysine, poly-aspartic acid, poly-serine, poly-glutamic acid, and the like. The polyamino acid may be in the D or L form, preferably the L form. The polyamino acids may comprise from 1 to 12 amino acid residues; from 2 to 10 amino acid residues; or from 2 to 6 amino acid residues.

In one embodiment, compounds are linked to a fatty acid. The fatty acid may be a $C_4$-$C_{28}$ fatty acid chain, a $C_8$-$C_{24}$ fatty acid chain, or a $C_{10}$-$C_{20}$ fatty acid chain. In one embodiment, the fatty acid is an acetylated fatty acid. In one embodiment, the fatty acid is an esterified fatty acid.

In one embodiment, the compounds are linked to albumin. The albumin may be a recombinant albumin, serum albumin, or recombinant serum albumin. In another embodiment, the compounds are linked to an albumin-fatty acid (i.e., an albumin linked to a fatty acid).

In one embodiment, the compounds are linked to an immunoglobulin or an immunoglobulin Fc region. The immunoglobulin may be IgG, IgE, IgA, IgD, or IgM. In one embodiment, the compounds are linked to an IgG Fc region or an IgM Fc region. The immunoglobulin Fc region is (i) the heavy chain constant region $2(C_H2)$ of an immunoglobulin; (ii) the heavy chain constant region $3(C_H3)$ of an immunoglobulin; or (iii) both the heavy chain constant regions $2(C_H2)$ and $3(C_H3)$ of an immunoglobulin. The immunoglobulin Fc region may further comprise the hinge region at the heavy chain constant region. Other embodiments for the immunoglobulin Fc region that can be linked to exendin analog peptides are described in WO 2008/082274, the disclosure of which is incorporated by reference herein.

In one embodiment, the compounds are linked to one or more signalling moieties. Exemplary signalling moieties include, biotin, antigens, antibodies, receptors, enzymes, chemiluminescent groups, photoreactive groups, fluorescent groups, heavy metal-containing compounds (e.g., ferritin), and the like.

When the compounds described herein are covalently linked to one or more polymers, such as those described herein, any linking group known in the art can be used. The linking group may comprise any chemical group(s) suitable for linking the peptide to the polymer. Alternatively, compounds can be directly attached to the polymer without any linking group. Exemplary linking groups include amino acids, maleimido groups, dicarboxylic acid groups, succinimide groups, or a combination of two or more thereof. Methods for linking peptides to one or more polymers are known in the art and described, for example, in U.S. Pat. No. 6,329,336; U.S. Pat. No. 6,423,685; U.S. Pat. No. 6,924,264; WO 2005/077072, WO 2007/022123, WO 2007/053946; WO 2008/058461; and WO 2008/082274, the disclosures of which are incorporated by reference herein.

The compounds described herein may be prepared using biological, chemical, and/or recombinant DNA techniques that are known in the art. Exemplary methods are described in U.S. Pat. No. 6,872,700; WO 2007/139941; WO 2007/140284; WO 2008/082274; WO 2009/011544; and US Publication No. 2007/0238669, the disclosures of which are incorporated herein by reference. Other methods for preparing the compounds are set forth herein.

The compounds described herein may be prepared using standard solid-phase peptide synthesis techniques, such as an automated or semiautomated peptide synthesizer. Typically, using such techniques, an alpha-N-carbamoyl protected amino acid and an amino acid attached to the growing peptide chain on a resin are coupled at room temperature in an inert solvent (e.g., dimethylformamide, N-methylpyrrolidinone, methylene chloride, and the like) in the presence of coupling agents (e.g., dicyclohexylcarbodiimide, 1-hydroxybenzotriazole, and the like) in the presence of a base (e.g., diisopropylethylamine, and the like). The alpha-N-carbamoyl protecting group is removed from the resulting peptide-resin using a reagent (e.g., trifluoroacetic acid, piperidine, and the like) and the coupling reaction repeated with the next desired N-protected amino acid to be added to the peptide chain. Suitable N-protecting groups are well known in the art, such as t-butyloxycarbonyl (tBoc) fluorenylmethoxycarbonyl (Fmoc), and the like. The solvents, amino acid derivatives and 4-methylbenzhydryl-amine resin used in the peptide synthesizer may be purchased from Applied Biosystems Inc. (Foster City, Calif.).

Solid phase peptide synthesis may be carried out with an automatic peptide synthesizer (Model 430A, Applied Biosystems Inc., Foster City, Calif.) using the NMP/HOBt (Option 1) system and tBoc or Fmoc chemistry (See Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Boc-peptide-resins may be cleaved with HF (−5° C. to 0° C., 1 hour). The peptide may be extracted from the resin with alternating water and acetic acid, and the filtrates lyophilized. The Fmoc-peptide resins may be cleaved according to standard methods (e.g., Introduction to Cleavage Techniques, Applied Biosystems, Inc., 1990, pp. 6-12). Peptides may be also be assembled using an Advanced Chem Tech Synthesizer (Model MPS 350, Louisville, Ky.).

Peptides may be purified by RP-HPLC (preparative and analytical) using a Waters Delta Prep 3000 system. A C4, C8 or C18 preparative column (10μ, 2.2X25 cm; Vydac, Hesperia, Calif.) may be used to isolate peptides, and purity may be determined using a C4, C8 or C18 analytical column (5μ, 0.46X25 cm; Vydac). Solvents (A=0.1% TFA/water and B=0.1% TFA/$CH_3CN$) may be delivered to the analytical column at a flow rate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20-24 h). Hydrolysates may be derivatized and analyzed by standard methods (Cohen et al, The Pico Tag Method: A Manual of Advanced Techniques for Amino Acid Analysis, pp. 11-52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer.

The compounds described herein may also be prepared using recombinant DNA techniques using methods known in the art, such as Sambrook et al., Molecular Cloning: A Laboratory Manual, 2d Ed., Cold Spring Harbor (1989). Non-peptide compounds may be prepared by art-known methods. For example, phosphate-containing amino acids and peptides containing such amino acids, may be prepared using methods known in the art, such as described in Bartlett et al, Biorg. Chem., 14:356-377 (1986).

The disclosure also provides pharmaceutical compositions comprising at least one of the N-terminus conformationally constrained compounds or the N-terminus conformationally constrained GLP-1 receptor agonist compounds described herein and a pharmaceutically acceptable carrier. The N-terminus conformationally constrained compounds or the N-terminus conformationally constrained GLP-1 receptor agonist compounds can be present in the pharmaceutical composition in a therapeutically effective amount and can be present in an amount to provide a minimum blood plasma level for therapeutic efficacy.

Pharmaceutical compositions containing the compounds described herein may be provided for peripheral administration, such as parenteral (e.g., subcutaneous, intravenous, intramuscular), topical, nasal, or oral administration. Suitable pharmaceutically acceptable carriers and their formulation are described in standard formulation treatises, such as Remington's Pharmaceutical Sciences by Martin; and Wang et al, Journal of Parenteral Science and Technology, Technical Report No. 10, Supp. 42:2S (1988).

The compounds described herein can be provided in parenteral compositions for injection or infusion. They can, for example, be suspended in water; an inert oil, such as a vegetable oil (e.g., sesame, peanut, olive oil, and the like); or other pharmaceutically acceptable carrier. In one embodiment, the compounds are suspended in an aqueous carrier, for example, in an isotonic buffer solution at a pH of about 3.0 to 8.0, or about 3.0 to 5.0. The compositions may be sterilized by conventional sterilization techniques or may be sterile filtered. The compositions may contain pharmaceutically acceptable auxiliary substances as required to approximate physiological conditions, such as pH buffering agents. Useful buffers include for example, acetic acid buffers. A form of repository or "depot" slow release preparation may be used so that therapeutically effective amounts of the preparation are delivered into the bloodstream over many hours or days following subcutaneous injection, transdermal injection or other delivery method. The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

The compounds can also be formulated as pharmaceutically acceptable salts (e.g., acid addition salts) and/or complexes thereof. Pharmaceutically acceptable salts are non-toxic salts at the concentration at which they are administered. Pharmaceutically acceptable salts include acid addition salts such as those containing sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Carriers or excipients can also be used to facilitate administration of the compounds. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

Compositions may be prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

The therapeutically effective amount of the compounds described herein to treat the diseases described herein will typically be from about 0.01 µg to about 5 mg; about 0.1 µg to about 2.5 mg; about 1 mg to about 1 mg; about 1 µg to about 50 µg; or about 1 µg to about 25 µg. Alternatively, the therapeutically effective amount of the GLP-1 receptor agonist compounds may be from about 0.001 µg to about 100 µg based on the weight of a 70 kg patient; or from about 0.01 µg to about 50 µg based on the weight of a 70 kg patient. These therapeutically effective doses may be administered once/day, twice/day, thrice/day, once/week, biweekly, or once/month, depending on the formulation. The exact dose to be administered is determined, for example, by the formulation, such as an immediate release formulation or an extended release formulation. For transdermal, nasal or oral dosage forms, the dosage may be increased from about 5-fold to about 10-fold.

The compounds described herein and pharmaceutical compositions comprising the compounds are useful for treating diabetes. The diabetes can be Type I diabetes, Type II diabetes, or gestational diabetes. The methods for treating diabetes provide administering to a patient in need thereof a therapeutically effective amount of one or more of the N-terminus conformationally constrained compounds or the N-terminus conformationally constrained GLP-1 receptor agonist compounds described herein to treat diabetes in the patient.

The compounds described herein and pharmaceutical compositions comprising the compounds are useful for treating insulin resistance and stimulating insulin release. The methods for treating insulin resistance provide administering to a patient in need thereof a therapeutically effective amount of one or more of the N-terminus conformationally constrained compounds or the N-terminus conformationally constrained GLP-1 receptor agonist compounds described herein to treat insulin resistance in the patient. The methods for treating stimulating insulin release provide administering to a patient in need thereof a therapeutically effective amount of one or more of the N-terminus conformationally constrained compounds or the N-terminus conformationally constrained GLP-1 receptor agonist compounds described herein to stimulate insulin release in the patient.

The compounds described herein and pharmaceutical compositions comprising the compounds are useful for treating postprandial hyperglycemia. The methods for treating postprandial hyperglycemia provide administering to a patient in need thereof a therapeutically effective amount of one or more of the N-terminus conformationally constrained compounds or the N-terminus conformationally constrained GLP-1 receptor agonist compounds described herein to treat postprandial hyperglycemia in the patient.

The compounds described herein and pharmaceutical compositions comprising the compounds are useful for lowering blood glucose levels and lowering HbA1c levels. The methods for lowering blood glucose levels provide administering to a patient in need thereof a therapeutically effective amount of one or more of the N-terminus conformationally constrained compounds or the N-terminus conformationally constrained GLP-1 receptor agonist compounds described herein to lower blood glucose levels in the patient. In one embodiment, the blood glucose levels can be fasting blood glucose levels. The methods for lowering HbA1c levels provide administering to a patient in need thereof a therapeutically effective amount of one or more of the N-terminus conformationally constrained compounds or the N-terminus conformationally constrained GLP-1 receptor agonist compounds described herein to lower HbA1c levels in the patient. HbA1c levels are generally a long-term measure of a patient's blood glucose levels.

The compounds described herein and pharmaceutical compositions comprising the compounds are useful for reducing gastric motility and delaying gastric emptying. The methods for reducing gastric motility provide administering to a patient in need thereof a therapeutically effective amount of one or more of the N-terminus conformationally constrained compounds or the N-terminus conformationally constrained GLP-1 receptor agonist compounds described herein to reduce gastric motility in the patient. The methods for delaying gastric emptying provide administering to a patient in need thereof a therapeutically effective amount of one or more of the N-terminus conformationally constrained compounds or the N-terminus conformationally constrained GLP-1 receptor agonist compounds described herein to delay gastric emptying in the patient.

The compounds described herein and pharmaceutical compositions comprising the compounds are useful for reducing food intake, reducing appetite, increasing satiety, and reducing weight. The methods for reducing food intake provide administering to a patient in need thereof a therapeutically effective amount of one or more of the N-terminus conformationally constrained compounds or the N-terminus conformationally constrained GLP-1 receptor agonist compounds described herein to reduce food intake in the patient. The methods for reducing appetite provide or increasing satiety administering to a patient in need thereof a therapeutically effective amount of one or more of the N-terminus conformationally constrained compounds or the N-terminus conformationally constrained GLP-1 receptor agonist compounds described herein to reduce appetite in the patient. The methods for treating reducing weight provide administering to a patient in need thereof a therapeutically effective amount of one or more of the N-terminus conformationally constrained compounds or the N-terminus conformationally constrained GLP-1 receptor agonist compounds described herein to reduce weight in the patient. In the methods described herein, the patient may be in need of a reduced intake in food, of a reduced appetite, or of reduced weight. In other methods described herein, the patient may be desirous of having a reduced intake in food, of having a reduced appetite, or of having a reduced weight. The patient may be of any weight, and can be overweight or obese.

The compounds described herein and pharmaceutical compositions comprising the compounds are useful for treating overweight and obesity. The methods for treating overweight provide administering to a patient in need thereof a therapeutically effective amount of one or more of the N-terminus conformationally constrained compounds or the N-terminus conformationally constrained GLP-1 receptor agonist compounds described herein to treat overweight in the patient. The methods for treating obesity provide administering to a patient in need thereof a therapeutically effective amount of one or more of the N-terminus conformationally constrained compounds or the N-terminus conformationally constrained GLP-1 receptor agonist compounds described herein to treat obesity in the patient.

The disclosure also provides drug delivery devices having at least one therapeutically effective dose of the compounds described herein or the pharmaceutical composition containing the compounds described herein. The drug delivery devices can be single or multiple-use vials, single or multiple-use pharmaceutical pens, single or multiple-use cartridges, and the like. In one embodiment, the drug delivery devices contain the compounds or pharmaceutical compositions described herein in amounts capable of providing a patient with from about 7 to about 40 doses or enough doses to last about one week or about one month.

EXAMPLES

The following examples are for purposes of illustration only and are not intended to limit the scope of the claims.

Example 1

Figure 16A:
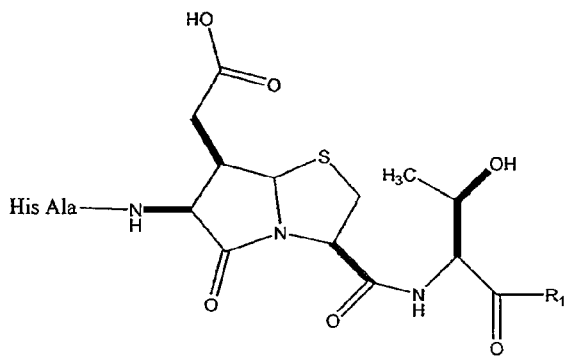
FIGS. 16A-H are exendin analogs containing a modification at the N-terminus. R$_1$ is FTSDLSKQLEEE-AVRLFIEWLKQGGPSKEIIS-OH. R$_2$ is FTSDLSKQLE EEAVRLFIEWLKNGGPSSGAPPPS-NH$_2$. R$_3$ is FTSDVS-SYLEGQAAKEFIAWLVKGRG-NH$_2$.

Preparation of Compound in FIG. 16A

A calculated 100 µmol of Fmoc-Ser(OtBu)-Wang resin was weighed into a reaction vessel in a Symphony peptide synthesizer, and the peptide elongation was carried out following standard Fmoc peptide synthesis protocol up to residue $Thr^5$. The resulting peptide-resin intermediate (0.3 g, 0.0927 mmol) was swollen in dimethylformamide (DMF) and to the slurry was added compound 7 (0.110 g, 2.2 eq), followed by O-(benzotriazol-1-yl)-N,N,N',N' tetramethyluronium hexafluorophosphate (HBTU) (0.035 g, 2.2 eq), N-hydroxybenzotriazole (HOBt) (0.03 g, 2.2 eq) and methylmorpholine (NMM) (0.04 mL, 4.4 eq). After 3 hours, the resin was washed with DMF 6×, treated with 20% piperidine in DMF 2×25 min and washed with DMF 6×. The above cycle was repeated with Fmoc-Ala-OH and Fmoc-His(Trt)-OH followed by cleavage of the peptide from the resin with 10 ml TFA/H$_2$O/PhOH/TIPS (95:2:2:1) (TFA is trifluoroacetic acid; TIPS is triisopropylsilyl), precipitated by methyl-tert-Butyl ether and the obtained residue applied to a reverse-phase high performance liquid chromatography (HPLC) column (C$_{18}$, 20-50% CH$_3$CN in 0.1% TFA/H$_2$O over 30 min gradient) to afford the titled compound as a white powder (16.4 mg, 6%): Retention time in reverse phase-high performance liquid chromatography (RP-HPLC) (C$_{18}$, 5-75% CH$_3$CN in 0.1% TFA/H$_2$O over 15 min) is 9.78 min; Calculated mass for C$_{189}$H$_{294}$N$_{48}$O$_{60}$S (M+H)$^+$4231.84. found by liquid chromatography/mass spectrometry (LC-MS) 1411.3 (M+3H)$^{3+}$, 1059.6 (M+4H)$^{4+}$, 2117.2 (M+2H)$^{2+}$.

Example 2

Figure 16B:
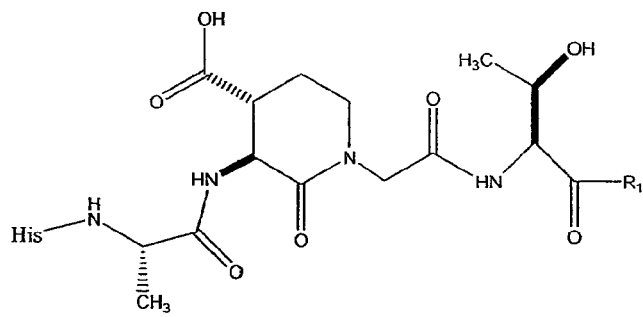

Preparation of Compound in FIG. 16B

A calculated 100 µmol of Fmoc-Ser(OtBu)-Wang resin was weighed into a reaction vessel in a Symphony peptide synthesizer, and the peptide elongation was carried out following standard Fmoc peptide synthesis protocol up to residue $Thr^5$. The resulting peptide-resin intermediate (0.3 g, 0.0927 mmol) was swollen in DMF and to the slurry was added compound 24 (0.122 g, 2.2 eq), followed by HBTU (0.035 g, 2.2 eq), HOBt (0.03 g, 2.2 eq) and NMM (0.04 mL, 4.4 eq). After 3 hours, the resin was washed with DMF 6×, treated with 20% piperidine in DMF 2×25 min and washed with DMF 6×. The above cycle was repeated with Fmoc-His(Trt)-OH followed by cleavage of the peptide from the resin with 10 ml TFA/H$_2$O/PhOH/TIPS (95:2:2:1), precipitated by methyl-tert-Butyl ether. The obtained crude peptide was dissolved in 1.5 mL of MeOH:ACN (1:1) (ACN is acetonitrile), followed by addition of 2M LiOH (0.6 mL) and the reaction stirred at RT for 6 h. The crude was dissolved and applied to a reverse-phase HPLC column (C$_{18}$, 20-50% CH$_3$CN in 0.1% TFA/H$_2$O over 30 min gradient) to afford the titled compound as a white powder (15 mg, 6%): Retention time in RP-HPLC (C$_{18}$, 5-75% CH$_3$CN in 0.1% TFA/H$_2$O over 15 min) is 9.82 min; Calculated mass for C$_{188}$H$_{294}$N$_{48}$O$_{60}$ (M+H)$^+$ 4186.72. found by LC-MS 1396.7 (M+3H)$^{3+}$, 1048.6 (M+4H)$^{4+}$, 2114.2 (M+2H)$^{2+}$.

Example 3

Figure 16C:
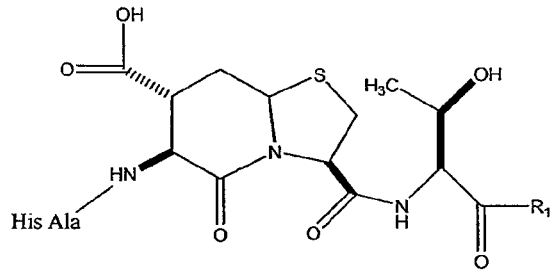

Preparation of Compound in FIG. 16C

A calculated 100 µmol of Fmoc-Ser(OtBu)-Wang resin was weighed into a reaction vessel in a Symphony peptide synthesizer, and the peptide elongation was carried out following standard Fmoc peptide synthesis protocol up to residue $Thr^5$. The resulting peptide-resin intermediate (0.3 g, 0.0927 mmol) was swollen in DMF and to the slurry was added compound 18 (0.131 g, 2.2 eq), followed by HBTU (0.035 g, 2.2 eq), HOBt (0.03 g, 2.2 eq) and NMM (0.04 mL, 4.4 eq). After 3 hours, the resin was washed with DMF 6×, treated with 20% piperidine in DMF 2×25 min and washed with DMF 6×. The above cycle was repeated with Fmoc-His(Trt)-OH followed by cleavage of the peptide from the resin with 10 ml TFA/H$_2$O/PhOH/TIPS (95:2:2:1), precipitated by methyl-tert-Butyl ether. The obtained crude peptide was dissolved in 1.5 mL of MeOH:ACN (1:1), followed by addition of 2M LiOH (0.6 mL) and the reaction stirred at RT for 6 h. The crude was dissolved and applied to a reverse-phase HPLC column (C$_{18}$, 20-50% CH$_3$CN in 0.1% TFA/H$_2$O over 30 min gradient) to afford the titled compound as a white powder (19.7 mg, 8%): Retention time in RP-HPLC(C$_{18}$, 5-75% CH$_3$CN in 0.1% TFA/H$_2$O over 15 min) is 8.58 min; Calculated mass for C$_{189}$H$_{294}$N$_{48}$O$_{60}$S (M+H)$^+$ 4230.80. found by LC-MS 1411. (M+3H)$^{3+}$, 1059.6 (M+4H)$^{4+}$, 2117.2 (M+2H)$^{2+}$.

Example 4

Figure 16D:
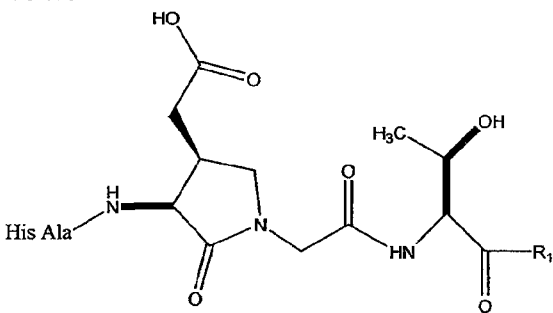
Figure 16E:
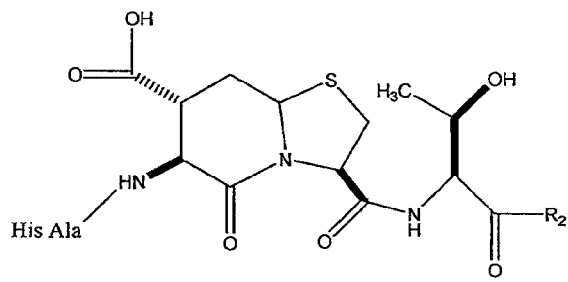

Preparation of Compound in FIG. 16E

The synthesis of this compound was accomplished following the same experimental procedure as described for Example 3. The only difference was the sequence of the peptide-resin intermediate, starting with Rink-amide resin. The crude was dissolved and applied to a reverse-phase HPLC column (C$_{18}$, 20-50% CH$_3$CN in 0.1% TFA/H$_2$O over 30 min gradient) to afford the titled compound as a white powder (15.7 mg, 7%): Retention time in RP-HPLC(C$_{18}$, 5-75% CH$_3$CN in 0.1% TFA/H$_2$O over 15 min) is 8.25 min; Calculated mass for C$_{188}$H$_{286}$N$_{48}$O$_{60}$S (M+H)$^+$ 4238.74. found by LC-MS 1414.8 (M+3H)$^{3+}$, 1061.6 (M+4H)$^{4+}$, 2121.2 (M+2H)$^{2+}$.

Example 5

Preparation of Compound in FIG. 16D

A calculated 100 μmol of Fmoc-Ser(OtBu)-Wang resin was weighed into a reaction vessel in a Symphony peptide synthesizer, and the peptide elongation was carried out following standard Fmoc peptide synthesis protocol up to residue Thr$^5$. The resulting peptide-resin intermediate (0.3 g, 0.0927 mmol) was swollen in DMF and to the slurry was added compound 11 (0.100 g, 2.2 eq), followed by HBTU (0.035 g, 2.2 eq), HOBt (0.03 g, 2.2 eq) and NMM (0.04 mL, 4.4 eq). After 3 h, the resin was washed with DMF 6×, treated with 20% piperidine in DMF 2×25 min and washed with DMF 6×. The above cycle was repeated with Fmoc-Ala-OH and Fmoc-His(Trt)-OH followed by cleavage of the peptide from the resin with 10 ml TFA/H$_2$O/PhOH/TIPS (95:2:2:1), precipitated by methyl-tert-Butyl ether and the obtained residue applied to a reverse-phase HPLC column (C$_{18}$, 20-50% CH$_3$CN in 0.1% TFA/H$_2$O over 30 min gradient) to afford the titled compound as a white powder (20.3 mg, 10%): Retention time in RP-HPLC(C$_{18}$, 5-75% CH$_3$CN in 0.1% TFA/H$_2$O over 15 min) is 9.74 min; Calculated mass for C$_{188}$H$_{294}$N$_{48}$O$_{60}$ (M+H)$^+$ 4186.72. found by LC-MS 1396.7 (M+3H)$^{3+}$, 1048.6 (M+4H)$^{4+}$, 2114.2 (M+2H)$^{2+}$.

Example 6

Figure 16F:
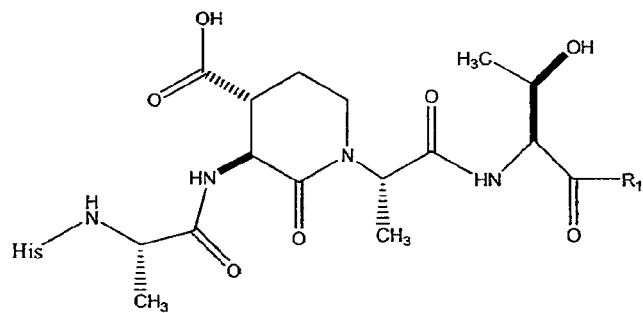

Preparation of Compound in FIG. 16F

A calculated 100 μmol of Fmoc-Ser(OtBu)-Wang resin was weighed into a reaction vessel in a Symphony peptide synthesizer, and the peptide elongation was carried out following standard Fmoc peptide synthesis protocol up to residue Thr$^5$. The resulting peptide-resin intermediate (0.3 g, 0.0927 mmol) was swollen in DMF and to the slurry was added compound 21 (0.125 g, 2.2 eq), followed by HBTU (0.035 g, 2.2 eq), HOBt (0.03 g, 2.2 eq) and NMM (0.04 mL, 4.4 eq). After 3 h, the resin was washed with DMF 6×, treated with 20% piperidine in DMF 2×25 min and washed with DMF 6×. The above cycle was repeated with Fmoc-His(Trt)-OH followed by cleavage of the peptide from the resin with 10 ml TFA/H$_2$O/PhOH/TIPS (95:2:2:1), precipitated by methyl-tert-Butyl ether. The obtained crude peptide was dissolved in 1.5 mL of MeOH:ACN (1:1), followed by addition of 2M LiOH (0.6 mL) and the reaction stirred at RT for 6 h. The crude was dissolved and applied to a reverse-phase HPLC column (C$_{18}$, 20-50% CH$_3$CN in 0.1% TFA/H$_2$O over 30 min gradient) to afford the titled compound as a white powder (8 mg, 4%): Retention time in RP-HPLC(C$_{18}$, 5-75% CH$_3$CN in 0.1% TFA/H$_2$O over 15 min) is 7.93 min; Calculated mass for C$_{189}$H$_{296}$N$_{48}$O$_{60}$ (M+H)$^+$ 4200.75. found by LC-MS 1401.8 (M+3H)$^{3+}$, 1051.6 (M+4H)$^{4+}$, 2102.2 (M+2H)$^{2+}$.

Example 7

Figure 16G:
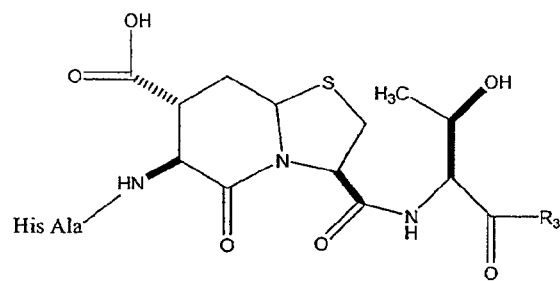
Figure 16H:
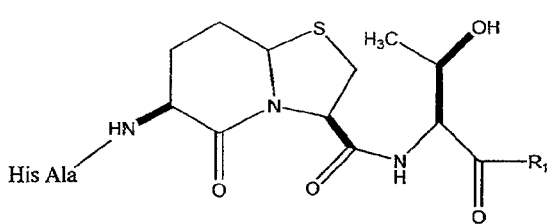
Figure 16I:
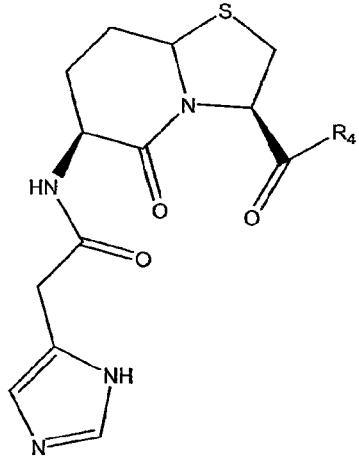
FIGS. 16I-L are exendin analogs containing a modification at the N-terminus. The modification is designed to mimic amino acid residues His$^1$Gly$^2$Glu$^3$. R$_4$ is GTFTSDLSKQLEE EAVRLFIEFLKN-NH$_2$.
Figure 16J:
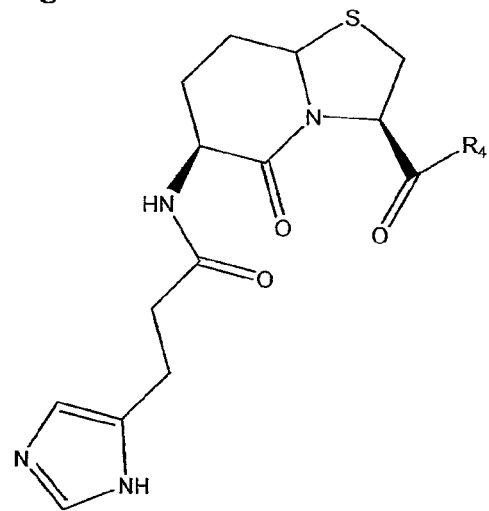
Figure 16K:
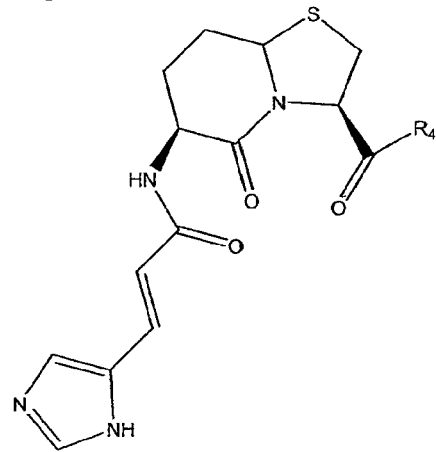
Figure 16L:
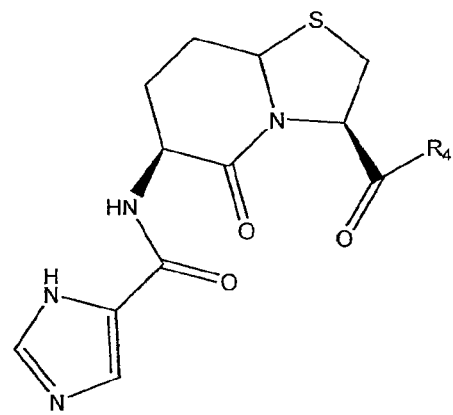
Figure 17A:
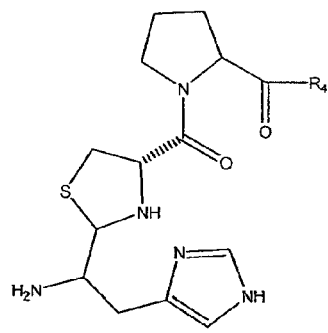
FIGS. 17A-F are exendin analogs containing a thiazolidine-proline peptide mimetics at Gly$^2$Glu$^3$. R$_4$ is GTFTSDLSKQLEEEAVRLFIEFLKN-NH$_2$.
Figure 17B:
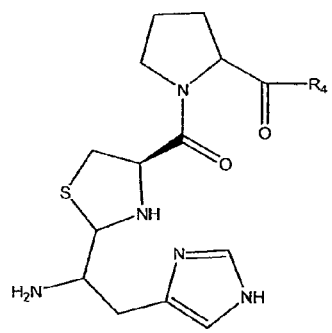
Figure 17C:
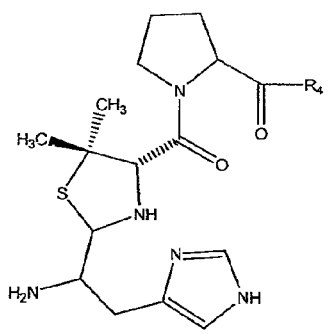
Figure 17D:
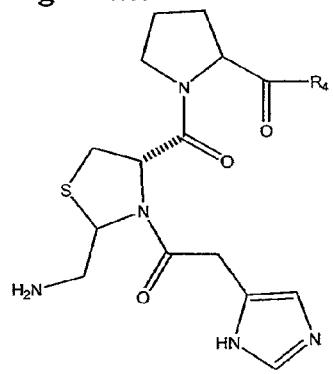
Figure 17E:
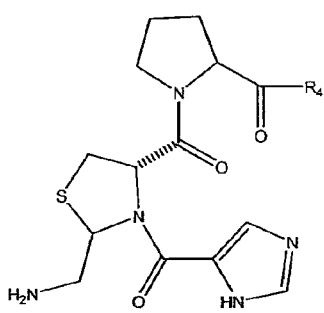
Figure 17F:
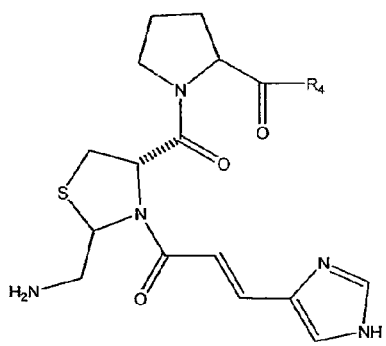
Figure 17G:
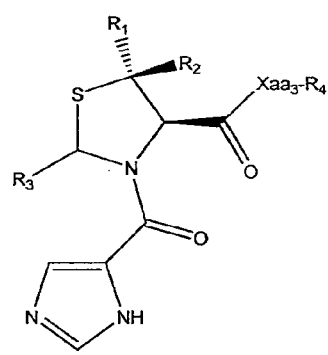
FIGS. 17G-N are exendin analogs having a modification at His$^1$ and containing a thiazolidine peptide mimetic at Gly$^2$Glu$^3$. R$_1$, R$_2$, and R$_3$ are each independently hydrogen, methyl, or ethyl. In this embodiment, Xaa$_3$ is Glu, Asp, Pro, or Gly. R$_4$ is GTFTS-DLSKQLEEEAVRLFIEFLKN-NH$_2$.
Figure 17H:
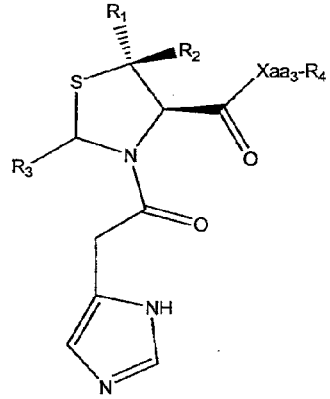
Figure 17I:
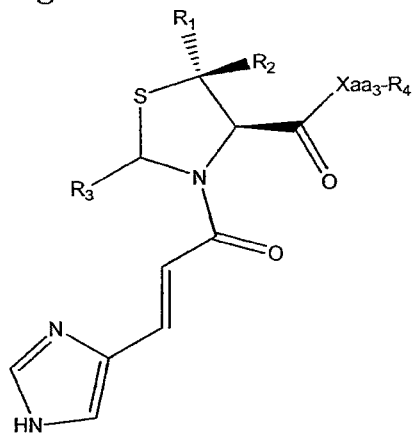
Figure 17J:
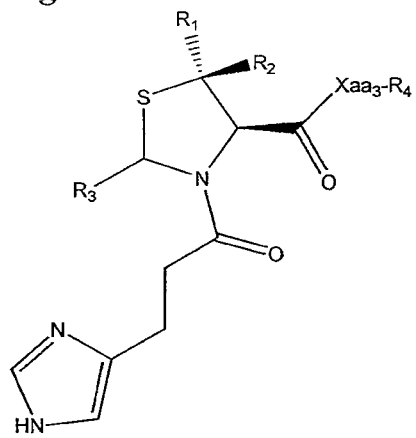
Figure 17K:
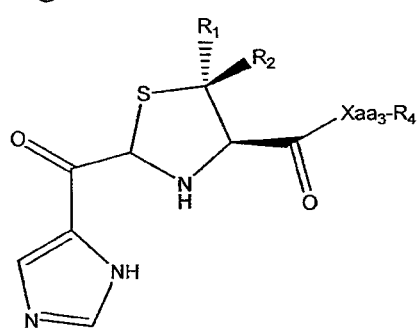
Figure 17L:
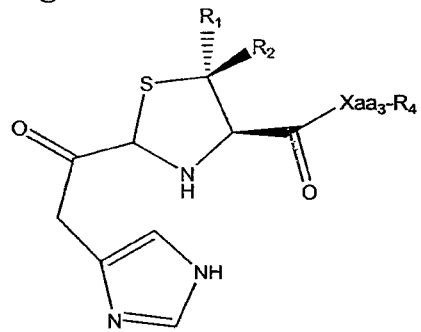
Figure 17M:
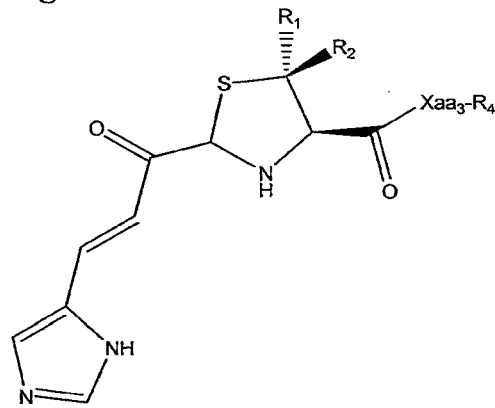
Figure 17N:
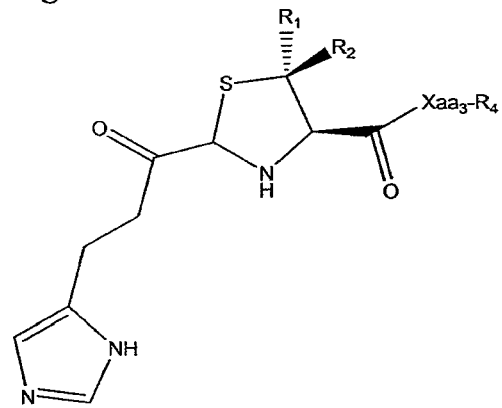

Preparation of Compound in FIG. 16G

The synthesis of this compound was accomplished following the same experimental procedure as described for Example 3. The only difference was the sequence of the peptide-resin intermediate. The crude was dissolved and applied to a reverse-phase HPLC column (C$_{18}$, 20-50% CH$_3$CN in 0.1% TFA/H$_2$O over 30 min gradient) to afford the titled compound as a white powder (27.4 mg, 18%): Retention time in RP-HPLC(C$_{18}$, 5-75% CH$_3$CN in 0.1% TFA/H$_2$O over 15 min) is 8.25 min; Calculated mass for C$_{153}$H$_{228}$N$_{40}$O$_{47}$S (M+H)$^+$ 3411.83. found by LC-MS 1138.6 (M+3H)$^{3+}$, 854.5 (M+4H)$^{4+}$, 1707.9 (M+2H)$^{2+}$.

Example 8

Figure 18A:
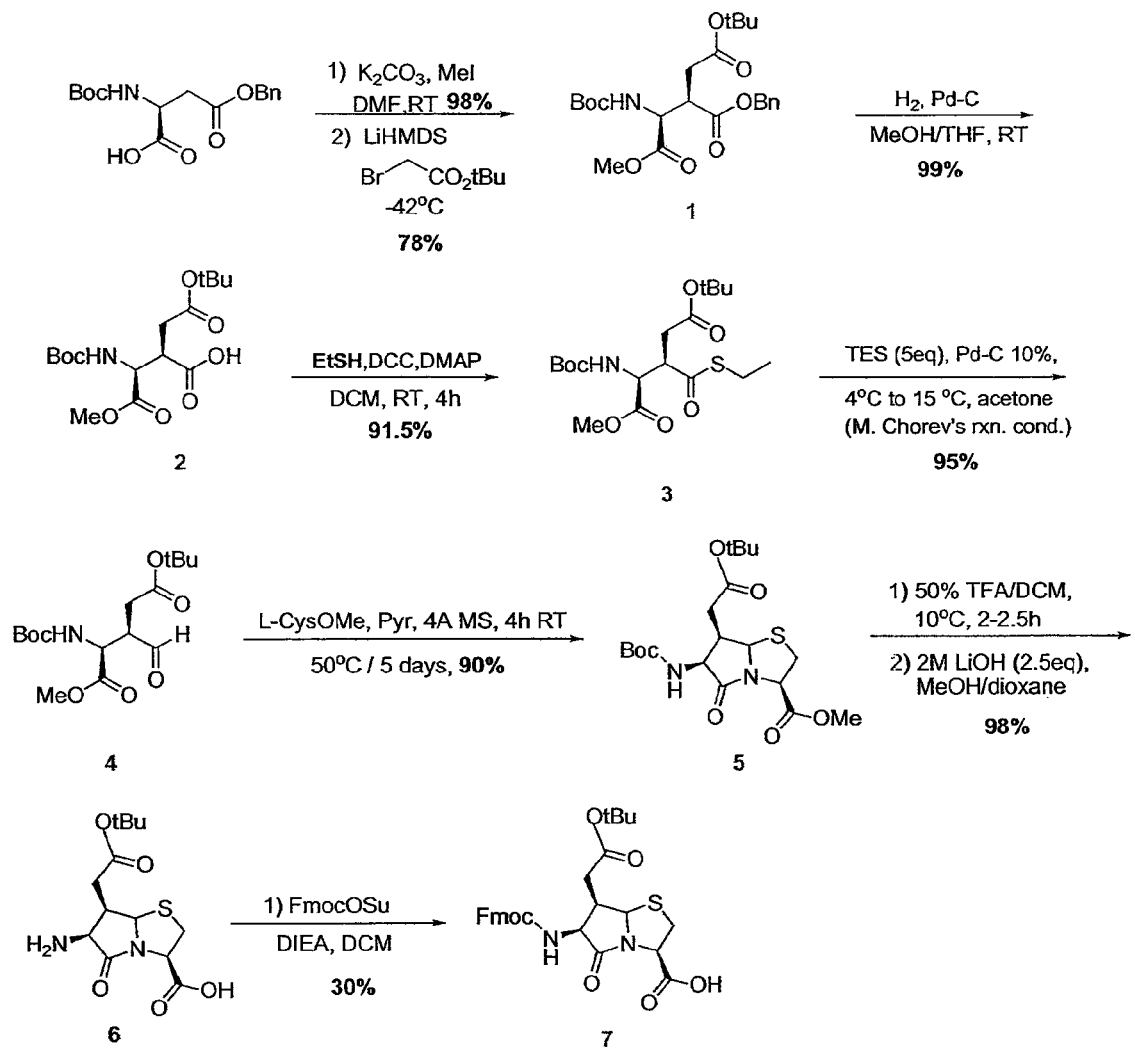
FIG. 18A is a process for preparing (5,5)-Glu-Gly-OH, a dipeptide mimetic that can be used to induce a β-turn conformational constraint, for example, at the N-terminus in a GLP-1 receptor agonist compound.
Figure 18B:
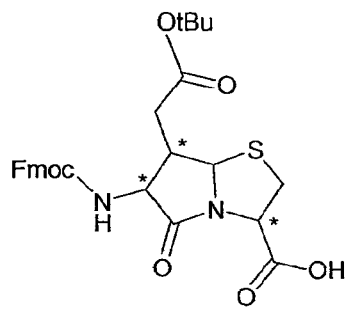
FIG. 18B is a generic structure of the compound that can be produced by the process shown in FIG. 18A. The skilled artisan can choose compounds with different stereochemistries during the reaction process to provide for various stereochemistries in the final product. * represents a chiral carbon atom.

Preparation of (5,5)-Glu-Gly-OH as shown in FIG. 18

Preparation of Boc-Asp(OBn)-OMe: Boc-Asp(OBn)-OH 2.4 g (1 equiv, 7.45 mmol) was dissolved in 17 mL of dry DMF in a 100 mL round-bottom flask. Finely ground K$_2$CO$_3$ (1.5 g, 11 mmol) was added to the solution to form a suspension. The mixture was cooled to 0° C. in an ice-bath over five minutes. MeI (1 mL, 15 mmol) was then added to the mixture over 20 seconds under a positive flow of nitrogen. A yellow color developed within 30 min. The resulting mixture was stirred for 3 hours. The ice-bath was removed and 25 mL of water were added and the mixture left standing at room temperature 2 hours. The mixture was then treated with 30 mL of water and extracted with 3×25 mL AcOEt. The organics were washed with saturated NaHCO$_3$ 1×, brine 3×, dried over Na$_2$SO$_4$ filtered and concentrated to yield a yellow oil. This material was passed through a short silica column (eluting w/ AcOEt), after concentration of the pure fractions 2.42 g of Boc-Asp(OBn)-OMe as a yellow oil was obtained (98% yield). $^1$H NMR (DMSO d6, 500 mHz): δ 7.36 (m, 5H), 5.10 (s, 2H), 4.40 (q, 1H), 3.6 (s, 3H), 2.80 (dd, 1H), 2.72 (dd, 1H), 1.38 (s, 9H). LCMS (C$_{18}$, 2-98% CH$_3$CN in 0.1% TFA/H$_2$O over 6 min); Calculated mass for C$_{17}$H$_{23}$NO$_6$ (M+H)$^+$ 338.23. found by LC-MS 338.2.

Preparation of Compound 1 in FIG. 18: Boc-Asp(OBn)-OMe (26.4 g, 78.3 mmol) was dissolved in a 500 mL round-bottom flask with 110 mL of dry THF and the mixture cooled at negative 42° C. To this mixture was added lithium bis (trimethylsilyl)amide (LiHMDS) (173 mL, 1 M solution, 2.2 eq). This solution was stirred under a gentle argon flow for 45 min followed by slow addition (via syringe) of tert-butyl bromo acetate (14.5 mL, 1.25 eq). Thin layer chromatography (TLC) (Hex:AcOEt, 8/2) showed after 4 h>95% of expected product. The reaction was quenched by addition of saturated NH$_4$Cl (70 mL). The mixture was evaporated and the residue re-dissolved with 100 mL of dichloromethane (DCM). The emulsion formed was separated by standing overnight. The organics were collected and washed with saturated NH$_4$Cl 2×, brine 1×, dried over Na$_2$SO$_4$, filtered and concentrated to give Compound 1 as a red orange oil. Flash chromatography (Hex:AcOEt, 7:3) gave 27.4 g of a yellow oil (78% yield). $^1$H NMR (DMSO d6, 500 mHz): δ 7.35 (m, 5H), 5.08 (s, 2H), 4.57 (dd, 1H), 4.05 (m, 1H), 3.52 (s, 3H), 1.39 (s, 9H), 1.34 (s, 9H). LCMS (C$_{18}$, 2-98% CH$_3$CN in 0.1% TFA/H$_2$O over 6 min); Calculated mass for C$_{23}$H$_{33}$NO$_8$ (M+H)$^+$ 452.23. found by LC-MS 452.2.

Preparation of Compound 2 in FIG. 18. Compound 2 is tert-butyl-(1S,2R)-2-[(carboxy)-3-tert-butoxycarbonyl)-1-metoxhycarbonyl)]propylcarbamate. Compound 1 (5.8 g, 12.8 mmol) was dissolved in 30 mL of a 6:4 mixture of MeOH/THF. Argon was bubbled in the catalyst for 5 minutes, followed by incorporation of two hydrogen balloons attached via syringe to the reaction flask. After 4 hours, LCMS shows complete transformation. The crude mixture was filtrated through celite and concentrated to yield 5.25 g of Compound 2 as an orange oil which was used without further purification in the next step. Calculated mass for C$_{16}$H$_{27}$NO$_8$ (M+H)$^+$ 362.23. found by LC-MS 362.2.

Preparation of Compound 3 in FIG. 18. Compound 3 is tert-butyl-(1S,2R)-2-[(benzylthio)-carbonyl)-3-tert-butoxycarbonyl)-1-metoxhycarbonyl)]propylcarbamate. Compound 2 (2.1 g, 5.8 mmol) was dissolved with DCM (7 mL). To this clear mixture was added ethylthiol (0.4 g, 1.1 eq) and 4-dimethylaminopyridine (DMAP) (0.07 g, 0.1 eq). To the clear solution was added dicyclohexyl carbodiimide (DCC) (1.3 g, 1.1 eq) as a solid and the mixture was stirred at room temperature for 5 hours. The mixture was diluted with DCM (40 mL) and washed with 1N HCl (2×), dried over $Na_2SO_4$, filtered and concentrated to give 2.15 g of Compound 3 as a yellow oil, which was used without further purification in the next step. Calculated mass for $C_{18}H_{31}NO_7S$ $(M+H)^+$ 406.13. found by LC-MS 406.2.

Preparation of Compound 4 in FIG. 18. Compound 4 is tert-butyl-(1S,2R)-3-(tert-butoxcarbonyl)-1-(methoxycarbonyl)-2-formylpropylcarbamate. To Compound 3 (5.9 g, 14.5 mmol) and Pd—C 10% wt (0.35 g) were added acetone (36 mL) and the mixture cooled down to about 4-8° C. To this mixture was added drop wise, under positive flow of Argon, triethylsilyl (TES) (11.5 mL, 5 eq). After addition of TES the mixture was kept at 10-15° C. After 3.5 hours LCMS showed no more starting material. The mixture was filtrated through celite, and the solution concentrated to give 6.6 g of Compound 4 as a green oil which was used without further purification in the next step. Calculated mass for $C_{16}H_{27}NO_7$ $(M+H)^+$ 346.13. found by LC-MS 346.2.

Preparation of Compound 5 in FIG. 18. Compound 5 is methyl-[3S,4R,8R]-1-Aza-3-tert-butoxycarbonyl-4-(tert-butoxycarbonyl)methyl)-2-oxo-6-thiabicyclic[3.3.0]-octane-8-carboxylate. To Compound 4 (1.3 g, 3.76 mmol), L-Cys-OH—HCl (0.98 g, 1.5 eq) and 4° A molecular sieves (2g) was added dry pyridine (10 mL) and the mixture stirred, under argon, at room temperature for 4 hours in high pressure vessel. After this time, 3.5 mL more of pyridine were added and the reaction was stirred at 50° C. for 5 days. After this time, the crude mixture was filtered through celite, the solution was re-dissolved in AcOEt and washed with 2N HCl 2×, dried over $Na_2SO_4$, filtered and concentrated to yield 1.2 g of Compound 5 as a yellowish semisolid, which was used without further purification in the next step. Calculated mass for $C_{19}H_{30}N_2O_7S$ $(M+H)^+$ 431.13. found by LC-MS 431.2.

Preparation of Compound 6 in FIG. 18. Compound 6 is [3S,4R,8R]-1-Aza-3-amino-4-(tert-butoxycarbonyl)methyl)-2-oxo-6-thiabicyclic[3.3.0]-octane-8-carboxylate. Crude Compound 5 was treated with 10 mL of a 50% TFA-DCM mixture at 0° C. The mixture was let to warm up at 10° C. and stirred for 2.5 hours. The mixture is then concentrated and the residue re-dissolved with 5 mL of a 2M LiOH solution and stirred at room temperature for 2.5 hours. LCMS analysis showed complete transformation to Compound 6. The reaction was concentrated and the residue passed through a short column packed with ion-exchange resin ($H^+$, Dowex), eluting with 1:1 $MeOH/H_2O$. The residue was concentrated and then lyophilized to give 1.8 g of crude Compound 6 as a yellow semisolid, which was used without further purification in the next step. Calculated mass for $C_{13}H_{20}N_2O_5S$ $(M+H)^+$ 317.13. found by LC-MS 317.2.

Preparation of Compound 7 in FIG. 18. Compound 7 is the (5,5)-Glu-Gly bicylic dipeptide mimetic. Compound 7 is also referred to as [3S,4R,8R]-1-Aza-3-fluorenylmethyl-carbonyl-4-(tert-butoxycarbonyl)methyl)-2-oxo-6-thiabicyclic [3.3.0]-octane-8-carboxylate. Crude Compound 6 (1.2 g, 3.8 mmol) was dissolved in 17 mL of dry DCM. To this solution was added FmocOSu (1.8 g, 1.4 eq) followed by N,N-diisopropylethylamine (DIEA) (1.3 mL, 2 eq). The reaction was stirred at room temperature for 3 hours. To the mixture was added 50 mL of DCM and washed with 2M HCl 2×, brine 1×, dried over $Na_2SO_4$, filtered and concentrated to give 1.42 g of a yellow oil. Purification by flash chromatography using an increasing polarity solvent gradient (Hex:AcOEt 1:1 to DCM:MeOH 9:1) gave 0.150 g of pure Compound 7. Calculated mass for $C_{28}H_{30}N_2O_7S$ $(M+H)^+$ 539.13. found by LC-MS 539.2.

Example 9

Figure 19A:
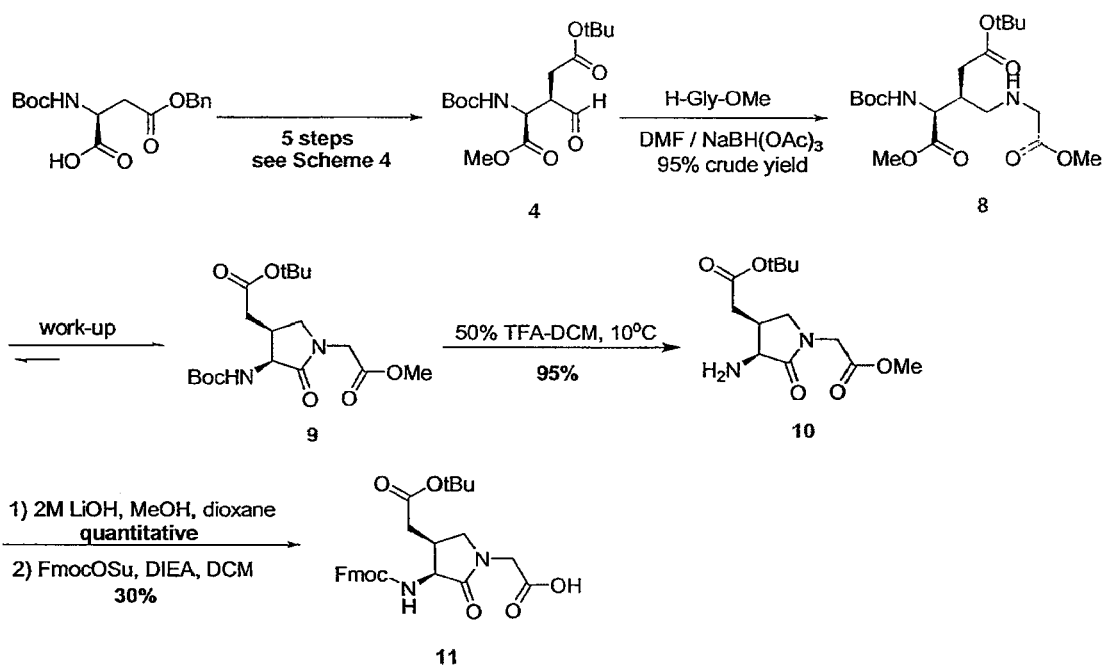
FIG. 19A is a process for preparing γ-lactam Glu-Gly-OH, a dipeptide mimetic that can be used to induce a β-turn conformational constraint, for example, at the N-terminus in a GLP-1 receptor agonist compound.
Figure 19B:
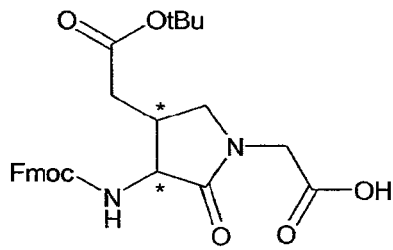
FIG. 19B is a generic structure of the compound that can be produced by the process shown in FIG. 19A. The skilled artisan can choose compounds with different stereochemistries during the reaction process to provide for various stereochemistries in the final product. * represents a chiral carbon atom.

Preparation of Compound 11 in FIG. 19

Compound 9 is 1-Aza-3-amino-tert-butoxylcarbonyl-4-(tert-butoxycarbonyl)methyl)-2-oxo-1-methoxyacetyl. Compound 4 was prepared as described above. A solution of Compound 4 (preparation described in Example 8) (4.1 g, 12 mmol) and the HCl salt of $NH_2$-Gly-OMe (1.66 g, 1.1 eq) in 20 mL of DMF were stirred at room temperature. To this mixture was added $NaBH(OAc)_3$ (5.0 g, 2 eq) dissolved in 18 mL of DMF. After 1 hour LCMS shows complete transformation to the desired secondary amine 8. Calculated mass for $C_{19}H_{34}N_2O_8$ $(M+H)^+$ 419.1. found by LC-MS 419.2. To this crude mixture was added AcOEt (80 mL), washed with sat. $NaHCO_3$ 3×, water 1×, brine 1×, dried over $Na_2SO_4$, filtered and concentrated to give 3.9 g of a crude yellow oil. LCMS of this material showed that the five-member ring lactam (Compound 9) was formed during work-up. The residue was concentrated to give 3.9 g of crude Compound 9 as a yellow oil, which was used without further purification in the next step. Calculated mass for $C_{18}H_{30}N_2O_7$ $(M+H)^+$ 387.1. found by LC-MS 387.2.

Preparation of Compound 10 in FIG. 19. Compound 10 is 1-amino-4-(tert-butoxy-carbonyl)methyl)-2-oxo-1-methoxyacetyl. Crude Compound 9 (3.8 g) was cooled at 10° C. in an ice-water bath. To this stirred mixture was added in a drop wise manner 15 mL of a 50% solution of TFA in DCM. The mixture was stirred at that temperature for 2 h. LCMS showed a selective N-Boc deprotection. The mixture was concentrated to yield crude compound 10 as clear semisolid, which was used without further purification in the next step. Calculated mass for $C_{13}H_{22}N_2O_5$ $(M+H)^+$ 287.1. found by LC-MS 287.2.

Preparation of Compound 11 in FIG. 19. Compound 11 is a γ-lactam-Glu-Gly bicyclic dipeptide mimetic which is 1-Aza-3-aminofluorenylmethylcarbonyl-4-(tert-butoxycarbonyl)methyl)-2-oxo-1-acetylcarboxylate. Crude Compound 10 (2.8 g, 9.8 mmol) was dissolved in 8 mL of a 1:1 mixture of dioxane/MeOH at room temperature. To this mixture was added 15 mL of a 2M LiOH (2.8 eq) and the mixture stirred at room temperature for 3 hours. The mixture was then concentrated and passed trough a short column of Dowex $H^+$ ion-exchange resin. The pooled fractions containing M+1=273 by LCMS were collected and lyophilized. This crude material was then dissolved in DCM (40 mL) followed by addition of DIEA (3.5 mL, 2 eq) and FmocOSu (3.9 g, 1.2 eq). The mixture was stirred at room temperature for 3 hours. LCMS analysis shows no more starting material, thus to the reaction was added AcOEt (60 mL), washed with sat. $NaHCO_3$ 3×, water 1×, brine 1×, dried over $Na_2SO_4$, filtered and concentrated to give 2.5 g of a crude Compound 11. The mixture was purified by flash chromatography using AcOEt: Hex (1:1). Collection of the pure fractions identified by LCMS gave 100 mg of pure Compound 11. Calculated mass for $C_{27}H_{30}N_2O_7$ $(M+H)^+$ 495.1. found by LC-MS 495.2.

Example 10

Figure 20A:
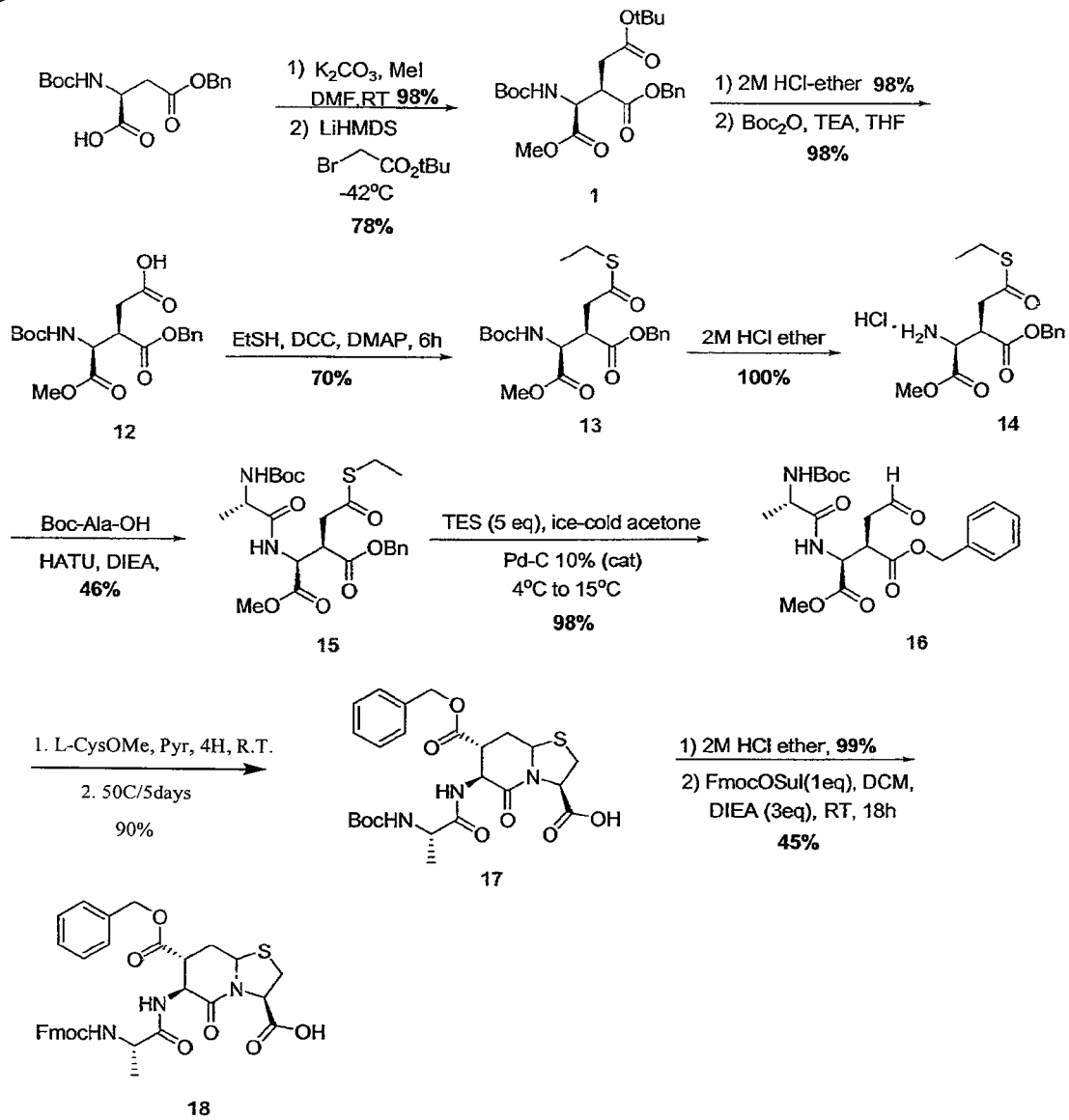
FIG. 20A is a process for preparing (6,5)-Asp-Gly-OH, a dipeptide mimetic that can be used to induce β-turn conformational constraint, for example, at the N-terminus in a GLP-1 receptor agonist compound.
Figure 20B:
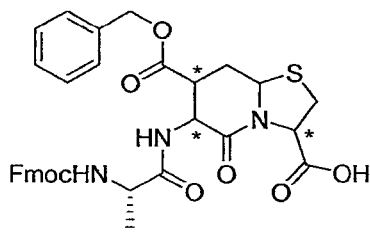
FIG. 20B is a generic structure of the compound that can be produced by the process shown in FIG. 20A. The skilled artisan can choose compounds with different stereochemistries during the reaction process to provide for various stereochemistries in the final product. * represents a chiral carbon atom.

Preparation of Compound 18 in FIG. 20

Compound 1 (i.e., tert-butyl-1(1S,2R)-2-[(benzyloxy)carbonyl)-3-tert-butoxycarbonyl)-1-metoxhycarbonyl)]propyl-carbamate) was prepared as described in Example 8 above.

Preparation of Compound 12 in FIG. 20. Compound 12 is tert-Butyl-(1S,2R)-2-[(benzylcarboxylate)-3-carboxy)-1-metoxhycarbonyl)]propylcarbamate. To Compound 1 (13.9 g, 30.8 mmol) was added 45 mL of a 2M solution of HCl in diethyl ether. The clear yellow solution was stirred at room temperature for 18 hours. The mixture was triturated with cold ether which gave a yellow foam. Drying of this solid gave 8.32 g (84% yield) of the hydrochloride salt intermediate which was used without further purification in the next step. This HCl salt crude (8.3 g, 25 mmol) was dissolved in THF (80 mL). To this clear solution was added TEA (7.6 mL, 2.2 eq) followed by Boc$_2$O (6.5 g, 1.2 eq). The mixture was stirred for 18 hours at room temperature. The mixture was then concentrated, re-dissolved in AcOEt (150 mL), washed with 1N HCl 2×, sat. NaCl 1×, dried over Na$_2$SO$_4$, filtered, concentrated and dried under high vacuum to yield Compound 12 as a brownish oil (11.1 g, 100% crude yield), which was used without further purification in the next step. Calculated mass for $C_{19}H_{25}NO_8$ (M+H)$^+$ 396.1. found by LC-MS 396.2.

Preparation of Compound 13 in FIG. 20. Compound 13 is tert-Butyl-(1S,2R)-2-[(benzylcarboxylate)-3-ethylthiocarboxylate)-1-metoxhycarbonyl)]propylcarbamate. DCC (5.9 g, 1.1 eq) was added to a solution of crude Compound 12 (10.4 g, 26.2 mmol), EtSH (2.15 mL, 1.1 eq) and 4-dimethylaminopyridine (DMAP) (0.32 g, 0.1 eq) dissolved in DCM (28 mL). After 6 hours the mixture was concentrated, re-dissolved in AcOEt (150 mL) washed with 1N HCl 2×, sat. NaCl 1×, dried over Na$_2$SO$_4$, filtered, concentrated and dried under high vacuum to yield Compound 13 as a brown oil (7.6 g), which was used without further purification in the next step. Calculated mass for $C_{21}H_{29}NO_7S$ (M+H)$^+$ 440.1. found by LC-MS 440.2.

Preparation of Compound 14 in FIG. 20. Compound 14 is (1S,2R)-2-[(benzyl-carboxylate)-3-ethylthiocarboxylate)-1-metoxhycarbonyl)]propylamine hydrochloride salt. Crude Compound 13 (7.6 g, 17.2 mmol) was dissolved in ethyl ether (8 mL), followed by addition of a 2N solution of HCl in diethyl ether (40 mL). The clear mixture was stirred at room temperature for 18 hours. The mixture was concentrated to give Compound 14 as an orange oil (7.5 g) which was used without further purification in the next step. Calculated mass for $C_{16}H_{21}NO_5S$ (M+H)$^+$ 338.1. found by LC-MS 338.2.

Preparation of Compound 15 in FIG. 20. Compound 15 is (1S,2R)-2-[(benzyl-carboxylate)-3-ethylthiocarboxylate)-1-metoxhycarbonyl)]propyl-L-N-Boc-Ala. Crude Compound 14 (6.6 g, 17.7 mmol), Boc-L-Ala-OH (3.7 g, 1.1 eq) and 2-(7-aza-1H-benzotriazol-1-yl)-1,1,3,3-tetramethyluronium hexafluoride (HATU) (12.1 g, 1.8 eq) were dissolved in ACN (150 mL). To this solution was added DIEA (6.1 mL, 2 eq) and the mixture was stirred at room temperature for 6 hours. The mixture was concentrated, re-dissolved in AcOEt (150 mL), washed with sat NH$_4$Cl 2×, sat. NaCl 1×, dried over Na$_2$SO$_4$, filtered, concentrated and dried under high vacuum to yield compound 15 as a brown oil (16.5 g of crude). Purification by flash chromatography using Hex;AcOEt (6:4) gave pure compound 15 (3.55 g, 40% yield). Calculated mass for $C_{24}H_{34}N_2O_8S$ (M+H)$^+$ 511.1. found by LC-MS 511.2.

Preparation of Compound 16 in FIG. 20. Compound 16 is (1S,2R)-2-[(benzyl-carboxylate)-3-formyl)-1-metoxhycarbonyl)]propyl-L-N-Boc-Ala. Triethylsilane (5.6 mL, 5 eq) was slowly added, under argon, to a solution of Compound 15 (3.5 g, 6.9 mmol) and Pd—C (0.6 g) dissolved in acetone (16 mL) in an ice bath (~4° C.). After addition of TES the reaction was stirred at 10-20° C. After 4 hours, thin layer chromatography (TLC) showed complete transformation. The reaction was filtered and concentrated to give an off-green oil. Purification by flash chromatography using Hex;AcOEt (6:4) gave pure Compound 16 (2.9 g, 93% yield). Calculated mass for $C_{22}H_{30}N_2O_8$ (M+H)$^+$ 452.1. found by LC-MS 452.2.

Preparation of Compound 17 in FIG. 20. Compound 17 is (3R,6S,7R)-7-(benzyloxy-carbonyl)-6-amino-(L-Boc-Ala)-hexahydro-5-oxo-2H-thiazolo[3,2-a]pyridine-3-carboxylic acid. In a high pressure vial crude Compound 16 (2 g, 4.55 mmol) was dissolved in dry pyridine (12 mL). To this mixture was added L-Cys-OH (0.88 g, 1.6 eq) followed by addition of 2.7 g of activated 4° A molecular sieves (powder). The mixture was stirred vigorously at room temperature for 4 hours. Dry-pyridine (10 mL) was added to the mixture, the vial was capped and the mixture stirred at 50° C. for 4 days. The mixture was then filtered through a bed of celite and washed with tetrahydrofuran (THF) and MeOH. The mixture was concentrated to give Compound 17 as yellow foam (1.6 g) which was used without further purification in the next step. Calculated mass for $C_{24}H_{31}N_3O_8S$ (M+H)$^+$ 522.1. found by LC-MS 522.2.

Preparation of Compound 18 in FIG. 20. Compound 18 is (3R,6S,7R)-7-(benzyloxy-carbonyl)-6-amino-(L-Ala)-hexahydro-5-oxo-2H-thiazolo[3,2-a]pyridine-3-carboxylic acid. In a round bottom flask crude Compound 17 (1.6 g, 3.1 mmol) was dissolved in dioxane (15 mL) followed by addition of 4M HCl. The mixture was stirred at room temperature and after 3 hours LCMS analysis showed complete conversion to the free amine. The mixture was concentrated, dissolved with DCM, MeOH, concentrated again and then dried under high vacuum to give the hydrochloride salt as a brownish semisolid (1.5 g) which was used without further purification in the next step. Calculated mass for $C_{24}H_{31}N_3O_8S$ (M+H)$^+$ 522.1. found by LC-MS 522.2.

This HCl salt was dissolved in DCM (14 mL) followed by addition of DIEA (2 mL, 3.5 eq) and FmocOSu (1.2 g, 1.1 eq) in portions as solid. The mixture was stirred for 3 hours showing complete transformation by LCMS. The mixture was concentrated, dissolved in AcOEt (60 mL), washed with 2N HCl 2×, brine, dried over Na$_2$SO$_4$, filtered and concentrated to give 2.1 g of a brownish oil. Purification by flash chromatography using Hex;AcOEt (5:95) followed by 100% MeOH gave pure compound 18 (0.821 g, 44% yield). Calculated mass for $C_{34}H_{33}N_3O_8S$ (M+H)$^+$ 644.1. found by LC-MS 644.2.

Example 11

Figure 21A:
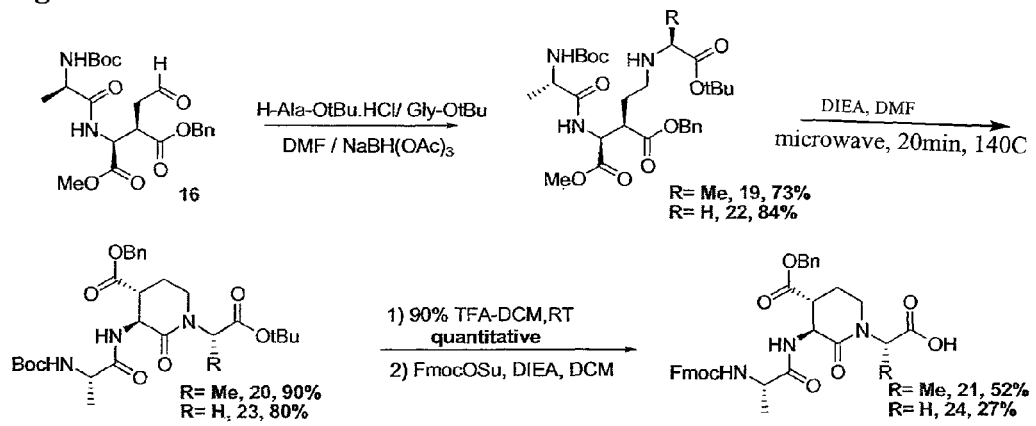
FIG. 21A is a process for preparing δ-lactam Asp-Gly-OH and Asp-Ala-OH, both of which are dipeptide mimetics that can be used to induce β-turn conformational constraint, for example, at the N-terminus in a GLP-1 receptor agonist compound.
Figure 21B:
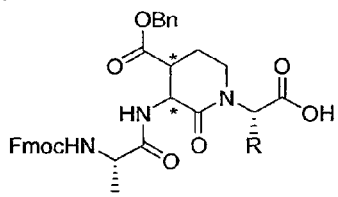
FIG. 21B is a generic structure of the compound that can be produced by the process shown in FIG. 21A. The skilled artisan can choose compounds with different stereochemistries during the reaction process to provide for various stereochemistries in the final product. * represents a chiral carbon atom.
Figure 22:
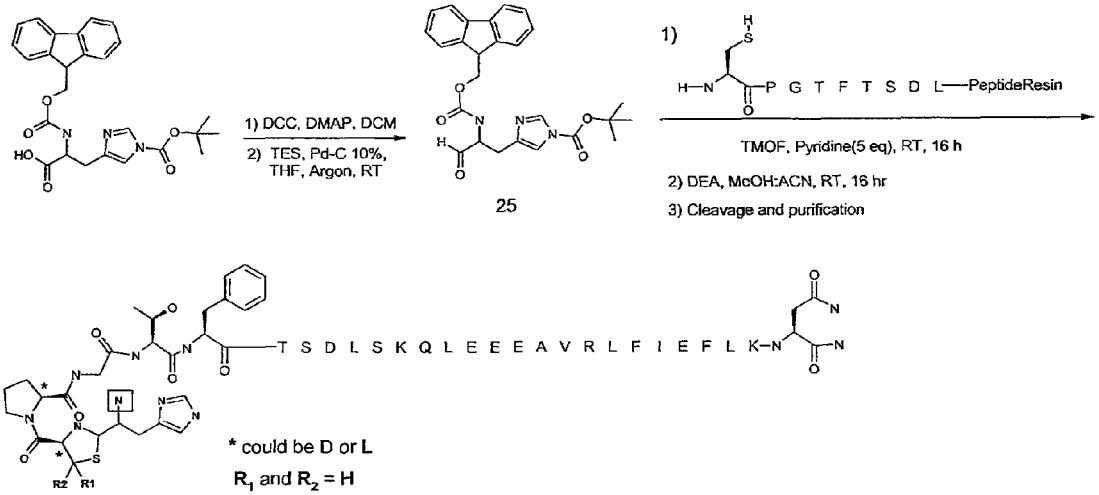
FIG. 22 is a process for preparing a peptide mimetic which can be used to induce a β-turn conformational constraint, for example, at the N-terminus in a GLP-1 receptor agonist compound.

Preparation of Compounds in FIG. 21

Preparation of compound 16 has been described in Example 10.

Preparation of Compound 19 in FIG. 21. Compound 19 is (1S,2R)-[2-(benzylcarboxylate)-3-formyl-4-(tert-butoxy-N-2-methyl acetyl)-1-(methoxycarbonyl)]butyl-L-N-Boc-Ala. Crude compound 16 (1.01 g, 2.24 mmol) and L-Ala-OtBu. HCl (0.449 g, 1.1 eq) were dissolved in DMF (4.5 mL) at room temperature. NaBH(OAc)$_3$ (0.95 g, 2 eq) was dissolved separately in DMF (4.5 mL) at room temperature, the two solutions were mixed and stirred at room temperature for about 2 hours. The reaction was washed with saturated NaHCO$_3$ solution 2×, water 1×, sat. NaCl 1×, dried over Na$_2$SO$_4$, filtered, concentrated to yield 0.92 g of Compound 19 as a colorless oil, which was used without further purification in the next step. Calculated mass for $C_{29}H_{45}N_3O_9$ (M+H)$^+$ 579.68. found by LC-MS 579.6.

Preparation of Compound 20 in FIG. 21. Compound 20 is (1S,2R)-tert-butyl-[4-(benzylcarboxylate)-3-(N-L-Boc-Ala)-2-oxopiperidine)-1-methyl-1-yl]acetate. Crude Compound 19 (0.550 g, 0.95 mmol) was dissolved in DMF (3 mL), DIEA (0.445 mL, 2 eq) was heated using microwaves at 140° C. for 20 min. The reaction was checked and then washed with 0.5M HCl 2×, water 1×, sat. NaCl 1×, dried over $Na_2SO_4$, filtered, concentrated to give 0.50 g of Compound 20 as a light brownish oil, which was used without further purification in the next step. Calculated mass for $C_{28}H_{41}N_3O_8$ $(M+H)^+$ 547.64. found by LC-MS 547.6.

Preparation of Compound 21 in FIG. 21. Compound 21 is (1S,2R)-[4-(benzyl-carboxylate)-3-(N-L-Fmoc-Ala)-2-oxopiperidine)-1-methyl-1-yl]acetic acid. Crude Compound 20 (0.501 g, 0.91 mmol) was dissolved in 5 mL of 20% TFA in DCM and stirred for about an hour at room temperature. The reaction was concentrated and then dried under high vacuum to give the corresponding TFA salt as brownish oil (0.47 g) which was used without further purification in the next step. Calculated mass for $C_{19}H_{25}N_3O_6$ $(M+H)^+$ 505.64. found by LC-MS 505.6

This TFA salt (0.47 g, 0.91 mmol) was dissolved in aqueous 10% $Na_2CO_3$ solution (12 mL) and DMF (4 mL), and cooled down to 0° C. A solution of FmocOSu (0.472 g, 1.5 eq) in DMF (8 mL) was added dropwise to the cold aqueous solution. After 5 minutes the ice bath was removed and the reaction was stirred overnight, quenched by adding 40 mL water followed by washings with AcOEt. The aqueous layer was acidified using 2N HCl (pH=2) and washed with AcOEt 3×, NaCl 1×, dried over $Na_2SO_4$, filtered and concentrated. Purification was done by washing the crude compound with Hex:AcOEt (6:4) 2× at room temperature to give Compound 21 as light colored oil (0.290 g, 52% yield). Calculated mass for $C_{34}H_{35}N_3O_8$ $(M+H)^+$ 613.24. found by LC-MS 613.2.

Preparation of Compound 22 in FIG. 21. Compound 22 is (1S,2R)-[2-(benzyl-carboxylate)-3-(formyl)-4-(tert-butoxy-N-acetyl)-1-(methoxycarbonyl)]butyl-L-N-Boc-Ala. Crude compound 16 (1.01 g, 2.24 mmol) and AcOH. $NH_2$-Gly-OtBu (0.478 g, 1.1 eq) were dissolved in dry DMF (4.5 mL) at room temperature. $NaBH(OAc)_3$ (0.95 g, 2 eq) was dissolved separately in dry DMF (4.5 mL) at room temperature, the two solutions were mixed and stirred at room temperature for about 2 hours. The reaction was washed with saturated $NaHCO_3$ solution 2×, water 1×, sat. NaCl 1×, dried over $Na_2SO_4$, filtered and concentrated to yield 1.09 g of Compound 22 as a colorless oil, which was used without further purification in the next step. Calculated mass for $C_{28}H_{43}N_3O_9$ $(M+H)^+$ 565.68. found by LC-MS 565.3.

Preparation of Compound 23 in FIG. 21. Compound 23 is (1S,2R)-tert-butyl-[4-(benzylcarboxylate)-3-(N-L-Boc-Ala)-2-oxopiperidine)-1-yl]acetate. Crude compound 22 (0.550 g, 0.95 mmol) was dissolved in DMF (3 mL), DIEA (0.445 mL, 2 eq) and then heated using microwaves at 140° C. for 20 min (Biotage™, Initiator8). The reaction was checked by LCMS. The reaction crude was washed with 0.5M HCl 2×, water 1×, sat. NaCl 1×, dried over $Na_2SO_4$, filtered and concentrated to yield 0.41 g of Compound 23 as a light brownish oil, which was used without further purification in the next step. Calculated mass for $C_{27}H_{39}N_3O_8$ $(M+H)^+$ 533.64. found by LC-MS 533.6.

Preparation of Compound 24 in FIG. 21. Compound 24 is (1S,2R)-[4-(benzyl-carboxylate)-3-(N-L-Fmoc-Ala)-2-oxopiperidine)-1-yl]acetic acid. Crude compound 23 (0.41 g, 0.76 mmol) was dissolved in 5 mL of 20% TFA in DCM; reaction was stirred for about an hour at room temperature. The reaction was concentrated and then dried under high vacuum to give the corresponding TFA salt as a brownish oil (0.45 g) which was used without further purification in the next step. Calculated mass for $C_{18}H_{23}N_3O_6$ $(M+H)^+$ 491.3. found by LC-MS 491.4

This TFA salt (0.45 g, 0.92 mmol) was dissolved in aqueous 10% $Na_2CO_3$ solution (12 mL) and DMF (4 mL), and cooled down to 0° C. A solution of FmocOSu (0.472 g, 1.5 eq) in DMF (8 mL) was added dropwise to the cold aqueous solution. After 5 min, the ice bath was removed and the reaction was stirred overnight, then quenched by adding about 40 mL water, followed by washings with AcOEt. The aqueous layer was acidified using 2N HCl (pH=2) and washed with AcOEt 3×, NaCl 1×, dried over $Na_2SO_4$, filtered, concentrated. Purification was done by washing the crude compound with Hex:AcOEt (6:4) 2× at room temperature giving Compound 24 as light colored oil (0.15 g, 27% yield). Calculated mass for $C_{33}H_{33}N_3O_8$ $(M+H)^+$ 599.6. found by LC-MS 599.4.

Example 12

Preparation of Compounds in FIGS. 1A, 2A, and 5A

The compound in FIG. 1A may be prepared following the methods described, e.g., in U.S. Pat. No. 6,872,700, the disclosure of which is incorporated by reference. The compounds in FIGS. 2A and 5A may be prepared following the methods described, e.g., in WO 2007/139941, the disclosure of which is incorporated by reference.

Example 13

Preparation of Compounds in FIGS. 1B-C, 2B-U, 3A-G, 5B-G, 6A-E, 10A-I, 11A-C, 12, 13A-B, 14B-C, 14E-R For each compound in FIGS. 1B, 1C, 2B, 2C, 2D, 2E, 2F, 2G, 2H, 2I, 2J, 2K, 3A, 3B, 3C, 3D, 3E, 3F, 3G, 5B, 5C, 5D, 6A, 6B, 6C, 6D, and 6E, a calculated 100 μmol of Fmoc-Ser (OtBu)-Wang resin or Fmoc Rink amide resin was weighed into a reaction vessel in a Symphony peptide synthesizer, and peptide elongation was carried out following standard Fmoc peptide synthesis protocol. If an unnatural amino acid was used at position 2 this was incorporated manually in a polypropylene syringe. Cleavage of the peptide from the resin was done with 10 mL TFA/$H_2O$/PhOH/TIPS (95:2:2:1), then precipitated by methyl-tert-Butyl ether. The crude was dissolved and applied to a reverse-phase HPLC column ($C_{18}$, 20-50% $CH_3CN$ in 0.1% TFA/$H_2O$ over 30 min gradient) to afford the titled compounds as white powders. All characterized by LC-MS. The compounds in FIGS. 2L-U, 5E-G, 10A-I, 13B, 14B-C and 14E-K will be prepared following the methods described in this example.

With respect to the compounds in FIGS. 14L-R, a calculated 100 μmol of Fmoc-Rink-amide resin was weighed into a reaction vessel in a Symphony peptide synthesizer, and peptide elongation was carried out following standard Fmoc peptide synthesis protocol. If an unnatural amino acid was used at position 2 this was incorporated manually in a polypropylene syringe. Only for the compounds in FIGS. 14N-O, this procedure was carried out under the following microwave-assisted conditions: A microwave vial was loaded with the corresponding peptide-resin intermediate (0.3 g, 0.14 mmol), Fmoc-AA-OH (4 eq), PyBrop (0.32 g, 4.8 eq), 2,6-lutidine (0.25 mL, 15 eq), dichloroethane (DCE) (2-3 mL) and DMF (about 0.3 mL). The vial was capped and heated with microwaves (Biotage™, Initiator8) at 100° C. for 11 min. The resin was filtered, washed with DCE and MeOH. Cleavage of the peptide from the resin was done with 10 mL TFA/$H_2O$/PhOH/TIPS (95:2:2:1), then precipitated by methyl-tert-Butyl ether. The crude was dissolved and applied to a reverse-phase HPLC column ($C_{18}$, 20-50% $CH_3CN$ in 0.1% $TFA/H_2O$ over 30 min gradient) to afford the titled compounds as white powders. All characterized by LC-MS.

Example 14

Preparation of Compounds in FIGS. 8A-H

For the compounds in FIGS. 8B, 8C, 8D, 8E, 8F, 8G, and 8H, a calculated 100 mol of Fmoc-Ser(OtBu)-Wang or Fmoc-Rink-amide resin was weighed into a reaction vessel in a Symphony peptide synthesizer, and the peptide elongation was carried out following standard Fmoc peptide synthesis protocol. The corresponding L- or D-Cys(Trt)-OH was introduced at positions 2 and 4. Cleavage of the peptide from the resin with 10 mL $TFA/H_2O/PhOH/TIPS$ (95:2:2:1) then precipitated by methyl-tert-Butyl ether. The crude peptides were dried overnight under high vacuum.

Disulfide cyclization: Clear-OX resin (0.39 g, 3× molar excess) was swollen on DCM for 45 min at room temperature, then washed with DCM 2×, DMF 3×, MeOH 3×, deionized water 3× and finally $H_2O:ACN$ (1:1) 3×. The corresponding crude peptide (0.1 g) was dissolved in degassed 1:1 v/v solution of 0.1M $NH_4OAc$ buffer (pH=6.5)/ACN. The peptide solution was then added to the pre-swollen Clear-OX resin and the slurry was shacked at room temperature. After 2-3 hours the cyclization was complete. The resin was washed with a small amount of $ACN/H_2O$ (1:1) solution, the filtrate concentrated to remove volatiles and then lyophilized. The crude was dissolved and applied to a reverse-phase HPLC column ($C_{18}$, 20-50% $CH_3CN$ in 0.1% $TFA/H_2O$ over 30 min gradient) to afford the titled compounds as white powders. All characterized by LC-MS. The compound in FIG. 8A will be prepared following the methods described in this example.

Example 15

Preparation of Compounds in FIGS. 9A-H

For each compound in FIGS. 9A, 9B, 9C, 9D, 9E, 9G, and 9H, a calculated 100 μmol of Fmoc-Rink amide resin was weighed into a reaction vessel in a Symphony peptide synthesizer, and the peptide elongation was carried out following standard Fmoc peptide synthesis protocol. The amino acid at position 2 of all these compounds was introduced by special coupling conditions. A microwave vial was loaded with the corresponding peptide-resin intermediate (0.3 g, 0.14 mmol), Fmoc-AA-OH (4 eq), PyBrop (0.32 g, 4.8 eq), 2,6-lutidine (0.25 mL, 15 eq), dichloroethane (DCE) (2-3 mL) and DMF (~0.3 mL). The vial was capped and heated with microwaves (Biotage™, Initiator8) at 100° C. for 11 min. The resin was filtered, washed with DCE and MeOH. For some compounds the above process was repeated twice. The resin is then treated in a cycle of deprotection, coupling with Fmoc-His(Trt)-OH, HBTU and HOBt, deprotection. Cleavage of the peptide from the resin was done with 10 mL $TFA/H_2O/PhOH/TIPS$ (95:2:2:1), then precipitated by methyl-tert-Butyl ether. The crude was dissolved and applied to a reverse-phase HPLC column ($C_{18}$, 20-50% $CH_3CN$ in 0.1% $TFA/H_2O$ over 30 min gradient) to afford the titled compounds as white powders. All characterized by LC-MS. The compound in FIG. 9F will be prepared following the methods described in this example.

Example 16

In Vitro Assay

The compounds shown in Table 1 below were analyzed in an in vitro functional assay at the GLP-1 receptor. The assay was conducted as follows: Membrane fractions were prepared from confluent cultures of RIN m5f cells. Compounds were serially diluted with an assay buffer, and then added to a 96-well assay plate containing RIN m5f cell membranes in an ATP/GTP mixture. Cyclase activities were determined by measuring the production of cAMP induced through GLP-1 receptor activation. Quantification of cAMP production was achieved through a competitive chemiluminescence assay with a biotinylated-cAMP probe using Perkin Elmer Fusion™-Alpha Microplate Analyzer (AlphaScreen™ technology). The compound $EC_{50}$ values were obtained through fitting the concentration-response curves to a four-parameter logistic equation within GraphPad PRISM® software. The results of the assay are presented in Table 1 below.

Example 17

In Vivo Assay

Some compounds shown in Table 1 below were analyzed in an in vivo basal glucose lowering assay using the following procedure: A subcutaneous injection of either 200 μl phosphate-buffered saline (PBS) vehicle or test article was given immediately following baseline glucose (t=0) to NIH/Swiss female mice. Tail blood glucose samples were measured at t=2 and 4 hours post dose using a OneTouch® Ultra® (LifeScan, Inc., a Johnson & Johnson Company, Milpitas, Calif.). Body weight was measured daily. Significant test sample effects were identified by ANOVA ($p<0.05$), followed by Dunnett's post test using GraphPad Prism version 4.00 for Windows (GraphPad Software, San Diego Calif.). The results are presented in Table 1 below.

TABLE 1

| Compound in Figure | Cyclase GLP-1 Receptor $EC_{50}$ (nM) | In Vivo Glucose-Lowering Assay |
| --- | --- | --- |
| 1A | 0.01 | not tested |
| 1B | 0.004 | not tested |
| 1C | 0.029 | not tested |
| 2A | 0.008 | greater than 3 hours |
| 2B | 0.0089 | more than 4 hours |
| 2C | 6 | not tested |
| 2D | 0.04 | not tested |
| 2E | 2.15 | not tested |
| 2F | 0.027 | more than 4 hours |
| 2G | 0.89 | not tested |
| 2H | 0.124 | not tested |
| 2I | 0.054 | more than 4 hours |
| 2J | 7.2 | not tested |
| 2K | 0.29 | similar to GLP-1 |
| 3A | 0.007 | more than 4 hours |
| 3B | 0.007 | more than 2 hours |
| 3C | 0.022 | not tested |
| 3D | 1.03 | not tested |
| 3E | 0.06 | more than 2 hours |
| 3F | 1.089 | not tested |
| 3G | 0.065 | similar to GLP-1 |
| 5A | 1.83 | more than 4 hours |
| 5B | 0.53 | more than 4 hours |
| 5C | 1.056 | not tested |
| 5D | 10.5 | not tested |
| 6A | 0.144 | similar to GLP-1 |
| 6B | 0.52 | not tested |
| 6C | 151.9 | not tested |
| 6D | 0.282 | not tested |
| 6E | 0.60 | more than 4 hours |
| 8B | 1.26 | similar to GLP-1 |
| 8C | 968.6 | not tested |
| 8D | 106.2 | not tested |
| 9A | 0.21 | not tested |
| 9B | 0.03 | more than 4 hours |

TABLE 1-continued

| Compound in Figure | Cyclase GLP-1 Receptor EC$_{50}$ (nM) | In Vivo Glucose-Lowering Assay |
|---|---|---|
| 9C | 0.05 | more than 4 hours |
| 9D | 0.01 | more than 4 hours |
| 9E | 133 | not tested |
| 9F | 0.07 | more than 4 hours |
| 9G | 1.9 | not tested |
| 9H | 0.1 | not tested |
| 11A | 0.155 | not tested |
| 11B | 0.007 | not tested |
| 11C | 0.011 | not tested |
| 12 | 0.028 | not tested |
| 13 | 0.274 | not tested |
| 14J | 0.054 | not tested |
| 14K | 3.5 | not tested |
| 14L | 0.05 | not tested |
| 14M | 0.2 (partial agonist) | not tested |
| 14N | 0.004 | not tested |
| 14O | 0.24 | not tested |
| 14P | 0.25 | not tested |
| 14Q | 0.02 | not tested |
| 14R | 0.41 (partial agonist) | not tested |
| 15A | 0.57 | inactive |
| 15B | 1000 | not tested |
| 15C | 2.46 | inactive |
| 15D | 1.7 | inactive |
| 16A | 0.52 | inactive |
| 16B | 0.18 | similar to GLP-1 |
| 16C | 1.1 | inactive |
| 16D | 1 | inactive |
| 16E | 1 | inactive |
| 16F | 0.61 | about 30 minutes |
| 16G | 56 | not tested |
| 16H | 1000 | not tested |
| 17A | 105 | not tested |
| 17B | 668 | not tested |
| 17C | 10,000 | not tested |

Example 18

Preparation of Compounds in FIGS. 17A-F

A calculated 100 μmol of Rink amide resin was weighed into a reaction vessel in a Symphony peptide synthesizer, and the peptide elongation was carried out following standard Fmoc peptide synthesis protocol up to residue Pro$^3$. The resulting peptide-resin intermediate (0.3 g, 0.0927 mmol) was swollen in DCM with around 5% DMF and to the slurry was added Fmoc-Cys(Trt)-OH (0.351 g, 4 eq), followed by Bromo-tris-pyrrolidino-phosphonium hexafluoro-phosphate (PyBrop) (0.34 g, 4.8 eq) and 2,6-lutidine (0.27 mL, 15 eq). The vial was capped and heated in a microwave apparatus (Biotage Initiator8) at 100° C. for 11 min. The resin was filtered and washed with DMF 6×, treated with 20% piperidine in DMF 2×25 min and washed with DMF 6×, DCM 4× followed by treatment with 2% TFA/1.5% TIS in DCM 4×10 min. then washed with DCM 4×, DMF 2× and TMOF 3×. In a polypropylene syringe the resin is swollen in TMOF, followed by addition of compound 25 (0.2 g, 3 eq) and dry pyridine (0.06 mL, 5 eq). The resin was shaken at room temperature for 16 hours, followed by washings with TMOF 3×, DCM 3×, MeOH 3× and dried under high vacuum. Cleavage of the peptide from the resin was carried out with 10 ml TFA/H$_2$O/PhOH/TIPS (95:2:2:1) (TFA is trifluoroacetic acid; TIPS is triisopropyl-silyl), precipitated by methyl-tert-Butyl ether. The residue was dissolved in 0.8 ml of MeOH and 0.8 ml of ACN. To this solution 0.1 ml of DEA were added and the mixture stirred at room temperature overnight. The resulting residue was applied to a reverse-phase high performance liquid chromatography (HPLC) column (C$_{18}$, 20-50% CH$_3$CN in 0.1% TFA/H$_2$O over 30 min gradient) to afford compound 17A as a white powder (5.3 mg, 3%): Retention time in reverse phase-high performance liquid chromatography (RP-HPLC) (C$_{18}$, 5-75% CH$_3$CN in 0.1% TFA/H$_2$O over 15 min) is 8.71 min; Calculated mass for C$_{146}$H$_{228}$N$_{38}$O$_{43}$S (M+H)$^+$ 3235.74. found by liquid chromatography/mass spectrometry (LC-MS) 1079.6 (M+3H)$^{3+}$, 1619.9 (M+2H)$^{2+}$.

The synthesis of compounds 17B and 17C was performed similar as reported above for compound 17A, with the difference of using Fmoc-D-Cys(Trt)-OH and Fmoc-Pen-OH, respectively. After purification compound 17B was obtained as a white powder (8 mg, 7%): Retention time in reverse phase-high performance liquid chromatography (RP-HPLC) (C$_{18}$, 5-75% CH$_3$CN in 0.1% TFA/H$_2$O over 15 min) is 8.55 min; Calculated mass for C$_{146}$H$_{228}$N$_{38}$O$_{43}$S (M+H)$^+$ 3235.74. found by liquid chromatography/mass spectrometry (LC-MS) 1079.6 (M+3H)$^{3+}$, 1619.9 (M+2H)$^{2+}$. After purification compound 17C was obtained as a white powder (1.5 mg, 3%): Retention time in reverse phase-high performance liquid chromatography (RP-HPLC) (C$_{18}$, 5-75% CH$_3$CN in 0.1% TFA/H$_2$O over 15 min) is 8.55 min; Calculated mass for C$_{148}$H$_{232}$N$_{38}$O$_{43}$S (M+H)$^+$ 3263.79. found by liquid chromatography/mass spectrometry (LC-MS) 1089.6 (M+3H)$^{3+}$, 1632.9 (M+2H)$^{2+}$.

Example 19

Preparation of Compound 25

In a round bottom flask Fmoc-His(Boc)-OH (4 g, 1 eq) was dissolved in DCM (50 mL). To this solution was added DCC (1.9 g, 1.1 eq), EtSH (0.7 mL, 1.1 eq) and DMAP (0.102 g, 0.1 eq). The mixture was stirred at room temperature for 6 h. The reaction mixture was filtered and the solution concentrated to yield 4.9 g of an off-white solid. The crude product was purified by flash chromatography using Hex:AcOEt (1:1). After concentration of the pure fractions the corresponding thioester was obtained as a clear oil (3.6 g, 84%). The thioester (0.69 g, 1 eq) was dissolved in THF (11 mL) and stirred under Argon atmosphere for few minutes. To this solution was added Pd—C (0.180 g) and the mixture stirred under Argon for 10 min followed by dropwise addition of TES (0.75 mL, 3.5 eq) and the mixture stirred at room temperature. After 4 h one more equivalent of TES was added, one hour later the crude mixture was filtered through a bed of silica/celite and washed with THF. The filtrate was concentrated to give a dark brown oil, which was purified by flash chromatography in a short (20 mL) silica gel column using Hex:AcOEt (2:8). After concentration of the pure fractions compound 25 was obtained as a clear semisolid (0.26 g, 50%).

Example 20

Modified Exendin Peptides

N-Terminus conformationally constrained GLP-1 receptor agonist compounds described herein were covalently linked to one or more polyethylene glycol and/or fatty acids, as described herein. In particular, the following twelve compounds 23A-L were prepared:
Compound 23A: 4-imidazopropionyl-dAla-PGTFTSDLSK$^{12}$QMEEEAVRLFIE-WLKNGGPSSGAP- PPS-NH$_2$, wherein K$^{12}$ was modified with —C(═O)—CH$_2$(OCH$_2$CH$_2$)$_2$NH—C(═O)CH$_2$—(OCH$_2$CH$_2$)$_2$NH—C(═O)—(CH$_2$)$_6$—CH$_3$ (SEQ ID NO:105).

Compound 23B: 4-imidazopropionyl-dAla-PGTFTSDLSK$^{12}$QMEEEAVRLFIE-WLKNGGPSSGAP-PPS-NH$_2$, wherein K$^{12}$ was modified with —C(═O)—CH$_2$(OCH$_2$CH$_2$)$_2$NH—C(═O)CH$_2$(OCH$_2$CH$_2$)$_2$NH—C(═O)—CH(NH$_2$)—(CH$_2$)$_7$—CH$_3$(SEQ ID NO:106).

Compound 23C: 4-imidazopropionyl-dAla-PGTFTSDLSK$^{12}$QMEEEAVRLFIE-WLKNGGPSSGAP-PPS-NH$_2$, wherein K$^{12}$ was modified with —C(═O)—CH$_2$(OCH$_2$CH$_2$)$_2$NH—C(═O)CH$_2$(OCH$_2$CH$_2$)$_2$NH—C(═O)—CH[NH—C(═O)(CH$_2$)$_6$CH$_3$]-(CH$_2$)$_7$—CH$_3$(SEQ ID NO:107).

Compound 23D: 4-imidazopropionyl-dAla-PGTFTSDLSK$^{12}$QMEEEAVRLFIE-WLKNGGPSSGAP-PPS-NH$_2$, wherein K$^{12}$ was modified with —C(═O)—CH$_2$(OCH$_2$CH$_2$)$_2$NH—C(═O)CH$_2$(OCH$_2$CH$_2$)$_2$NH—C(═O)—CH$_2$CH$_2$—CH[C(OH)(═O)]—NH—C(═O)—(CH$_2$)$_{16}$-[C(OH)(═O)](SEQ ID NO:108).

Compound 23E: 4-imidazopropionyl-dAla-PGTFTSDL-SKQMEEEAVRLFIEW-LK$^{27}$NGGPSSGAPPPS-NH$_2$, wherein K$^{27}$ was modified with —C(═O)—CH$_2$(OCH$_2$CH$_2$)$_2$NH—C(═O)CH$_2$(OCH$_2$CH$_2$)$_2$NH—C(═O)—(CH$_2$)$_6$—CH$_3$(SEQ ID NO:109).

Compound 23F: 4-imidazopropionyl-dAla-PGTFTSDL-SKQMEEEAVRLFIEW-LK$^{27}$NGGPSSGAPPPS-NH$_2$, wherein K$^{27}$ was modified with —C(═O)—CH$_2$(OCH$_2$CH$_2$)$_2$NH—C(═O)CH$_2$(OCH$_2$CH$_2$)$_2$NH—C(═O)—CH(NH$_2$)—(CH$_2$)$_7$—CH$_3$(SEQ ID NO:110).

Compound 23G: 4-imidazopropionyl-dAla-PGTFTSDL-SKQMEEEAVRLFIEW-LK$^{27}$NGGPSSGAPPPS-NH$_2$, wherein K$^{27}$ was modified with —C(═O)—CH$_2$(OCH$_2$CH$_2$)$_2$NH—C(═O)CH$_2$(OCH$_2$CH$_2$)$_2$NH—C(═O)—CH[NH—C(═O)(CH$_2$)$_6$CH$_3$]—(CH$_2$)$_7$—CH$_3$ (SEQ ID NO.111).

Compound 23H: 4-imidazopropionyl-dAla-PGTFTSDL-SKQMEEEAVRLFIEW-LK$^{27}$NGGPSSGAPPPS-NH$_2$, wherein K$^{27}$ was modified with —C(═O)—CH$_2$(OCH$_2$CH$_2$)$_2$NH—C(═O)CH$_2$(OCH$_2$CH$_2$)$_2$NH—C(═O)—CH$_2$CH$_2$—CH[C(OH)(═O)]—NH—C(═O)—(CH$_2$)$_{16}$-[C(OH)(═O)](SEQ ID NO:112).

Compound 23I: 4-imidazopropionyl-dAla-PGTFTSDL-SKQMEEEAVRLFIEWLKN-GGPSSGAPPPS$^{39}$, wherein S$^{39}$ was modified with -Lys(NH$_2$)—C(═O)—CH$_2$(OCH$_2$CH$_2$)$_2$NH—C(═O)CH$_2$(OCH$_2$CH$_2$)$_2$NH—C(═O)—(CH$_2$)$_6$—CH$_3$(SEQ ID NO:113).

Compound 23J: 4-imidazopropionyl-dAla-PGTFTSDL-SKQMEEEAVRLFIEWLKN-GGPSSGAPPPS$^{39}$, wherein S$^{39}$ was modified with -Lys(NH$_2$)—C(═O)—CH$_2$(OCH$_2$CH$_2$)$_2$NH—C(═O)CH$_2$(OCH$_2$CH$_2$)$_2$NH—C(═O)—CH(NH$_2$)—(CH$_2$)$_7$—CH$_3$(SEQ ID NO:114).

Compound 23K: 4-imidazopropionyl-dAla-PGTFTSDL-SKQMEEEAVRLFIEWLKN-GGPSSGAPPPS$^{39}$, wherein S$^{39}$ was modified with -Lys(NH$_2$)—C(═O)—CH$_2$(OCH$_2$CH$_2$)$_2$NH—C(═O)CH$_2$(OCH$_2$CH$_2$)$_2$NH—C(═O)—CH[NH—C(═O)(CH$_2$)$_6$CH$_3$]—(CH$_2$)$_7$—CH$_3$ (SEQ ID NO:115).

Compound 23L: 4-imidazopropionyl-dAla-PGTFTSDL-SKQMEEEAVRLFIEWLKN-GGPSSGAPPPS$^{39}$, wherein S$^{39}$ was modified with —C(═O)—CH$_2$(OCH$_2$CH$_2$)$_2$NH—C(═O)CH$_2$(OCH$_2$CH$_2$)$_2$NH—C(═O)—CH$_2$CH$_2$—CH[C(OH)(═O)]—NH—C(═O)—(CH$_2$)$_{16}$—[C(OH)(═O)] (SEQ ID NO:116).

For each of Compound Nos. 23A-L above, a calculated 100 μmol of Fmoc-Rink-amide resin was weighed into a reaction vessel in a Symphony peptide synthesizer, and peptide elongation was carried out following standard Fmoc peptide synthesis protocol. The dAla at position 2 was incorporated manually in a polypropylene syringe. The orthogonal protection (alloc group) of the side chain group (Lys$^{12}$, Lys$^{27}$ or Lys$^{40}$) was performed as follows: The peptide-resin was swollen in DCM and dimethylamino borane-complex (6 eq) followed after about 3 minutes by tetrakis(triphenylphosphine)palladium(0) (0.1 eq). The resin was shaken for 15 minutes, washed with DCM 3× and the process repeated. Then, the resin was washed with DCM 3×, 10% DIEA in DCM 2×, DCM 3× and MeOH 2×. At this point, the peptide-resin gave a positive chloranil test. The resulting peptide-resin intermediate (0.3 g, 0.0927 mmol) was swollen in DMF and to the slurry was added the corresponding polyethylene glycol (2.2 eq), followed by HBTU (0.035 g, 2.2 eq), HOBt (0.03 g, 2.2 eq) and NMM (0.04 mL, 4.4 eq). After 3 hours, the resin was washed with DMF 6×, treated with 20% piperidine in DMF 2×25 min and washed with DMF 6×. The above cycle was repeated with a second Fmoc-(polyethylene glycol)-OH in most cases. The coupling of the corresponding fatty acid chain was done using two different microwave-assisted methods: the corresponding acyl chloride (5 eq) and NMM (7 eq) were added to the resin swollen in a 1:1 DMF:DCM mixture, and then heated using microwaves at 75° C. for 20 min (Biotage™, Initiator8); or the corresponding carboxylic or dicarboxylic acid (5 eq), HOAt (5 eq) and DIC (5 eq) were added to the slurry resin on DMF, and then heated using microwaves at 75° C. for 15 min (Biotage™, Initiator8). Cleavage of the peptide from the resin was done with 10 mL TFA/H$_2$O/PhOH/TIPS (95:2:2:1), then precipitated by methyl-tert-Butyl ether. The crude was dissolved and applied to a reverse-phase HPLC column (C$_{18}$, 20-50% CH$_3$CN in 0.1% TFA/H$_2$O over 30 min gradient) to afford the titled compounds as white powders. All were characterized by LC-MS.

Each of these compounds was analyzed in an in vitro functional assay at the GLP-1 receptor following the methods described in Example 16. The results are in Table 2:

TABLE 2

| Compound | Cyclase GLP-1 Receptor EC$_{50}$ (nM) |
|---|---|
| 23A | 0.027 |
| 23B | 0.027 |
| 23C | 0.06 |
| 23D | 0.22 |
| 23E | 0.3 |
| 23F | 0.1 |
| 23G | 0.7 |
| 23H | 0.08 |
| 23I | 0.01 |
| 23J | 0.01 |
| 23K | 0.02 |
| 23L | 0.185 |

Example 21

Modified Exendin Peptides

N-Terminus conformationally constrained GLP-1 receptor agonist compounds described herein were covalently linked to one or more biotin, as described herein. In particular, the following compounds 24A-L were prepared:

Compound 24A:
His-dAla-PGTFTSDLSKQMEEEAVRLFIEWL-Lys(biotin)-

NGGPSSGAPPS-Lys[(NH₂)(biotin)].
(SEQ ID NO: 117).

Compound 24B:
4-imidazopropionyl-GEGTFTSDLSKQMEEEAVRLFIEWL-

Lys(biotin)-NGGPSSGAPPS-Lys[(NH₂)(biotin)].

Compound 24C:
4-imidazopropionyl-GEGTFTSDLSKQMEEEAVRLFIEWLKN-

Lys[(NH₂)(biotin)].

Compound 24D:
4-imidazopropionyl-APGTFTSDLSKQMEEEAVRLFIEWLKN-

Lys[(NH₂)(biotin)].

Compound 24E:
His-dAla-PGTFTSDLSKQMEEEAVRLFIEWLKNGGPSSGAPPPS-

Lys(NH₂)-(O-CH₂-CH₂)₂-KAKAEAEAKAKAEAEA-biotin

Compound 24F:
His-dAla-PGTFTSDLSKQMEEEAVRLFIEWLE[-(O-CH₂-CH₂)₂-

(biotin)].-NGGPSSGAPPPS-NH₂.

Compound 24G:
His-dAla-PGTFTSDLSEK[-(O-CH₂-CH₂)₂-(biotin)]-

QMEEEAVRLFIEWLKNGGPSSGAPPPS-NH₂.

Compound 24E: His-dAla-PGTFTSDLSKQMEEEAVR-LFIEWLKNGGPSSGAPPPS-Lys(NH₂)—(O—CH₂-CH₂)₂-KAKAEAEAKAKAEAEA-biotin (SEQ ID NO:118).

Compound 24F: His-dAla-PGTFTSDLSKQMEEEAVR-LFIEWLE[—(O—CH₂-CH₂)₂-biotin]-NGGPSSGAPPPS-NH₂ (SEQ ID NO:119).

Compound 24G:. His-dAla-PGTFTSDLSEK[—(O—CH₂—CH₂)₂-biotin]-QMEEEAVRLFIEWLKNGGPSS-GAPPPS-NH₂ (SEQ ID NO:120).

For each of Compound Nos. 24A-G above, a calculated 100 μmol of Fmoc-Rink-amide resin was weighed into a reaction vessel in a Symphony peptide synthesizer, and peptide elongation was carried out following standard Fmoc peptide synthesis protocol. If an unnatural amino acid was used at position 2 this was incorporated manually in a polypropylene syringe. The orthogonal protection (alloc group) of the side chain group (Lys²⁷, Lys²⁸ or Lys⁴⁰) was performed as follows: The peptide-resin was swollen in DCM and dimethylamino borane-complex (6 eq) followed after about 3 minutes by tetrakis(triphenylphosphine)palladium(0) (0.1 eq). The resin was shaken for 15 min, washed with DCM 3× and the process repeated. Then, the resin was washed with DCM 3×, 10% DIEA in DCM 2×, DCM 3× and MeOH 2×. At this point, the peptide-resin gave a positive chloranil test. The biotin moiety (one or two) was coupled to the free amino group using the standard solid-phase coupling conditions described above (HBTU, HOBt, NMM). Cleavage of the peptide from the resin was done with 10 mL TFA/H₂O/PhOH/TIPS (95:2:2:1), then precipitated by methyl-tert-Butyl ether. The crude was dissolved and applied to a reverse-phase HPLC column (C₁₈, 20-50% CH₃CN in 0.1% TFA/H₂O over 30 min gradient) to afford the titled compounds as white powders. All were characterized by LC-MS.

Each of these compounds was analyzed in an in vitro functional assay at the GLP-1 receptor following the methods described in Example 16. The results are in Table 3:

TABLE 3

| Compound | Cyclase GLP-1 Receptor EC₅₀ (nM) |
| --- | --- |
| 24A | 0.04 |
| 24B | 0.03 |
| 24C | 0.07 |
| 24D | 0.77 |
| 24E | 0.06 |
| 24F | 0.06 |
| 24G | 0.01 |

Example 22

Compounds of FIG. 10

With respect to FIG. 10, the following compounds 10J-10N were made:

10J: 4-imidazopropionyl-GPGTFTSDLSKQLEEEAVRLFIEWLKNGGPSSGAPPPS-NH₂

10K: 4-imidazopropionyl-dAla-PGTFTSDLSKQLEEEAVRLFIEWLKNGGPSSGAPPPS-NH₂
(SEQ ID NO: 121).

10L: 4-imidazopropionyl-Aib-PGTFTSDLSKQLEEEAVRLFIEWLKNGGPSSGAPPPS-NH₂

10M: 4-imidazopropionyl-GEGTFTSDLSKQLEEEAVRLFIEWLKQGGPSKEIIS-OH

10N: 4-imidazopropionyl-dAla-PGTFTSDLSKQLEEEAVRLFIEWLKQGGPSKEIIS-OH
(SEQ ID NO: 122).

For each of Compounds 10J-N, a calculated 100 μmol of Fmoc-Rink-amide resin was weighed into a reaction vessel in a Symphony peptide synthesizer, and peptide elongation was carried out following standard Fmoc peptide synthesis protocol. If an unnatural amino acid was used at position 2 this was incorporated manually in a polypropylene syringe. Only for the compound in FIG. 10L, this procedure was carried out under the following microwave-assisted conditions: a microwave vial was loaded with the corresponding peptide-resin intermediate (0.3 g, 0.14 mmol), Fmoc-AA-OH (4 eq), PyBrop (0.32 g, 4.8 eq), 2,6-lutidine (0.25 mL, 15 eq), dichloroethane (DCE) (2-3 mL) and DMF (~0.3 mL). The vial was capped and heated with microwaves (Biotage™, Initiator8) at 100° C. for 11 min. The resin was filtered, washed with DCE and MeOH. Cleavage of the peptides from the resins was done with 10 mL TFA/H₂O/PhOH/TIPS (95:2:2:1), then precipitated by methyl-tert-Butyl ether. The crude was dissolved and applied to a reverse-phase HPLC column (C₁₈, 20-50% CH₃CN in 0.1% TFA/H₂O over 30 min gradient) to afford the titled compounds as white powders. All characterized by LC-MS.

Compounds 10J-L were analyzed in an in vitro functional assay at the GLP-1 receptor following the methods described in Example 16. The results are in Table 4:

TABLE 4

| Compound | Cyclase GLP-1 Receptor $EC_{50}$ (nM) |
|---|---|
| 10J | 0.1 |
| 10K | 0.03 |
| 10L | 0.005 |

TABLE 4-continued

| Compound | Cyclase GLP-1 Receptor $EC_{50}$ (nM) |
|---|---|
| 10M | 0.007 |
| 10N | 0.01 |

All publications and patent applications are incorporated herein by reference. Although the foregoing has been described in detail for purposes of clarity of understanding, it will be apparent to one of ordinary skill in the art that changes and modifications may be made without departing from the spirit or scope of the disclosure or appended claims.

What is claimed is:

1. A peptide comprising the amino acid sequence as set forth in Formula (D):

$Xaa_1Xaa_2Xaa_3Xaa_4$TFTSDLSKQX$aa_{14}$EEEAVRLFIEX$aa_{25}$LKNGGPSSGAPPPS-Z (SEQ ID No:3);

wherein:
$Xaa_1$ is His;
$Xaa_2$ is Gly or dAla;
$Xaa_3$ is Pro;
$Xaa_4$ is Gly;
$Xaa_{14}$ is Leu or Met;
$Xaa_{25}$ is Phe or Trp;
and
Z is OH or $NH_2$.

2. The peptide of claim 1, wherein the peptide comprises the amino sequence as set forth in SEQ ID NO:40, 41, or 42.

3. A method for lowering blood glucose levels in a patient in need thereof, the method comprising administering to the patient a therapeutically effective amount of the peptide of claim 1 to lower blood glucose levels in the patient.

* * * * *